(12) United States Patent
Slatkine et al.

(10) Patent No.: US 11,083,515 B2
(45) Date of Patent: Aug. 10, 2021

(54) METHODS AND DEVICES FOR THERMAL TISSUE VAPORIZATION AND COMPRESSION

(71) Applicant: Novoxel Ltd., Natania (IL)

(72) Inventors: Michael Slatkine, Herzlia (IL); Ronen Shavit, Tel-Aviv (IL); Raphael Shavit, Tel-Aviv (IL)

(73) Assignee: NOVOXEL LTD., Natania (IL)

( * ) Notice: Subject to any disclaimer, the term of this patent is extended or adjusted under 35 U.S.C. 154(b) by 978 days.

(21) Appl. No.: 15/511,269

(22) PCT Filed: Sep. 10, 2015

(86) PCT No.: PCT/IL2015/050924
§ 371 (c)(1),
(2) Date: Mar. 15, 2017

(87) PCT Pub. No.: WO2016/042546
PCT Pub. Date: Mar. 24, 2016

(65) Prior Publication Data
US 2017/0281266 A1 Oct. 5, 2017

Related U.S. Application Data

(63) Continuation-in-part of application No. PCT/IL2014/051103, filed on Dec. 16, 2014.
(Continued)

(51) Int. Cl.
*A61B 18/12* (2006.01)
*A61B 18/14* (2006.01)
(Continued)

(52) U.S. Cl.
CPC .......... *A61B 18/1477* (2013.01); *A61B 18/14* (2013.01); *A61B 2017/00526* (2013.01);
(Continued)

(58) Field of Classification Search
CPC ................ A61B 18/14; A61B 18/1477; A61B 2018/00041; A61B 2018/00148; A61B 2018/0047; A61B 2018/143
See application file for complete search history.

(56) References Cited

U.S. PATENT DOCUMENTS 2,894,512 A 7/1959 Tapper
3,020,912 A 2/1962 Chester
(Continued)

FOREIGN PATENT DOCUMENTS

CN 1621102 A 6/2005
CN 1623515 A 6/2005
(Continued)

OTHER PUBLICATIONS

Supplementary European Search Report and the European Search Opinion dated Aug. 4, 2017 From the European Patent Office Re. Application No. 14871250.8. (7 Pages).
(Continued)

*Primary Examiner* — Daniel W Fowler
(74) *Attorney, Agent, or Firm* — Brown Rudnick LLP

(57) ABSTRACT

A method of producing an array of sharp tips including a biocompatible coating, wherein the biocompatible coating is thicker at a sharp end of the sharp tips than at a broader section of the sharp tips, the method including providing an array of sharp tips, and coating the sharp end of the sharp tips differentially from coating the broader section of the sharp tips. A method of treating skin including producing a hollow in the skin by heating and mechanically compressing epidermis while retaining a covering of stratum corneum. A method of treating tissue including heating a tip to a temperature suitable for producing a crater in the tissue, advancing the tip toward the tissue, detecting when the tip comes into contact with the tissue by detecting a change in mechanical resistance to the advancing, and measuring the
(Continued)

mechanical resistance to the advancing. Related apparatus and methods are also described.

35 Claims, 27 Drawing Sheets

Related U.S. Application Data

(60) Provisional application No. 62/050,244, filed on Sep. 15, 2014, provisional application No. 61/917,435, filed on Dec. 18, 2013.

(51) Int. Cl.
    A61B 17/00 (2006.01)
    A61B 18/00 (2006.01)

(52) U.S. Cl.
    CPC ............ A61B 2018/00041 (2013.01); A61B 2018/0047 (2013.01); A61B 2018/00148 (2013.01); A61B 2018/143 (2013.01)

(56) References Cited

U.S. PATENT DOCUMENTS

| | | | |
|---|---|---|---|
| 3,875,944 A | 4/1975 | Toyama | |
| 4,736,743 A | 4/1988 | Daikuzono | |
| 4,799,478 A | 1/1989 | Fedorov et al. | |
| 5,019,076 A | 5/1991 | Yamanashi et al. | |
| 5,064,426 A | 11/1991 | Huebsch | |
| 5,123,028 A | 6/1992 | Hobart et al. | |
| 5,318,562 A | 6/1994 | Levy et al. | |
| 5,360,447 A | 11/1994 | Koop | |
| 5,411,502 A | 5/1995 | Zair | |
| 5,423,803 A | 6/1995 | Tankovich et al. | |
| 5,498,258 A | 3/1996 | Hakky et al. | |
| 5,655,547 A | 8/1997 | Karni | |
| 5,733,278 A | 3/1998 | Slatkine et al. | |
| 5,885,211 A | 3/1999 | Eppstein et al. | |
| 5,899,915 A | 5/1999 | Saadat | |
| 5,908,419 A | 6/1999 | Hahnen et al. | |
| 6,142,939 A | 11/2000 | Eppstein et al. | |
| 6,296,639 B1 | 10/2001 | Truckai et al. | |
| 6,383,179 B1 | 5/2002 | Neuberger | |
| 6,475,138 B1 | 11/2002 | Schechter et al. | |
| 6,475,547 B1 | 11/2002 | Lignell et al. | |
| 6,530,915 B1 | 3/2003 | Eppstein et al. | |
| 6,678,556 B1 | 1/2004 | Nolan et al. | |
| 7,537,590 B2 | 5/2009 | Santini et al. | |
| 8,690,865 B2 | 4/2014 | Prausnitz et al. | |
| 8,808,311 B2 | 8/2014 | Heinrich et al. | |
| 8,834,461 B2 | 9/2014 | Werneth et al. | |
| 8,876,811 B2 | 11/2014 | Lewinsky et al. | |
| 9,402,678 B2 | 8/2016 | Slatkine | |
| 2001/0020167 A1 | 9/2001 | Woloszko et al. | |
| 2002/0120260 A1 | 8/2002 | Morris et al. | |
| 2002/0169394 A1 | 11/2002 | Eppstein et al. | |
| 2003/0092982 A1 | 5/2003 | Eppstein | |
| 2003/0097126 A1 | 5/2003 | Woloszko et al. | |
| 2003/0109802 A1 | 6/2003 | Laeseke et al. | |
| 2003/0212396 A1 | 11/2003 | Eggers et al. | |
| 2003/0216717 A1 | 11/2003 | Nahen et al. | |
| 2004/0176754 A1* | 9/2004 | Island | A61B 18/203 606/9 |
| 2004/0181214 A1 | 9/2004 | Garabedian et al. | |
| 2004/0225286 A1 | 11/2004 | Elliott | |
| 2005/0131345 A1* | 6/2005 | Miller | A61B 17/3476 604/117 |
| 2005/0203413 A1* | 9/2005 | Fichtinger | A61B 8/0841 600/461 |
| 2006/0024358 A1 | 2/2006 | Santini et al. | |
| 2006/0084942 A1 | 4/2006 | Kim et al. | |
| 2006/0095103 A1 | 5/2006 | Eggers et al. | |
| 2007/0060989 A1* | 3/2007 | Deem | A61B 18/1477 607/99 |
| 2007/0149991 A1 | 6/2007 | Mulholland | |
| 2007/0167918 A1 | 7/2007 | Reed et al. | |
| 2007/0191827 A1 | 8/2007 | Lischinsky et al. | |
| 2008/0039832 A1 | 2/2008 | Palanlcer et al. | |
| 2008/0063866 A1* | 3/2008 | Allen | A61B 5/685 428/389 |
| 2008/0082090 A1 | 4/2008 | Manstein | |
| 2008/0091182 A1 | 4/2008 | Mehta et al. | |
| 2008/0091183 A1 | 4/2008 | Knopp et al. | |
| 2008/0091184 A1 | 4/2008 | Knopp et al. | |
| 2008/0091185 A1 | 4/2008 | McGill et al. | |
| 2008/0097558 A1 | 4/2008 | Eggers et al. | |
| 2008/0119761 A1 | 5/2008 | Boecker et al. | |
| 2008/0125775 A1 | 5/2008 | Morris | |
| 2008/0154254 A1 | 6/2008 | Burger et al. | |
| 2008/0215039 A1 | 9/2008 | Slatkine et al. | |
| 2008/0281389 A1 | 11/2008 | Knopp et al. | |
| 2008/0312647 A1 | 12/2008 | Knopp et al. | |
| 2009/0036958 A1 | 2/2009 | Mehta et al. | |
| 2009/0099534 A1 | 4/2009 | Lee et al. | |
| 2009/0112205 A1 | 4/2009 | McGill et al. | |
| 2009/0156958 A1 | 6/2009 | Mehta et al. | |
| 2009/0222000 A1 | 9/2009 | Pacey | |
| 2009/0234214 A1 | 9/2009 | Santini et al. | |
| 2009/0275899 A1 | 11/2009 | Deem et al. | |
| 2009/0299361 A1 | 12/2009 | Flyash et al. | |
| 2009/0326571 A1 | 12/2009 | Mulholland | |
| 2010/0010480 A1 | 1/2010 | Mehta et al. | |
| 2010/0121307 A1 | 5/2010 | Lockard et al. | |
| 2010/0217253 A1 | 8/2010 | Mehta | |
| 2010/0217254 A1 | 8/2010 | Mehta | |
| 2010/0228243 A1 | 9/2010 | Mehta | |
| 2010/0262135 A1 | 10/2010 | Berube | |
| 2011/0028970 A1 | 2/2011 | Woloszko et al. | |
| 2011/0264084 A1 | 10/2011 | Reid | |
| 2011/0288543 A1 | 11/2011 | Cheng et al. | |
| 2012/0123401 A1 | 5/2012 | Slatkine | |
| 2012/0143178 A9 | 6/2012 | Mehta | |
| 2012/0158100 A1 | 6/2012 | Schomacker | |
| 2012/0185029 A1 | 7/2012 | Flyash et al. | |
| 2012/0245455 A1* | 9/2012 | Bauman | A61B 17/3403 600/424 |
| 2012/0330295 A1 | 12/2012 | Manwaring et al. | |
| 2013/0123767 A1 | 5/2013 | Clark, III et al. | |
| 2013/0184609 A1 | 7/2013 | Lee et al. | |
| 2013/0197473 A1 | 8/2013 | McMillan | |
| 2014/0171934 A1 | 6/2014 | Flyash et al. | |
| 2016/0317208 A1 | 11/2016 | Slatkine et al. | |
| 2016/0331440 A1 | 11/2016 | Slatkine | |
| 2017/0281256 A1 | 10/2017 | Slatkine et al. | |

FOREIGN PATENT DOCUMENTS

| | | |
|---|---|---|
| CN | 101322645 A | 12/2008 |
| CN | 102333565 A | 1/2012 |
| EP | 1563788 | 8/2005 |
| EP | 1726329 | 11/2006 |
| EP | 1905516 | 4/2008 |
| EP | 2666424 | 11/2013 |
| FR | 2911059 | 7/2008 |
| JP | 03-063045 | 3/1991 |
| JP | 2002532165 A | 10/2002 |
| JP | 2006-192285 | 7/2006 |
| JP | 2007-531578 | 11/2007 |
| JP | 2010502268 A | 1/2010 |
| JP | 2013519450 A | 5/2013 |
| KR | 10-2009-0052631 | 5/2009 |
| KR | 10-0946363 | 3/2010 |
| WO | WO 91/10405 | 7/1991 |
| WO | WO 97/07734 | 3/1997 |
| WO | WO 2005/030071 | 4/2005 |
| WO | WO 2005/096979 | 10/2005 |
| WO | WO 2008/100118 | 8/2008 |
| WO | 2010-042996 A1 | 4/2010 |
| WO | WO 2010/137885 | 12/2010 |
| WO | 2011/013118 A2 | 2/2011 |
| WO | WO 2011/013118 | 2/2011 |
| WO | 2011148995 A1 | 12/2011 |
| WO | 2013/164996 A1 | 11/2013 |

(56) References Cited

FOREIGN PATENT DOCUMENTS

| | | |
|---|---|---|
| WO | WO 2015/092791 | 6/2015 |
| WO | WO 2016/042546 | 3/2016 |
| WO | WO 2016/042547 | 3/2016 |

OTHER PUBLICATIONS

Communication Pursuant to Article 94(3) EPC Dated Jun. 8, 2018 From the European Patent Office Re. Application No. 10747084.1. (5 Pages).
English Translation of Japanese Office Action issued in Japanese Application No. 2017-514406, dated Aug. 27, 2019.
Chinese Search Report issued in Chinese Application No. 2015800610556, dated Jun. 21, 2019.
Notification of Office Action dated Nov. 29, 2017 From the State Intellectual Property Office of the People's Republic of China Re. Application No. 201480074496.5 and Its Translation Into English. (9 pages).
Official Action dated May 25, 2018 From the US Patent and Trademark Office Re. U.S. Appl. No. 15/218,129. (36 pages).
Restriction Official Action dated May 18, 2018 From the US Patent and Trademark Office Re. U.S. Appl. No. 15/105,086. (12 pages).
Communication Pursuant to Article 94(3) EPC Dated Apr. 16, 2018 From the European Patent Office Re. Application No. 14871250.8. (8 Pages).
Applicant-Initiated Interview Summary dated Jul. 13, 2015 From the US Patent and Trademark Office Re. U.S. Appl. No. 13/386,697.
Communication Relating to the Results of the Partial International Search dated Dec. 3, 2010 From the International Searching Authority Re. Application No. PCT/IL2010/000588.
Communication Relating to the Results of the Partial International Search dated Feb. 5, 2016 From the International Searching Authority Re. Application No. PCT/IL2015/050924.
Examiner-Initiated Interview Summary and Advisory Action Before the Filing of An Appeal Brief dated Sep. 8, 2015 From the US Patent and Trademark Office Re. U.S. Appl. No. 13/386,697.
International Preliminary Report on Patentability dated Feb. 9, 2012 From the International Bureau of WIPO Re. Application No. PCT/IL2010/000588.
International Preliminary Report on Patentability dated Jun. 30, 2016 From the International Bureau of WIPO Re. Application No. PCT/IL2014/051103.
International Preliminary Report on Patentability dated Mar. 30, 2017 From the International Bureau of WIPO Re. Application No. PCT/IL2015/050924. (12 Pages).
International Preliminary Report on Patentability dated Mar. 30, 2017 From the International Bureau of WIPO Re. Application No. PCT/IL2015/050925. (10 Pages).
International Search Report and the Written Opinion dated Mar. 4, 2011 From the International Searching Authority Re. Application No. PCT/IL2010/000588.
International Search Report and the Written Opinion dated Jan. 8, 2016 From the International Searching Authority Re. Application No. PCT/IL2015/050925.
International Search Report and the Written Opinion dated Apr. 14, 2016 From the International Searching Authority Re. Application No. PCT/IL2015/050924.
International Search Report and the Written Opinion dated Jul. 22, 2015 From the International Searching Authority Re. Application No. PCT/IL2014/51103.
Invitation to Pay Additional Fees Dated May 13, 2015 From the International Searching Authority Re. Application No. PCT/IL2014/051103.
Notice Of Allowance dated Mar. 29, 2016 From the US Patent and Trademark Office Re. U.S. Appl. No. 13/386,697.
Notice of Reason for Rejection dated Apr. 4, 2014 From the Patent Office of Japan Re. Application No. 2012-522334 and Its Translation Into English.
Notice of Reason for Rejection dated Nov. 7, 2014 From the Patent Office of Japan Re. Application No. 2012-522334 and Its Translation Into English.
Office Action and Search Report dated Jul. 31, 2012 From the Israel Patent Office Re. Application No. 200081 and Its Translation Into English.
Office Action dated Feb. 2, 2014 From the Israel Patent Office Re. Application No. 217734 and Its Translation Into English.
Office Action dated Aug. 5, 2012 From the Israel Patent Office Re. Application No. 201246 and Its Translation Into English.
Office Action dated Dec. 14, 2014 From the Israel Patent Office Re. Application No. 217734.
Official Action dated Apr. 6, 2015 From the US Patent and Trademark Office Re. U.S. Appl. No. 13/386,697.
Official Action dated Nov. 6, 2014 From the US Patent and Trademark Office Re. U.S. Appl. No. 13/386,697.
Restriction Official Action dated Aug. 29, 2014 From the US Patent and Trademark Office Re. U.S. Appl. No. 13/386,697.
Translation Dated Jan. 15, 2015 of Office Action dated Dec. 14, 2014 From the Israel Patent Office Re. Application No. 217734.
Chernoff et al. "SilkTouch: A New Technology for Skin Resurfacing in Aesthetic Surgery", Journal of Clinical Laser Medicine & Surgery, 13(2): 97-100, 1995.
Dornier "Dornier Medials Fibertom 8100", Dornier MedTech, Product Sheet, 4 P., Feb. 2007.
Fee "Use of the Shaw Scalpel in Head and Neck Surgery", Otolaryngology—Head and Neck Surgery, 89(4): 515-519, Jul.-Aug. 1981.
Lowe et al. "Skin Resurfacing With the Ultrapulse Carbon Dioxide Laser. Observations on 100 Patients", Dermatologic Surgery, 21(12): 1025-1029, Dec. 1995.
Mestel "M3A10 Viscous Flow: Lubrication Theory—Flow in Thin Films", Graduate Course on Viscous Flow in Imperial College, London, UK, 4 P., 2013.
Park et al. "The Effect of Heat on Skin Permeability", International Journal of Pharmacology, 359(1-2): 94-103, Jul. 9, 2008.
PhotoMedex "Delivery Systems and Accessories for the SLT Contact Laser™ System", Surgical Laser Technology, PhotoMedex Inc., Catalog, 8 P., 2007.
Reed "Preventing Patient Thermal Burns From Electrosurgical Instruments", Reprint of Infection Control Today, 3 P., 2013.
Intention to grant and Supplemental Search Report issued in European Patent Application No. 15793914.1, dated Nov. 30, 2020, 10 pages.
Extended European Search Report issued in European Application No. 21000004.8, dated May 25, 2021, 8 pages.

* cited by examiner

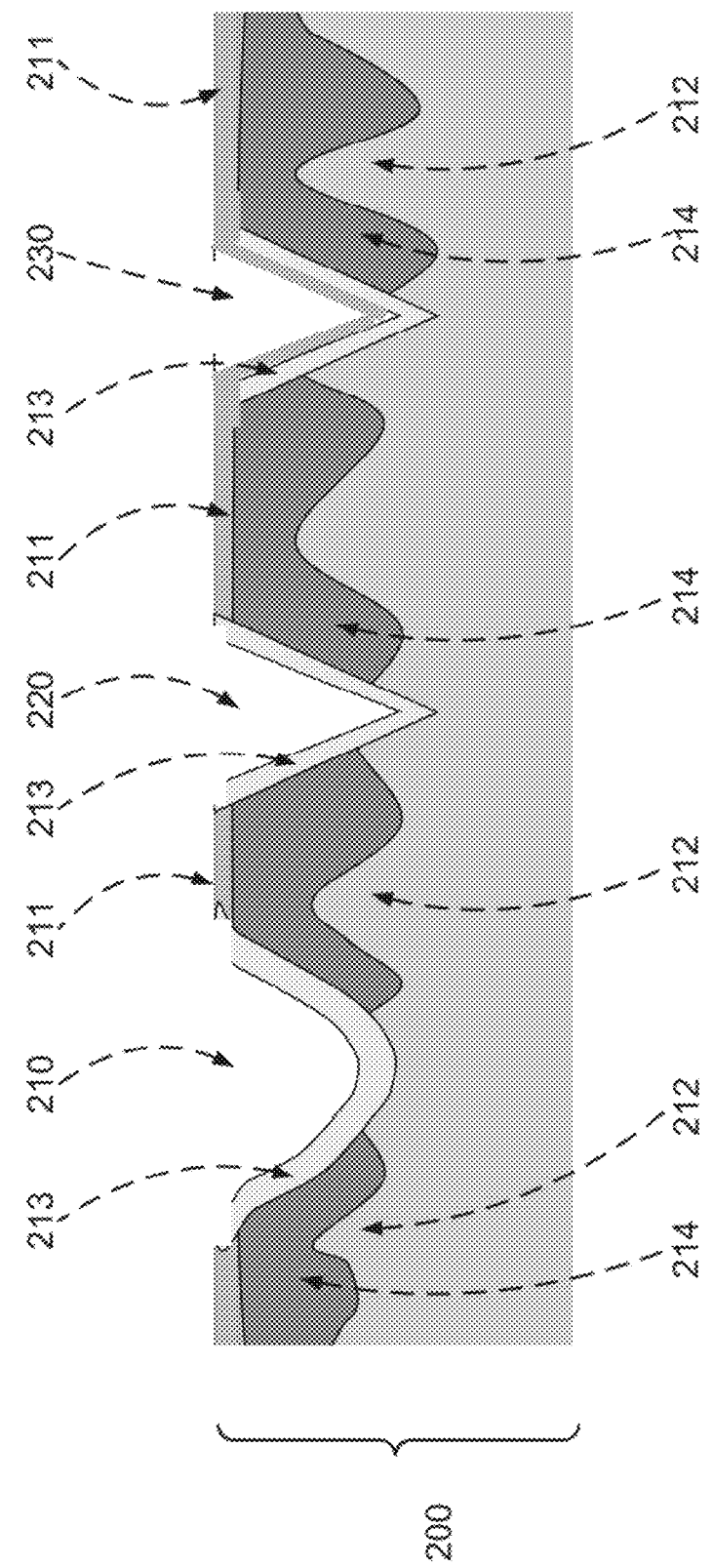

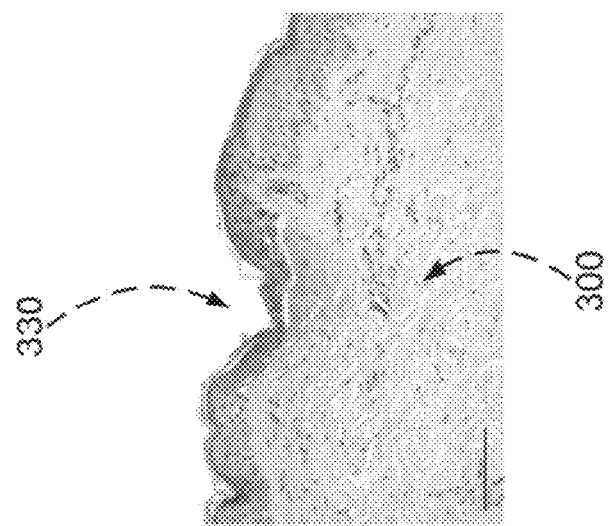
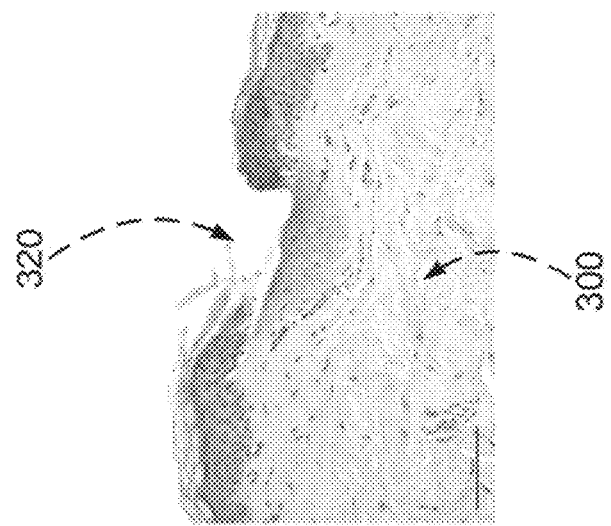
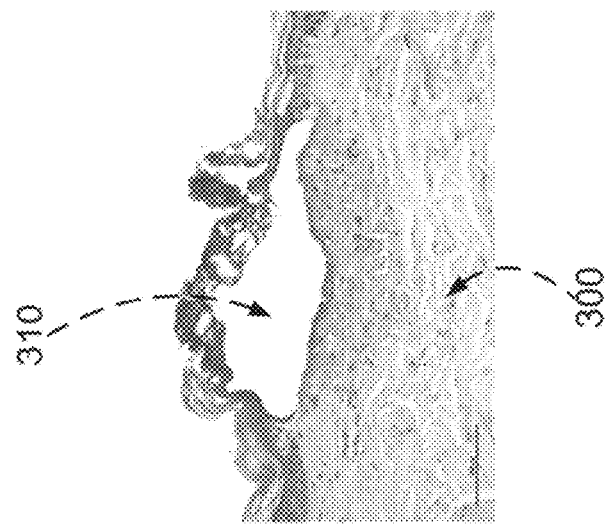

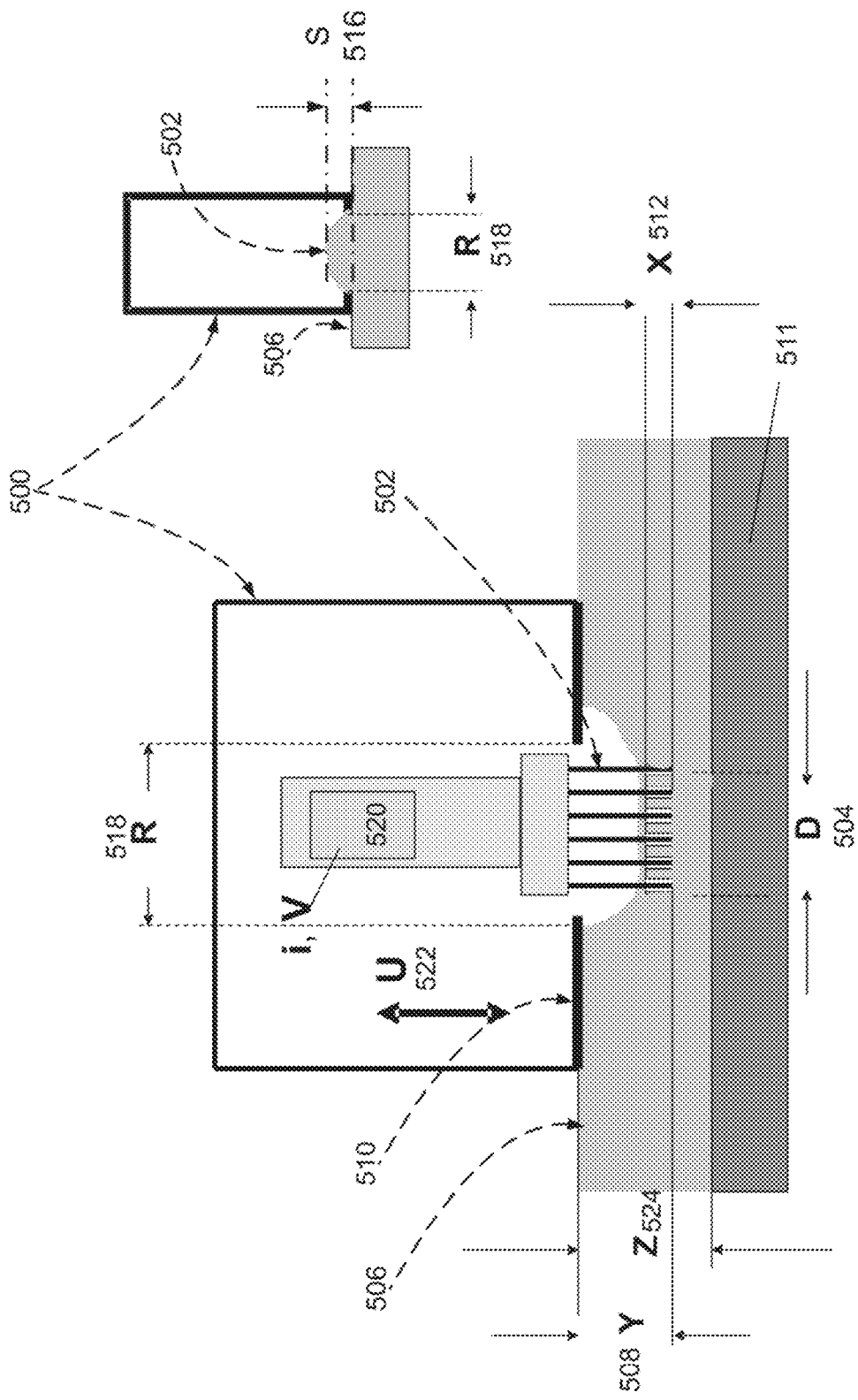

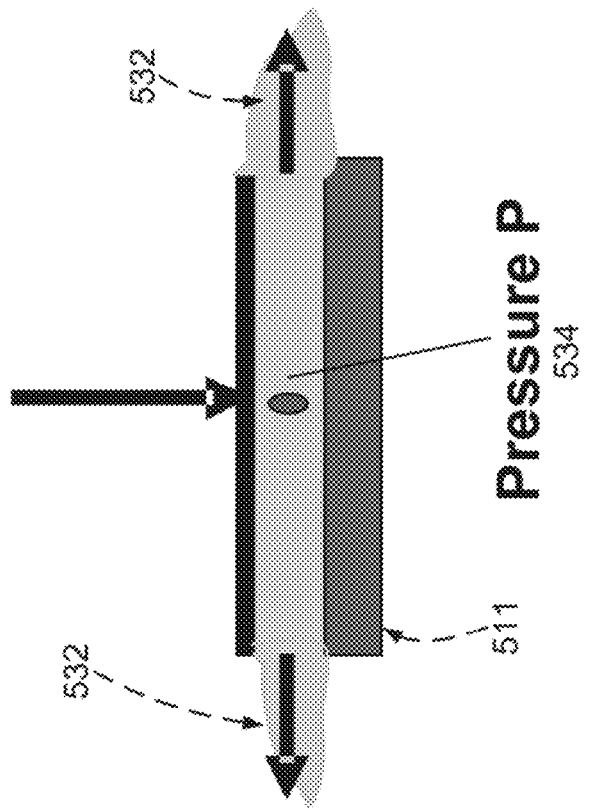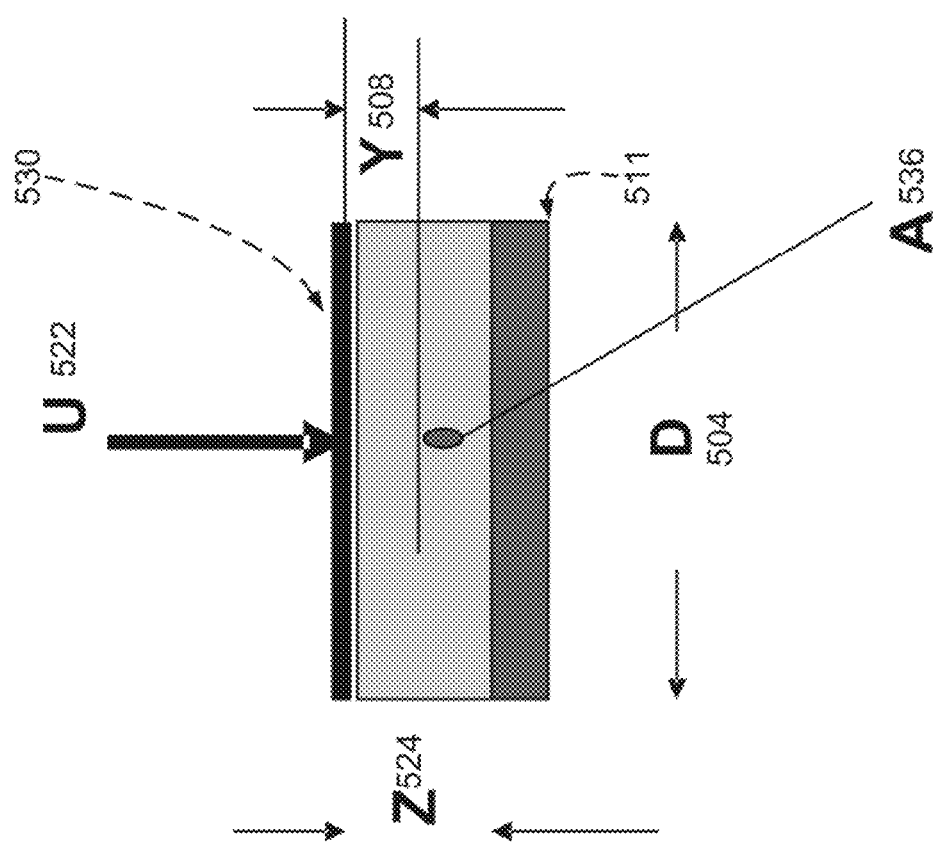

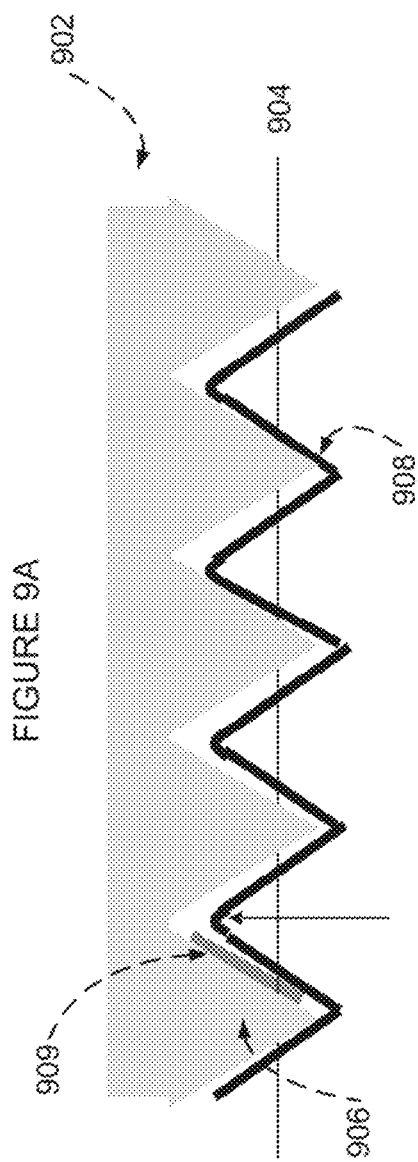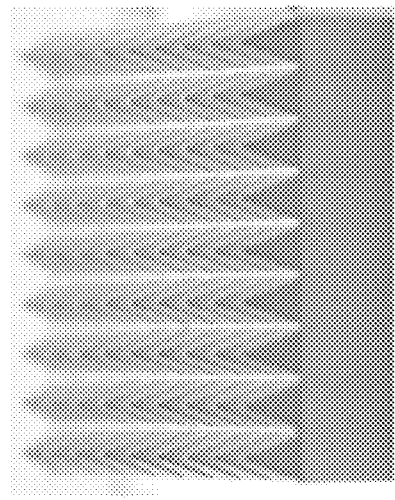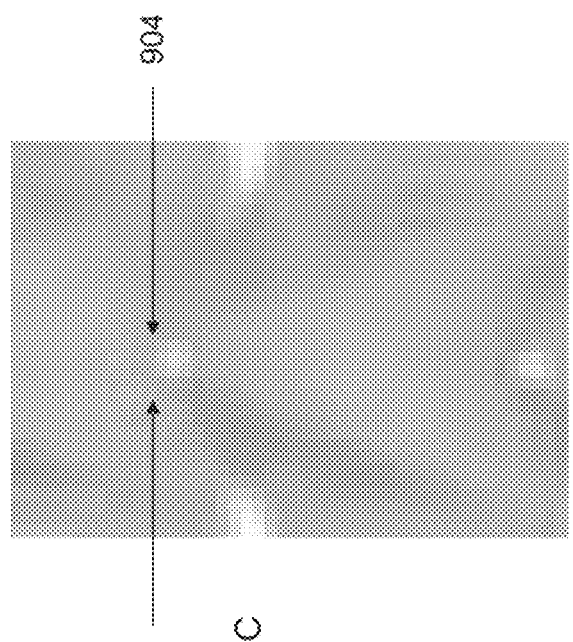

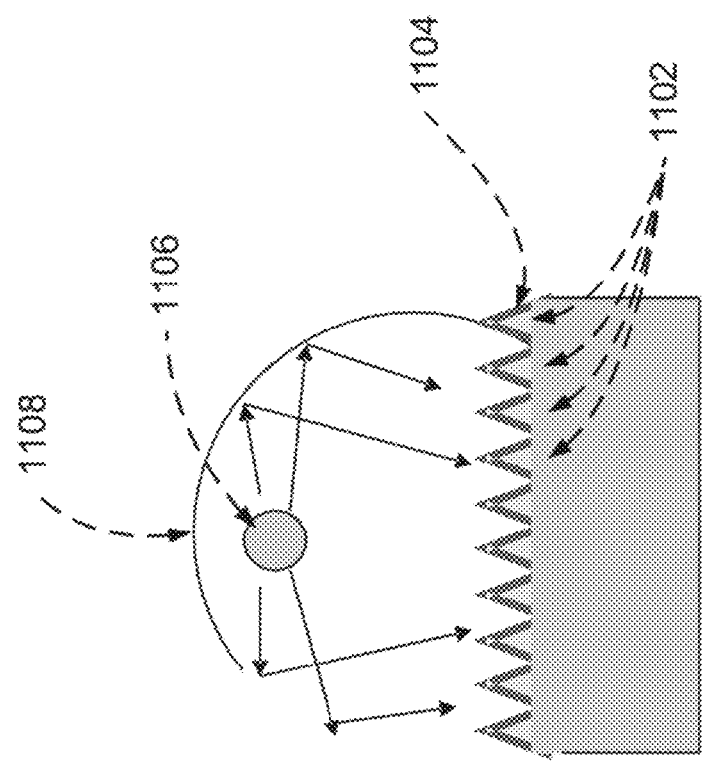

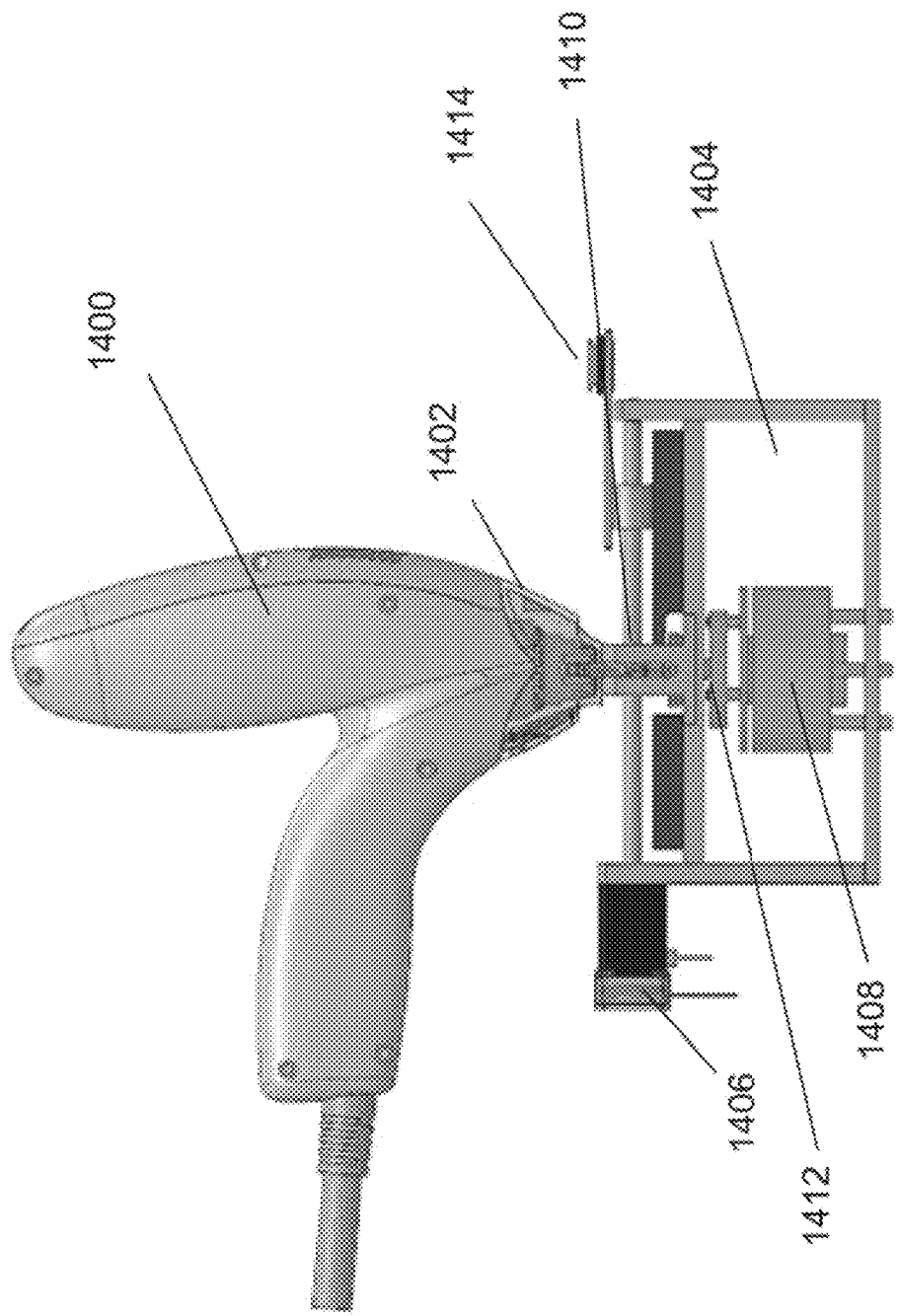

METHODS AND DEVICES FOR THERMAL TISSUE VAPORIZATION AND COMPRESSION

RELATED APPLICATIONS

This application is a National Phase of PCT Patent Application No. PCT/IL2015/050924 having International Filing date of Sep. 10, 2015, which claims the benefit of priority under 35 USC § 119(e) of U.S. Provisional Patent Application No. 62/050,244 filed on Sep. 15, 2014, and which is also a Continuation-in-Part (CIP) of PCT Patent Application No. PCT/IL2014/051103 filed on Dec. 16, 2014, which claims the benefit of priority under 35 USC § 119(e) of U.S. Provisional Patent Application No. 61/917, 435 filed on Dec. 18, 2013. The contents of the above applications are all incorporated by reference as if fully set forth herein in their entirety.

PCT Patent Application No. PCT/IL2015/050924 is also related to co-filed, co-pending and co-assigned PCT Patent Application No. PCT/IL2015/050925 filed on Sep. 10, 2015 titled "METHODS AND DEVICES FOR THERMAL SURGICAL VAPORIZATION AND INCISION OF TISSUE" by Michael SLATKINE, Ronen SHAVIT and Raphael SHAVIT, the disclosure of which is incorporated herein by reference.

FIELD AND BACKGROUND OF THE INVENTION

The present invention, in some embodiments thereof, relates to surgical methods and devices, and, more particularly, but not exclusively, to methods and devices for vaporization of tissue and even more particularly, but not exclusively, to methods and devices for production of arrays of micro depressions in skin.

Various techniques are known to perform tissue ablation, commonly involving the use of a pulsed laser or RF energy.

$CO_2$ as well as Erbium lasers are widely utilized in fractional skin resurfacing. They vaporize craters in tissue by a cell explosion effect which removes both stratum cornea as well as epidermal tissue.

Current methods of fractional skin rejuvenation include non ablative treatments. This is performed with infrared optical sources such as Erbium glass lasers operating at 1.5 micron wavelength which penetrate deep into tissue (~2 mm, deeper than the papillary dermis (~100 micron) depth, or infrared lamps equipped with an array of focusing microlenses. Such treatment devices are produced by Palomar Medical for example. In such cases the skin surface typically remains intact while deeper skin layers are heated and thermally injured. The injury level in the epidermis as well as in the papillary dermis with such lasers or infrared sources is much lower than injury level produced by ablative lasers such as CO2 or Erbium lasers. The current non ablative treatments have an advantage of immediate return to work since skin surface appears intact. A disadvantage is the milder clinical effect on fine wrinkles and skin texture.

Skin permeability to a large variety of drugs, creams and other substances is known to be low due to stratum cornea skin protection features. The increase of skin permeability by vaporization or highly damaging the stratum cornea layer of the skin without damaging the epidermis is described and explained in below-mentioned EP 1563788 as well as in below-mentioned article by Prausnitz. As described by Prausnitz, stratum cornea permeability to most drugs increases dramatically when attaining a temperature of 300 deg C. Thermal coagulation or denaturation of epidermal collagen and other proteins reduces the permeability enhancement by orders of magnitude.

Published PCT publication WO2011/013118 discloses a device for vaporizing a hole in tissue, including a vaporizing element, a heating element, configured to heat the vaporizing element, and a mechanism configured to advance the vaporizing element into a specific depth in the tissue and retract the vaporizing element from the tissue within a period of time long enough for the vaporizing element to vaporize the tissue and short enough to limit diffusion of heat beyond a predetermined collateral damage distance from the hole.

European patent application EP 1563788 discloses a method of enhancing the permeability of the skin to an analytic for diagnostic purposes or to a drug for therapeutic purposes is described utilizing micro-pore and optionally sonic energy and a chemical enhancer. If selected, the sonic energy may be modulated by means of frequency modulation, amplitude modulation, phase modulation, and/or combinations thereof. Micro-pore is accomplished by (a) ablating the stratum corneum by localized rapid heating of water such that water is vaporized, thus eroding cells; (b) puncturing the stratum corneum which a micro-lancet calibrated to form a micro-pore of up to about 1000 mu m in diameter; (c) ablating the stratum corneum by focusing a tightly focused beam of sonic energy onto the stratum corneum; (d) hydraulically puncturing the stratum corneum with a high-pressure jet of fluid to form a micro-pore of up to about 1000 mu m in diameter; or (e) puncturing the stratum corneum with short pulses of electricity to form a micro-pore of up to about 1000 mu m in diameter.

US published patent application number US2004/0181214 titled "PASSIVELY COOLED ARRAY" of Garabedian et al. discloses a tissue ablation system includes an elongated shaft, such as a surgical probe shaft, and an needle electrode array mounted to the distal end of the shaft, and an ablation source, such as, e.g., a radio frequency (RF) generator, for providing ablation energy to the electrode array. The tissue ablation system further includes a heat sink disposed within the distal end of the shaft in thermal communication with the needle electrode array. In this manner, thermal energy is drawn away from the needle electrode array, thereby cooling the electrode array and providing a more efficient ablation process. The tissue ablation system further comprises a coolant flow conduit in fluid communication with the heat sink, so that the thermal energy can be drawn away from the heat sink. In the preferred embodiment, the flow conduit includes a thermal exchange cavity in fluid communication with the heat sink, a cooling lumen for conveying a cooled medium (such as, e.g., saline at room temperature or below) to the thermal exchange cavity, and a return lumen for conveying a heated medium from the thermal exchange cavity. The tissue ablation system further comprises a pump assembly for conveying the cooled medium through the cooling lumen to the thermal exchange cavity at the distal end of the shaft.

Additional background art includes:

An article by Park J. H., Lee J. W., Kim Y. C., and Prausmitz M. R., titled "The effect of heat on skin permeability", published in Int J Pharm. Author manuscript; available in PMC 2009 Jul. 9.

A text book chapter found on the World Wide Web at wwwf(dot)imperial(dot)ac(dot)uk/~ajm8/M3A10/lub(dot)pdf.

U.S. Pat. No. 8,690,865 to Prausnitz et al.

The disclosures of all references mentioned above and throughout the present specification, as well as the disclosures of all references mentioned in those references, are hereby incorporated herein by reference.

SUMMARY OF THE INVENTION

The present invention, in some embodiments thereof, relates to surgical methods and devices, and, more particularly, but not exclusively, to methods and devices for vaporization of tissue and even more particularly, but not exclusively, to methods and devices for production of arrays of micro depressions in skin.

An aspect of some embodiments of the invention involves using a tip of a heated rod or an array of tips of one or more heated rods, to produce a crater in skin. In some embodiments, the crater is produced in the epidermis while keeping a top layer of stratum corneum, which may cover the crater and potentially help prevent infection and assist healing. In some embodiments the stratum corneum is partly damaged, such that a ratio of remaining stratum corneum area to an area of a produced crater is optionally in a range of at least 30% coverage, at least 50% coverage, at least 80% coverage, and even approximately 100% coverage—the stratum corneum may be damaged yet still cover most of the crater's area.

An aspect of some embodiments of the invention involves detecting when the tip(s) or array of tips comes in touch with skin, by detecting mechanical resistance of the tissue or skin to the tips pushing against it. Detecting when tip(s) come in touch with skin is meaningful when aiming for a specific depth and/or shape of the crater in the skin, since merely advancing tip(s) a specific distance beyond a plate (a distal gauge) placed upon the skin is likely to be inaccurate. It has been found that when placing a plate, which has openings for the tip(s) to go through, upon a skin, the skin may bulge into the openings, or otherwise not form a flat plane at the plate openings. A distance of advancement of a tip beyond the plate is not always equivalent to a depth of a crater formed in the skin. In order to control a depth of a crater formed in skin may be better done by detecting when the tip comes in touch with the skin and starts pushing against it.

An aspect of some embodiments of the invention includes measuring a speed of advancement of the tip(s), and detecting when the tip(s) movement is slowed by the skin.

An aspect of some embodiments of the invention involves manufacturing an array of tips such as mentioned above, coated with a biocompatible coating, suitable for withstanding high temperatures used for treatment, optionally withstanding even higher temperature which in some cases may be used to clean a used tip array by oxidizing residues and/or sterilizing.

Some embodiments of the invention are related to a thermal skin crushing element, such as a crushing rod, adapted to supply an amount of heat in a short amount of time to crush tissue or create a crater or depression while avoiding damage below the papillary dermis. The depression produced potentially remains depressed for a period of time, for example for half a day, a day, or a few days.

According to an aspect of some embodiments of the present invention there is provided an array of sharp tips for treating tissue including a plurality of sharp tips having a biocompatible coating, in which the biocompatible coating is capable of blocking diffusion of non-coating material through the coating material even while heated to a temperature greater than 400 degrees Celsius.

According to some embodiments of the invention, the biocompatible coating is thicker at a sharp end of the sharp tips than at a broader base of the sharp tips.

According to some embodiments of the invention, the biocompatible coating at the sharp end of the sharp tips is sufficient to block diffusion of non-coating material through the coating material to a level greater than 1% concentration of the non-coating material in the coating material even following heating to a temperature between 400 and 520 degrees Celsius for a duration of at least 20 minutes.

According to some embodiments of the invention, the biocompatible coating material includes gold.

According to some embodiments of the invention, the non-coating material includes a material selected from a group consisting of copper, stainless steel, titanium and tungsten.

According to an aspect of some embodiments of the present invention there is provided an array of sharp tips for heating and treating tissue, the array including a plurality of sharp tips connected by a common base, and a biocompatible coating disposed on a distal tip of the sharp tips, wherein the biocompatible coating has a higher thickness on the distal tip of the sharp tips than at a broader section of the sharp tips.

According to some embodiments of the invention, the biocompatible coating is designed to remain biocompatible at temperatures between 400 and 520 degrees Celsius for a duration of at least 20 minutes.

According to some embodiments of the invention, the common base is not biocompatible at temperatures between 400 and 520 degrees Celsius.

According to some embodiments of the invention, the distal ends of the sharp tips have a width of 50-1000 microns.

According to some embodiments of the invention, the biocompatible coating includes gold. According to some embodiments of the invention, the biocompatible coating is pure gold.

According to some embodiments of the invention, the biocompatible coating is designed to remain biocompatible during operation at 400 degrees Celsius. According to some embodiments of the invention, the biocompatible coating is designed to remain biocompatible following heating to a temperature of 500 degrees Celsius for a duration of 5 minutes.

According to some embodiments of the invention, the sharp tips and the base included a material selected from a group consisting of copper, stainless steel, titanium and tungsten.

According to an aspect of some embodiments of the present invention there is provided a method of producing an array of sharp tips including a biocompatible coating, wherein the biocompatible coating is thicker at a sharp end of the sharp tips than at a broader section of the sharp tips, the method including providing an array of sharp tips, and coating the sharp end of the sharp tips differentially from coating the broader section of the sharp tips.

According to some embodiments of the invention, the coating the sharp end of the sharp tips differentially from coating the broader section of the sharp tips includes electroplating the sharp tips, wherein the electric field at the sharp tips is larger than the electric field at the broader section.

According to some embodiments of the invention, the coating the sharp end of the sharp tips differentially from coating the broader section of the sharp tips includes coating by plasma deposition of the coating, wherein the electric field at the sharp tips is larger than the electric field at the broader section.

According to some embodiments of the invention, the coating the sharp end of the sharp tips differentially from coating the broader section of the sharp tips includes coating the sharp tips for a longer period of time than coating the broader section.

According to some embodiments of the invention, the biocompatible coating is thicker at a sharp end of the sharp tips than at the broader section of the sharp tips by at least a factor of 2.

According to an aspect of some embodiments of the present invention there is provided a method of producing an array of sharp metallic tips coated with a biocompatible coating, the method including providing an array of sharp tips, electroplating the array of tips with a first coating, providing a mask over the array of tips masking electroplating of the tip bases and exposing the tip distal ends, and electroplating the array of tips with a second biocompatible coating.

According to some embodiments of the invention, the mask includes an insulating mask.

According to some embodiments of the invention, the tips have a radius of curvature in a range from 50 to 200 microns.

According to some embodiments of the invention, the array of tips is produced by sintering a powder including a material selected from a group consisting of copper, stainless steel and titanium.

According to an aspect of some embodiments of the present invention there is provided a method of producing an array of sharp metallic tips coated with a biocompatible coating including providing a first array of sharp metallic tips, providing a titanium sheet shaped as an array of hollow sharp tips of dimensions suitable for fitting onto the first array of sharp metallic tips, placing the titanium sheet onto the first array of sharp metallic tips such that the tips of the first array of sharp metallic tips insert into the hollow sharp tips of the titanium sheet, attaching the titanium sheet onto the first array of sharp metallic tips with a heat conducting layer.

According to some embodiments of the invention, the attaching is by silver brazing.

According to some embodiments of the invention, the titanium sheet is produced by sintering. According to some embodiments of the invention, the titanium sheet is produced by coining. According to some embodiments of the invention, the titanium sheet is produced by embossment. According to some embodiments of the invention, the titanium sheet is produced by machining.

According to some embodiments of the invention, the sharp tips have an external distal tip width in a range from 100 to 250 microns.

According to an aspect of some embodiments of the present invention there is provided a method of treating skin including producing a hollow in the skin by heating and mechanically compressing epidermis while retaining a covering of stratum corneum.

According to some embodiments of the invention, the epidermis is denatured by the heating.

According to an aspect of some embodiments of the present invention there is provided a method of treating tissue including heating a tip to a temperature suitable for producing a crater in the tissue, advancing the tip toward the tissue, detecting when the tip comes into contact with the tissue by detecting a change in mechanical resistance to the advancing, and measuring the mechanical resistance to the advancing.

According to some embodiments of the invention, the advancing the tip toward the tissue includes rapidly advancing the tip toward the tissue.

According to some embodiments of the invention, further including when the tip comes into contact with the tissue, assessing mechanical compliance of the tissue based, at least in part, on the measuring the mechanical resistance to the advancing, and determining how to continuing to advance the tip based, at least in part, on one or more results of the assessing.

According to some embodiments of the invention, the determining includes determining a preselected distance to advance beyond the detection of contact with the tissue.

According to some embodiments of the invention, when the tip comes into contact with the tissue, starting to continuously assess mechanical compliance of the tissue.

According to some embodiments of the invention, the determining includes advancing beyond the detection of contact with the tissue as long as the mechanical compliance remains lower than a threshold value.

According to some embodiments of the invention, the determining includes advancing beyond the detection of contact with the tissue based, at least in part, on a result of calculating the following equation:

$$F = k*Y*D^4*\mu/t*(Z^3),$$

wherein F is a driving force advancing the tip, k is a constant, Y is a distance following contact with the tissue, D is an area of a cross section of the tip, $\mu$ is viscosity of the tissue, t is time measured following contact with the tissue, and Z is a distance from the tissue to a hard surface beneath the tissue.

According to some embodiments of the invention, the tissue includes skin and the hard surface includes bone.

According to an aspect of some embodiments of the present invention there is provided a system for producing a crater in tissue by advancing a heated tip into the tissue, including a module for detection when the heated tip comes into contact with the tissue by detecting a change in mechanical resistance to the advancing.

According to an aspect of some embodiments of the present invention there is provided a method of producing a crater in tissue including assessing mechanical compliance of tissue, providing a controller with input corresponding to a result of the assessing, heating a tip to a temperature suitable for producing the crater in the tissue, advancing the tip toward and into the tissue, detecting when the tip comes into contact with the tissue by detecting a change in resistance to the advancing, and advancing the tip into the tissue a specific distance beyond the detecting, wherein the specific distance is determined by the controller based, at least in part, on a result of the assessing.

According to an aspect of some embodiments of the present invention there is provided a method of detecting when a tip of a tool being advanced toward tissue comes into contact with the tissue by detecting a change in resistance to the advancing.

According to an aspect of some embodiments of the present invention there is provided a method of cleaning a tip used for vaporizing tissue by heating the tip to a temperature above 450 degrees Celsius.

According to some embodiments of the invention, the tip includes a biocompatible coating material and a non-coating material, and the heating to a temperature above 450 degrees Celsius includes heating the biocompatible coating material to a temperature above 450 degrees Celsius.

According to some embodiments of the invention, a duration of the heating is long enough to burn off residue and short enough to prevent diffusion of the non-coating material through the biocompatible coating material.

According to some embodiments of the invention, the biocompatible coating material is sufficient to block diffusion of non-coating material through the coating material to a level greater than 1% concentration of the non-coating material in the biocompatible coating material even following heating to a temperature between 400 and 520 degrees Celsius for a duration of at least 20 minutes.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

In the drawings:

FIG. 2 is a simplified illustration of skin showing three craters in the skin produced by three methods;

FIGS. 3A, 3B and 3C are images of three histology cross sections of three skin craters produced by three methods;

FIG. 5A is a simplified line drawing illustration of a device for skin treatment according to an example embodiment of the invention;

FIGS. 5B-D are simplified line drawing illustrations of the device of FIG. 5A, pressed against skin in an example embodiment of the invention where distance from skin surface to underlying bone is small;

FIG. 9A is a simplified line drawing illustration of an array of vaporizing tips according to an example embodiment of the invention;

FIGS. 9B and 9C are images of the example embodiment of FIG. 9A;

FIG. 11 is a simplified line drawing illustration of a heating lamp which heats a distal surface of an array of tips according to an example embodiment of the invention;

FIG. 14 is a simplified line drawing illustration of a mechanism for changing an array of tips according to another example embodiment of the invention;

DESCRIPTION OF SPECIFIC EMBODIMENTS OF THE INVENTION

Figure 1B:
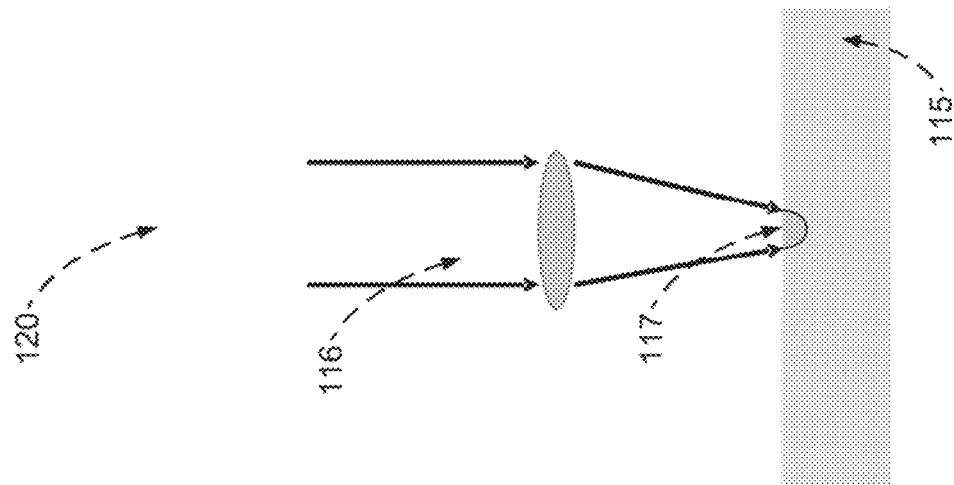
FIG. 1B is a simplified block diagram illustration of a focused beam CO2 laser 120 for vaporizing skin according to prior art.

The present invention, in some embodiments thereof, relates to surgical methods and devices, and, more particularly, but not exclusively, to methods and devices for vaporization of tissue and even more particularly, but not exclusively, to methods and devices for production of arrays of micro depressions in skin.

The term "skin" in all its grammatical forms is used throughout the present specification and claims interchangeably with the term "tissue" and its corresponding grammatical forms. Various implementations and embodiments of the invention which are described with reference to treating a skin are intended to apply also to treating other types of tissue.

The term "crater" in all its grammatical forms is used throughout the present specification and claims interchangeably with the term "depression" and its corresponding grammatical forms. Various implementation and embodiments of the invention which are described as producing craters in tissue are intended to apply also to producing depressions in tissue.

It is one purpose of embodiments of the current invention to overcome disadvantages of prior art while controlling a depth of vaporization of tissue with high temperature tips as well as improving post treatment conditions of patients.

Overview

An aspect of some embodiments of the invention involves using a tip of a heated rod or an array of tips of one or more heated rods, to produce a crater in skin. In some embodiments, the crater is produced in the epidermis while keeping at least some top layer of stratum corneum, which may cover the crater and potentially help prevent infection and assist healing.

An aspect of some embodiments of the invention involves a vaporizing element, such as a vaporizing rod, adapted to supply a large amount of heat in a short amount of time to produce the crater, while avoiding charring of the tissue. In some embodiments, holes, grooves, craters or indentations are produced in the tissue.

An aspect of some embodiments of the invention involves detecting when the tip(s) or array of tips comes in touch with skin, by detecting the mechanical resistance of the skin to the tips pushing against it. The mechanical resistance is detected, and optionally used for one or more uses. By way of one non-limiting example, detecting the mechanical resistance of the skin allows precise measurement of an advance from the point of touching the skin. By way of another non-limiting example, detecting the mechanical resistance of the skin enables determining a type of tissue being treated, and using the determination to calculate treatment parameters, such as depth of advancing the tip(s), speed of advancing the tip(s), and so on.

In some embodiments detecting when tip(s) come in touch with skin is meaningful when aiming for a specific depth and/or shape of the crater in the skin, since merely advancing tip(s) a specific distance beyond a plate placed upon the skin is likely to be inaccurate. It has been found that when placing a plate, which has openings for the tip(s) to go through, upon a skin, the skin may bulge into the openings, or otherwise not form a flat plane at the plate openings. A distance of advancement of a tip beyond the plate is not always equivalent to a depth of a crater formed in the skin. In order to control a depth of a crater formed in skin may be better done by detecting when the tip comes in touch with the skin and starts pushing against it.

An aspect of some embodiments of the invention includes measuring a speed of advancement of the tip(s), and detecting when the tip(s) movement is slowed by the skin.

An aspect of some embodiments of the invention includes measuring electric parameters such as current or voltage or pulse width (under Pulse Width Modulation) used in a motor for advancing the tip(s). When the tip(s) come into contact with skin the speed may change, or the electric parameters required to maintain the advance may change.

An aspect of some embodiments of the invention involves manufacturing an array of tips such as mentioned above, coated with a biocompatible coating, suitable for withstanding high temperatures used for treatment, optionally withstanding even higher temperature which in some cases may be used to clean a used tip array by combustion of carbon compounds and/or oxidizing residues and/or sterilizing.

In some embodiments the biocompatible coating material is selected to be capable of blocking diffusion of a non-coating material through the coating material even while heated to high temperatures over a period of time.

In some embodiments the biocompatible coating material is thicker at a sharp end of the tips than at a broader base of the tips. The different thickness may potentially be beneficial in blocking diffusion at a business end of the tips, which contacts tissue. Another potential benefit of the different thickness may be when using an expensive biocompatible coating material such as gold, by providing sufficient coating at the business end of the tips, which contacts tissue, and saving gold in a section of the tips which does not contact tissue.

Some embodiments of the invention are related to a thermal skin crushing element, such as a crushing rod, adapted to supply an amount of heat in a short amount of time to crush tissue or create a crater or depression while avoiding damage below the papillary dermis. The depression produced potentially remains depressed for a long time, for example for half a day, a day, or a few days.

An aspect of some embodiments of the invention relates to a generation of arrays of thermal micro-depressions in the skin, in some embodiments optionally without removing the stratum cornea. While vaporizing craters in tissue such as fractional vaporization of skin in aesthetic treatments, the stratum cornea is removed or partially removed as well. This happens with previous ablative technologies including $CO_2$ or Erbium lasers as well as in a system as described in above-mentioned EP 1563788, which is limited only to stratum cornea ablation. The efficacy of aesthetic treatments for improvement of skin texture, including fine wrinkles, is based on thermally injuring the papillary dermis while trying to minimize collateral thermal damage.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Figure 1A:
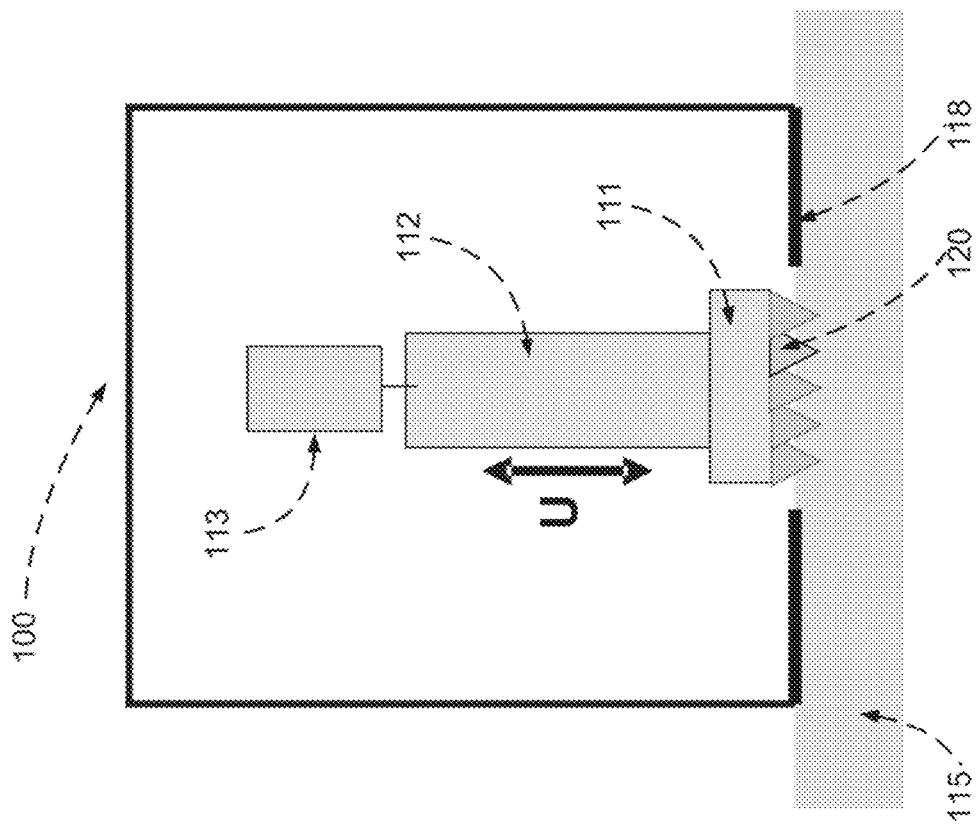
FIG. 1A is a simplified block diagram illustration of a device for vaporizing skin according to an embodiment of the invention.

Reference is now made to FIG. 1A, which is a simplified block diagram illustration of a device 100 for vaporizing skin according to an embodiment of the invention.

FIG. 1A depicts an array of metallic tips 120 in contact with a heater 111. The heater is held on a rod 112 which is driven back and forth toward and away from tissue surface 115 in a direction and speed U by a motor 113. The array of (pyramidal or conical or flat) metallic tips 120 is optionally heated to a temperature between 200-600 deg C., typically 400 deg C., and gets in contact with the tissue surface 115 for a fraction of a second, typically between 0.1 milliseconds to 25 milliseconds, optionally dependent on desired skin treatment results. An array of craters is typically produced and skin remodeling is typically achieved. Tissue vaporization and collateral thermal damage depend on contact duration and/or tip protrusion from a distal plane 118 of the device 100.

In some embodiments, not shown in FIG. 1A, the array of metallic tips 120 may optionally include one or more, or an array of blades, and/or arrow-like tips, with various diameters, optionally used for cutting soft tissue and/or for evaporating moles, lesions, tumors, etc.

Reference is now made to FIG. 1B, which is a simplified block diagram illustration of a focused beam CO2 laser 120 for vaporizing skin according to prior art. FIG. 1B depicts a focused beam 116 of a prior art CO2 laser which is focused at point 117 on the tissue surface 115. Infrared light absorption on the skin surface down to a depth of ~50 micron generates vaporization of a crater with collateral thermal damage.

Reference is now made to FIG. 2, which is a simplified illustration of skin 200 showing three craters 210 220 230 in the skin 200 produced by three methods.

FIG. 2 depicts a first vaporized crater 210 in the skin 200 as typically obtained by a $CO_2$ laser, a second vaporized crater 220 as typically obtained by a high temperature pyramidal tip at 400 deg C. such as described by above-mentioned patent application number WO2011/013118 or obtainable by an embodiment of the invention, and a third thermally compressed crater 230 such as obtainable by an embodiment of the invention.

FIG. 2 depicts schematically three types of craters 210 220 230 produced during fractional skin resurfacing.

The first crater 210 is produced by action of a $CO_2$ laser according to state of the art laser treatments. In many cases of $CO_2$ treatments, arrays of the first type of crater 210 are produced. During the vaporization process, the ~20 micron thick stratum corneum 211 is vaporized as well as a result of an explosion of water vapors inside cells. In most such cases, vaporized crater depth is typically through epidermis 214 down to the papillary dermis 212 with thermal collateral damage 123 of ~100-150 micron. Each such first crater 210 of approximately 300 micron diameter and approximately 100-150 micron depth is an open wound which may be infected. In many typical cases there are ~100 craters per $cm^2$, and a treatment area is typically $10\times10$ $cm^2$. Thus infection presents a risk.

The second crater 220 is produced by technology such as described in WO2011/013118 and/or such as obtainable by an embodiment of the current invention. For example, the second crater 220 may be vaporized by a copper tip plated with gold or by a stainless steel tip plated with gold or covered with titanium. The tip temperature may be 400 deg C. Skin contact duration may be 1-14 milliseconds by a copper tip and/or two consequential pulses of 9 milliseconds each by a stainless steel tip and/or a titanium tip. Other thermal and treatment parameters are also described below. The second crater 220 is also typically an open wound, extending through epidermis 214. However, there are a few advantages to the second crater 220 over the first crater 210 as will be explained below. However, the potential removal of the stratum corneum 211 has some disadvantages since care has to be taken to avoid infections.

The third crater 230 is typical of a new type of craters. The third crater 230 is optionally produced by a high temperature tip made from a low heat conductivity metal such as stainless steel, which may be gold plated for biocompatibility purposes. In comparison to the second crater 220, the third crater 230 is produced with a skin contact time duration which is typically shorter, delivering less heat than required to vaporize a large volume of the skin 200, optionally due to low thermal conductivity of the metal. Protrusion of a tip array from a distal end plate such as depicted by reference 118 in FIG. 1A is optionally controlled such that the high temperature tip pushes the skin 200 with some force F. As a result, the skin 200 is compressed without an explosive vaporizing effect which might destroy or ablate the stratum corneum 211, and heat may optionally flow through epidermis 214, to a selected, controlled, depth, such as down to the papillary dermis. The inventors believe that produced vapors may expand internally toward the dermis and may produce microchannels in the epidermis. The depth potentially depends on skin contact duration, advance velocity U, tip protrusion, and tip temperature as well as on a potential skin bulging into a distal opening of a treatment hand-piece. For example, a stainless steel tip at 400 deg C., contacting the skin 200 for 9 milliseconds in a single pulse, with a protrusion of 350 microns, will typically produce a conical crater of ~100 micron depth, potentially sized similarly to the second crater 220. However, the stratum corneum 211 is not ablated, and will typically be compressed on the third crater 230 bottom, serving as a natural barrier to the wound and potentially assisting in avoiding infections.

In some embodiments conditions for non ablation of the stratum corneum during skin thermal compression include a utilization of a low-thermal-conduction pyramidal tip such as a gold coated stainless steel (thermal conductivity ~20 W/degrees C. cm) and a short skin contact duration (less than or equal to approximately 9 milliseconds) and a tip temperature of approximately ~300-350 deg C. as well as a sharp (~100 microns in diameter) pyramidal or conical tip. It is noted that in some embodiments, in order to preserve the stratum cornea, the generation of vapors is optionally done so as to produce a low pressure, to overcome a potential crater sealing effect by the tips.

It is noted that a metallic tip or rod at room temperature (such as a distal end of a fork) may also generate a depression in skin if pushed against the skin. However, the depression will disappear within a short time, such as seconds, due to skin flexibility once the fork is removed. A high temperature tip such as in example embodiments, for example a temperature of above 200 degrees C., heats tissue down to a depth which depends on a heat diffusion constant of tissue and on skin contact duration. During the duration the skin is locally compressed. A denaturation of collagen due to heat potentially damages skin flexibility and enables a crater to remain compressed until healing, as in the case of the third crater 230. An end result is a fractional skin resurfacing tool which is highly controlled and lets the stratum cornea be pushed against a crater bottom and serve as a natural bandage.

Reference is now made to FIGS. 3A, 3B and 3C, which are images of three histology cross sections of three skin craters produced by three methods.

FIG. 3A depicts a histology cross section of a human skin crater produced by a $CO_2$ fractional skin resurfacing laser.

FIG. 3B depicts a histology cross section of a human skin crater produced by a vaporizing high temperature pyramidal tip at 400 deg C. according to an example embodiment of the invention.

FIG. 3C depicts a histology cross section of a human skin crater produced by a non ablative thermal compression pyramidal tip at high temperature according to another example embodiment of the invention.

FIGS. 3A, 3B and 3C depict crater histology cross sections produced by each of the above-mentioned methods.

FIG. 3A shows a histology cross section with a crater 310 in skin 300 obtained with a Quanta laser (Fractional $CO_2$ laser, "YouLaser", Quanta, 24W, 750 μsec, 2 stacks, density 100, 36 mJ/point).

FIG. 3B shows a histology cross section with a crater 320 in the skin 300 obtained with a stainless steel pyramidal tip. The crater 320 is smaller in diameter than the laser crater 310 of FIG. 3A, and collateral thermal damage in a horizontal direction is smaller than in the laser crater 320.

FIG. 3C shows a histology cross section of a thermally compressed crater 330 similar in size to the crater 320 of FIG. 3B. However, the crater 330 includes a stratum corneum cover to the crater 330 which is at least partly not vaporized and may potentially serve as a protective layer against infection. Treatment parameters used for producing the crater 330 include using a double heat pulse obtained by a gold coated stainless steel pyramidal tip in contact with the skin 300 for a duration of 9 milliseconds.

Thermally Compressed Craters and Skin Permeability

Figure 4A:
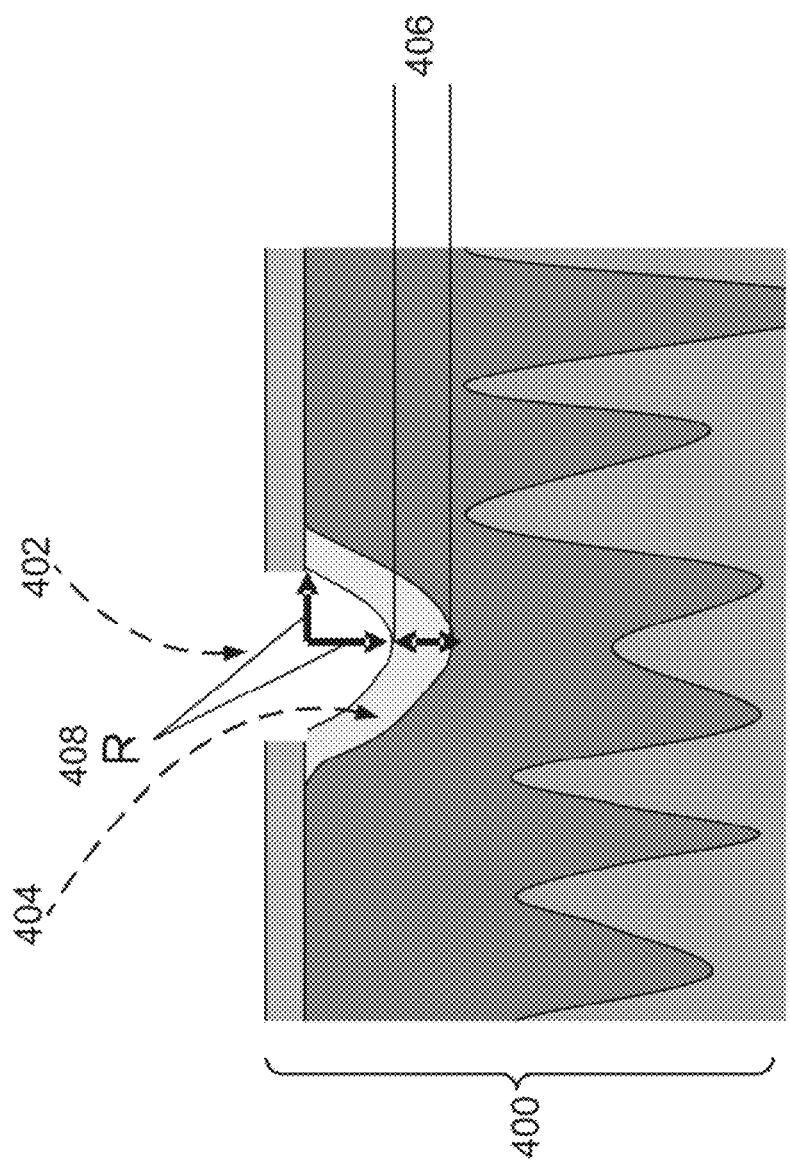
FIG. 4A is a simplified line drawing illustration of a thermally compressed crater in skin, produced according to an example embodiment of the invention.

Reference is now made to FIG. 4A, which is a simplified line drawing illustration of a thermally compressed crater 402 in skin 400, produced according to an example embodiment of the invention.

FIG. 4A depicts the crater 402 with a damaged layer 404 which potentially provides enhanced skin permeability to certain drugs (such as hydrophilic drugs) as compared to non treated skin. The type of damage may be necrosis, partial coagulation, or dystrophic vacuole alterations—a phenomenon of keratinocyte suffering which is smaller than necrosis.

In an embodiment of the invention, production of a crater by thermal compression of skin is utilized in order to enhance skin permeability to a variety of drugs or creams as compared to untreated skin. While utilizing example gold coated stainless steel sharp (~100 micron distal width) pyramidal tips, with ~300-500 micron protrusion from a treatment hand-piece, and a pulse duration of 6-9 milliseconds, craters have been produced which are depicted in FIG. 4C (in vivo human skin) and FIG. 4B (in vitro pig's ear skin), which are described below.

Figure 4B:
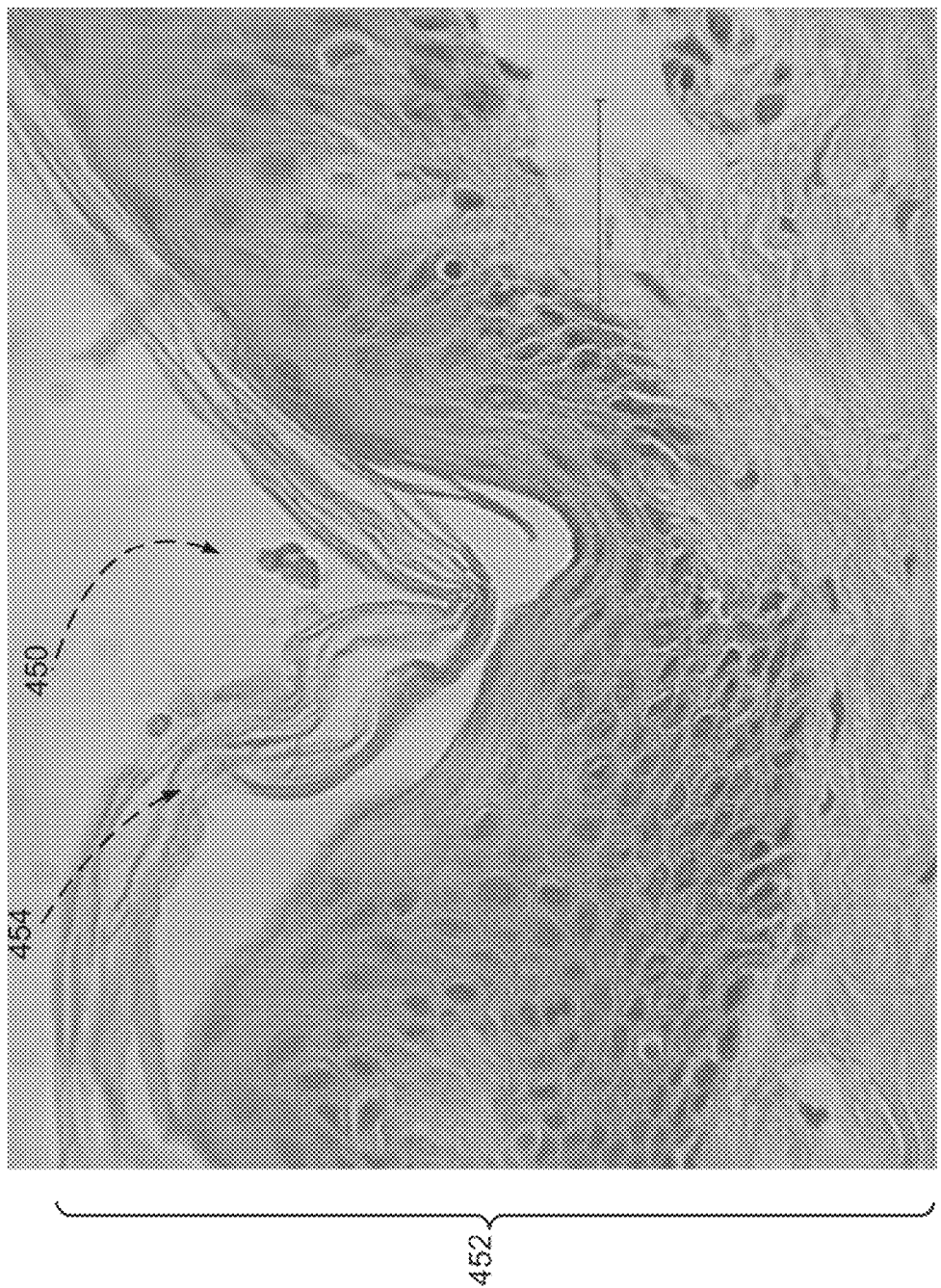
FIG. 4B is a histology cross section of a thermally compressed crater in skin, produced according to an example embodiment of the invention.
Figure 4C:
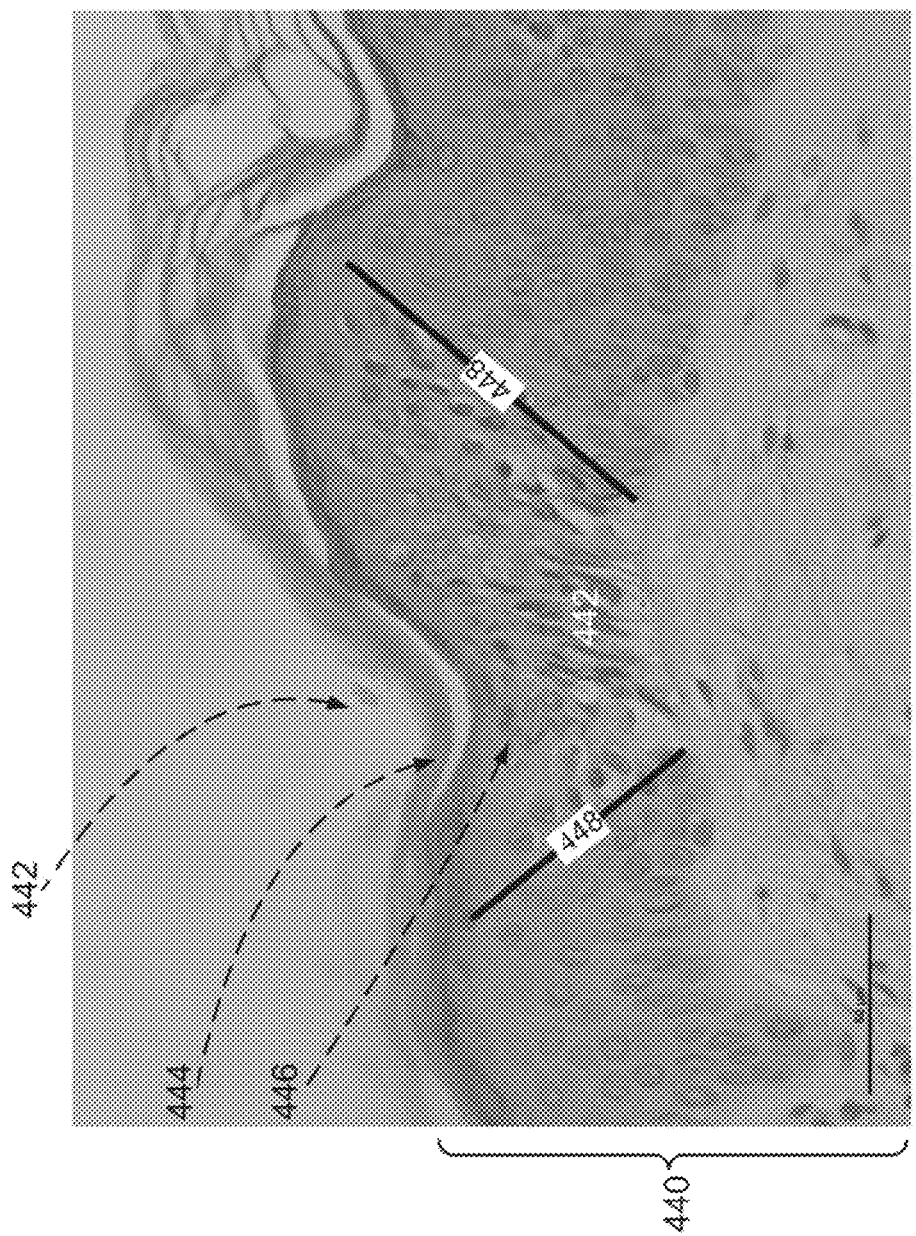
FIG. 4C is a histology cross section of a thermally compressed crater in skin, produced according to an example embodiment of the invention.

Reference is now made to FIG. 4B, which is a histology cross section of a thermally compressed crater 450 in skin 452, produced according to an example embodiment of the invention.

FIG. 4B depicts pig ear skin 452 and a crater 450 which was produced by thermally crushing the skin 452. The crushing was produced by a gold coated stainless steel tip (sharp, 100 micron distal diameter) pressed into the skin 452 for a duration of 9 milliseconds. A stratum cornea layer 454 of the skin 452 is present, and is functionally damaged from a standpoint of skin permeability to some drugs. The depression of the crater 450 is a lasting depression, potentially lasting over hours and days, due to loss of elasticity of the upper skin which is believed to be caused by denaturation of proteins. It is noted that even a partial denaturation will induce a loss of elasticity—there is no need for necrosis. The loss of elasticity may also be caused by a production of microchannels following vapor explosion. It is believed by the inventors that the hot tip which is in contact with the skin serves at least partially as a seal for the crater, which potentially prevents at least some of the vapor from escaping out of the skin, potentially resulting in a creation of channels in the epidermis. This belief appears to be supported by the fact that vapors are not seen during application of the tip, as opposed to vapors and smoke which are seen during laser treatments. The above explanations of potential mechanisms for producing a lasting depression and an improvement in drug delivery are not meant to limit the scope of the invention.

Testing skin permeability through skin 452 treated to produce craters such as the crater 450, over a period of 24 hours with a Franz diffusion cell, for the drug verapamil hydrochloride (1%), reveals that the skin permeability dramatically increases by approximately ×10-×30 as compared to non treated skin.

Similar results were obtained in testing a sample of additional four in vitro skins.

Figure 18:
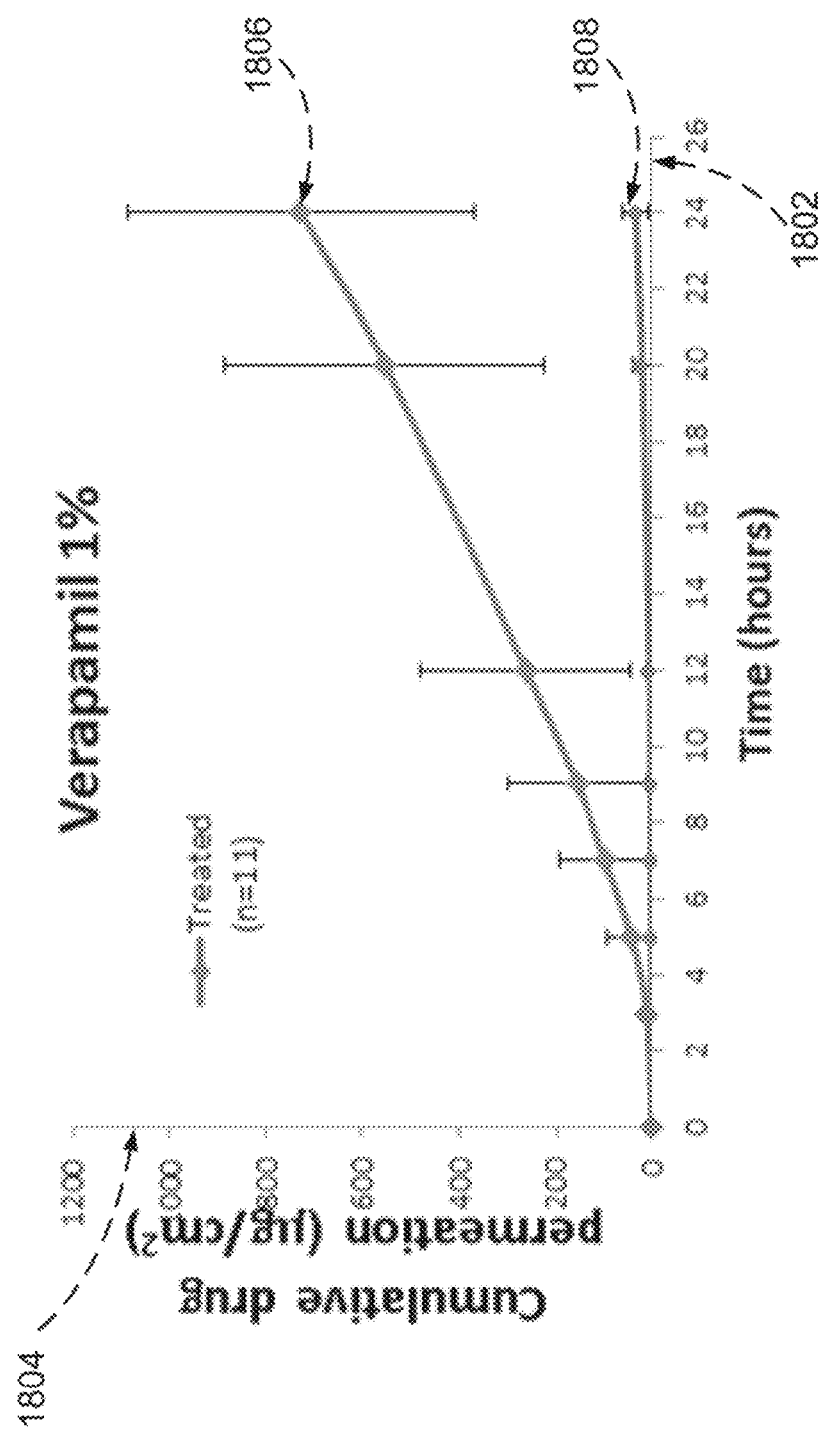
FIG. 18 is a graph showing experimental results of measuring skin permeability for a drug according to an example embodiment of the invention.

Reference is now made to FIG. 18, which is a graph 1800 showing experimental results of measuring skin permeability for a drug according to an example embodiment of the invention.

The graph 1800 has an X-axis 1802 showing time in hours, and a Y-axis showing cumulative drug permeation on micrograms per square centimeter of tested skin.

FIG. 18 depicts a first line 1806 showing average treated skin permeability as function of time, for a duration of up to 24 hours, and a second line 1808 showing average treated skin permeability as function of time for untreated skin. It is apparent that the thermally depressed skin is transmitting drugs although epidermis has been altered.

Reference is now additionally made to FIG. 4C, which is a histology cross section of a thermally compressed crater 442 in skin 440, produced according to an example embodiment of the invention.

The skin 440 in FIG. 4C is in vivo human skin.

FIG. 4C depicts a compressed crater 442, a section of detached stratum cornea 444 which is damaged, and a zone 446 with dystrophic vacuole alterations which is about 50 microns deep. A trapezoid shaped zone between two lines 448 includes a zone with micro-channels 450 which are not present in the surrounding skin 440.

As can also be seen, cells along the microchannel direction are squeezed and not rounded. They have lost their shape, as a result of elasticity loss which may be associated with protein disruption.

For selection of operating parameters which potentially lead to production of thermally compressed craters such as the crater 402 depicted in FIG. 4A, a crater is described as having approximately a diameter 2R, a depth R 408, and a collateral thermal dystrophic vacuole alteration zone 406 of depth R. For example, 2R is chosen to be 100 microns, crater depth is therefore R 408 is approximately 50 microns, and the dystrophic vacuole alteration zone depth 406 is 50 micron as well. During a process of thermal compression skin is believed to stretch as long as temperature does not attain a temperature which leads to at least partial denaturation of collagen, temperature is close to 60 degrees C., that is, collagen is still elastic.

Depth Control Based on Knowledge of Mechanics of Skin Compliance

An aspect of some embodiments of the invention relates to vaporization of tissue located on top of hard tissue. Some examples of such conditions include facial skin located below the eyes (such as lower eyelids), forehead skin, and palm skin. In the listed cases underlying bone is close to the skin layer, the distance between them being between approximately 1 mm and approximately 4 mm, depending on gender, age, and precise location on the body.

When advancing a vaporization tip toward a skin surface such that the tip is brought into contact with the skin, and further advancing beyond the skin surface, the skin mechanical impedance may potentially negatively affect the clinical result of such an advance, as explained below. This effect is particularly pronounced when bone structures are located close to the skin. The problem is now illustrated with the aid of FIGS. 5A-5D.

Reference is now made to FIG. 5A, which is a simplified line drawing illustration of a device 500 for skin treatment according to an example embodiment of the invention.

Reference is additionally made to FIGS. 5B-D, which are simplified line drawing illustrations of the device of FIG. 5A, pressed against skin in an example embodiment of the invention where distance from skin surface to underlying bone is small.

FIG. 5A depicts a schematic presentation of a device 500. The device 500 includes an array of tips 502, which are heated to a temperature of approximately 200-600 deg C. A width of the tips array is depicted as D 504. D 504 typically ranges between approximately 2 mm-20 mm. D 504 may preferably be 10 mm. The device 500, which may be a treatment hand-piece, is placed on a skin surface 506. The array of tips 502 is advanced toward the skin surface 506, and optionally set to protrude a distance Y 508 from a distal end 510 of the device 500. The device 500 optionally vaporizes a crater array to a depth of X 512. The protrusion Y 508 is sometimes useful even in case of a flat skin surface 506, and is at least equal to X 512. However, in many cases skin is slightly bulging 516 toward the device 500. The bulging distance S 516 varies according to skin flexibility, according to pressure applied on the skin by operator. S 516 is proportional to R ^ (2~4), where R 518 is the opening diameter R of the distal end of the device 500. The bulging distance S 516 may be typically 300-1000 microns. For example, if S 516 is larger than the vaporization depth (such as in a case of the skin bulging 1 mm and the vaporization depth being 100 microns), the array of tips may optionally push the skin a distance larger than vaporization depth.

In some embodiments the advance of the array of tips 502 is optionally produced by an advancing mechanism such as, but not limited to, an electrical motor 520, which may be a linear motor or a rotary motor. Advancing motion parameters such as, by way of some non-limiting examples, speed U 522, acceleration, amplitude, and tip protrusion, are optionally controlled by parameters such as current i or voltage V supplied to the motor.

A value of crater depth X may be 20 microns to 200 microns, typically 50-100 microns. The protrusion Y 508 may be selected as approximately 200-2000 microns, typically 400-700 microns, over a duration of 0.1-20 milliseconds, typically over a duration of 3-9 milliseconds.

While testing devices produced according to some embodiments of the invention, the inventors discovered that if the array of tips 502 is advanced too fast and/or too far within too short a duration on skin over a "bony zone", such as depicted by reference 511 in FIGS. 5A, 5C and 5D, an impact was felt by a treated patient, pain was substantial, and treatment results were sometimes unsatisfactory. It is advantageous to control vaporization depth under these circumstances, without causing pain to the patient, by monitoring skin properties and rapidly modifying treatment parameters accordingly.

According to some embodiments, the treatment method and parameters are optionally modified to allow skin to be compressed during the advance of the tip array when in contact with tissue and not allowed to advance if skin becomes rigid due to its viscosity. This method is explained below.

A case is taken, for example, in which an advance velocity U 522 of the array of tips 502 is more rapid than a speed of a vaporization front along the crater axis for achieving a vaporization of a crater of depth X 512. In such a case tissue is pushed forward during the tip advancement. Moreover, if a protrusion Y 508 is set to be greater than a desired crater depth X 512, such as for example X=50 microns, Y=500 microns, the array of tips 502 may move a long distance without substantially increasing crater depth. In such a case, the array of tips 502, which have an area of 1 cm×1 cm, for example, compresses skin fluids away from a gap between the skin surface 506 and the bone surface to adjacent areas. However, the viscosity of the skin fluids may prevent this outward expulsion of fluids if distance Z 524 between bone and skin surface is small such as approximately 1-3 mm. As is explained below with reference to FIGS. 5C and 5D, a computation of impedance caused by skin viscosity is optionally modeled using a theory of viscous lubrication of moving surfaces, such as described in above-mentioned text book chapter found on the World Wide Web at wwwf(dot)imperial(dot)ac(dot)uk/~ajm8/M3A10/lub(dot)pdf and the model may optionally be used in order to control and reduce negative effects on treatment. Such control is an aspect of some embodiments of the invention.

Referring now to FIGS. 5C and 5D, since depth of vaporization is X 512 (FIG. 5A), since X<Y, and since skin will be pushed toward bone structure a distance of Y−X in order to advance a distance Y beyond the skin surface plane, a volume of tissue of approximately D×D×(Z−X) is displaced horizontally, as depicted in FIG. 5D. Since skin does not significantly bulge between the tips in a tip array if the distance between the tips is small, such as approximately 1 mm, the model of a lubricating viscous liquid (tissue) between two horizontal planes which are approaching each other at a relative velocity U 522 and squeezes the lubricating liquid out from the volume between the planes can be applied to the scenario of an advancing array of tips.

We now provide an equation which assists in estimating and quantitatively controlling the protrusion level Y desired in order to optionally avoid pain or other possible adverse effects, when the distance Z 524 of bone from skin surface is small.

While a plate 530 which represents the distal plane of the array of tips 502 in FIG. 5A, is moving at velocity U 522 and squeezing out viscous liquid 532 representing tissue, the squeezed volume is approximately $Y*D^2$. The velocity U 522 is approximately $Y/t$, where t is a duration of the forward movement of the tips when beyond the plane of the skin surface 506. The plate 530 is optionally pushed with a force F, generated by the motor 520. A resulting pressure P 534 at a location of a middle point A 536 is approximately $P=F/D^2$. The pressure at the edges of the plate 530 is approximately that of ambient liquid (body) pressure. The pressure differential causes the liquid to be squeezed out.

An approximate rate $Q=Y*D^2/t$ of material squeezing between two parallel plates is given by:

$$Q \sim c*P*Z^3/(12*\mu) \qquad \text{Equation 1}$$

Where $\mu$ is a liquid (tissue) viscosity and c is a constant. Equation 1 entails:

$$P=k*Q*\mu/Z^3=k*Y*D^2*\mu/t*Z^3 \qquad \text{Equation 2}$$

where k is a constant.
Furthermore, the driving force:

$$F=k*Y*D^4*\mu/t*(Z^3) \qquad \text{Equation 3}$$

In some embodiments Equation 3 serves as at least a partial guide for setting control of a driving force by the motor 520. It is noted that additional parameters may affect skin compliance as a function of tip velocity, such as, by way of a non-limiting example, skin surface elasticity. However, Equation 3 enables to quickly set a good order of magnitude for treatment parameters, for example as a function of a distance from bones, and further method steps potentially enable improved settings.

In controlling the driving force of the array of tips one or more of the following considerations are optionally used:

a) F increases as an inverse third power of the distance Z. For instance, if a force $F_0$ is applied during a procedure of fractional vaporization of craters on cheeks, with a protrusion distance of 1000 microns, where Z~10 mm, the force used to optionally obtain similar results close to eyelids, where Z~2 mm, is $5^3=125$ times larger. This force might generate a painful blow. By reducing the protrusion by ⅓ (to ~330 microns), as well as by increasing the duration of advance by a factor of 2, optionally by reducing the velocity U, a force reduction of X6 is obtained. The inventors have tested the above conditions and discovered the results painless and satisfying. Thus Equation 3 optionally serves as a useful guide in setting motor operation and protrusion parameters.

In addition, in order to further refine the control parameters, the distance Z of bone from skin surface may be measured, for example by pressing the skin with a micrometer, or with use of an ultrasound unit, and the results may be input to a data table.

b) F dramatically increases with D ($D^4$). This means that by decreasing a total area of the array of tips by a factor of 2, the force F is reduced by a factor of 4. This means that a utilization of smaller arrays of tips on bony structures provides an advantage. As a result, control of treatment conditions may also include an instruction to a practitioner to change an array of tips as a result of skin mechanical resistance to movement.

c) Dependence of F on viscosity $\mu$ is low (linear). As a result, the control equations depend less on a precise value for skin viscosity, and in some embodiments a universal value of viscosity may be used for all or almost all patients.

In some embodiments the control of F or of the protrusion level Y or of other treatments parameters as described above may be based on open loop control methods and/or on closed loop control methods. Descriptions of embodiments of both types of control methods are described below.

Open Loop Control

Figure 6:
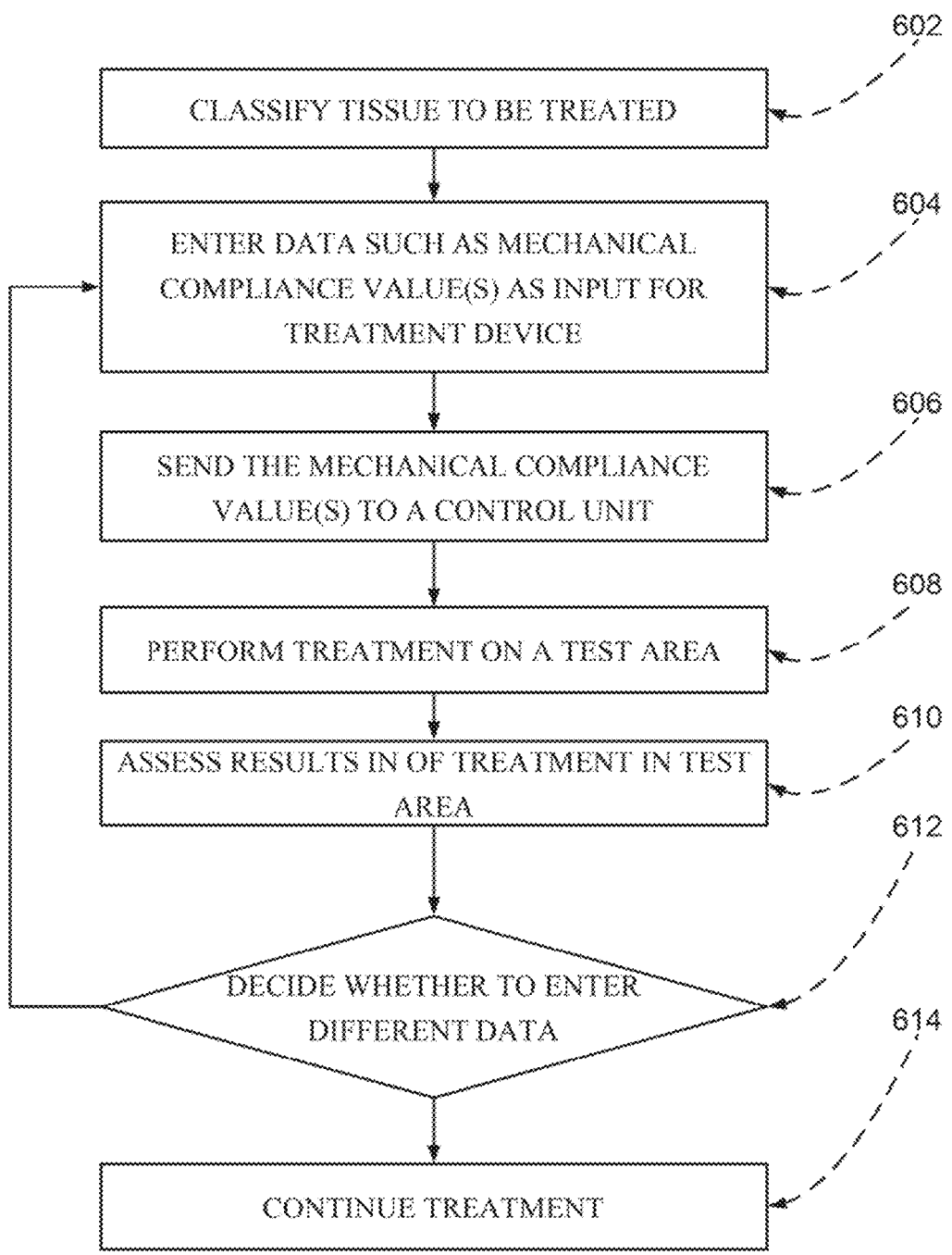
FIG. 6 is a simplified flow chart illustration of an open loop control method of selecting treatment parameters according to an example embodiment of the invention.

Reference is now made to FIG. 6, which is a simplified flow chart illustration of an open loop control method of selecting treatment parameters according to an example embodiment of the invention.

The example method of FIG. 6 includes:

Classifying tissue to be treated (602). In some embodiments the classifying includes determining a type of tissue to be treated, such as "over bone", eyelids, forehead, and so on. In some embodiments classifying includes assessing mechanical compliance of tissue In some embodiments the assessing includes an operator optionally pressing the skin on an area to be treated, such as, by way of some non-limiting examples, eyelids, forehead and so on, and categorizing the tissue according to his own judgment as, by way of some non-limiting examples, thin skin, bony area, and so on. In some embodiments the mechanical compliance of tissue is input as levels in a scale, such as a scale from 1 to 5.

In some embodiments an operator evaluates a distance which the operator's finger advances before encountering rigid tissue. By way of a non-limiting example, a distance of ~1 mm may optionally correspond to compliance of level 5, while a distance of 10 mm corresponds to compliance of level 1. In some embodiments the classifying includes using ultrasound to assess the mechanical compliance of the tissue, for example by measuring the depth from tissue surface to bone.

Entering data such as the one or more mechanical compliance values as parameters to an input unit in a tissue treatment device constructed according to an example embodiment of the invention (604). An example treatment device control panel may include a touch screen which poses a question about skin mechanical features. The entering of data may include any one or more of the values collected in while classifying the tissue.

Sending the one or more values to a control unit (606). The control unit may include a microprocessor, which may be input the compliance values. The microprocessor may also be provided with a table which translates skin compliance input into motor control parameters which may include motor current, motor voltage, limiting parameters such as at what distance and/or time to stop, and/or tip protrusion, and/or temporal behavior of the advancing and retracting motion. The translation may optionally be performed by using Equation 3, either to set up a translation table, or to calculate parameters based on input. In some embodiments the translation includes correcting initial parameters input by device producers based on typical results obtained in clinical studies. In some embodiments the control unit optionally recommends what size and/or geometry and/or type of array of tips should be used. In some embodiments the device optionally changes the array of tips automatically, as will be described below. In some embodiments the translation is dynamically adjusted according to data accumulated on skin resistance. In some embodiment the translation is optionally based on data accumulated on skin resistance to tip movement at low velocity U and an extrapolation to higher velocities and/or shorter duration, optionally using Equation 3.

Performing treatment on a test area of skin (608).

Assessing results of treatment in test area (610).

Deciding whether to enter different data as described above in (604) based on the assessing (612).

Optionally continuing treatment on an additional area of skin (614).

It is noted that clinical tests performed by the inventors on patients have revealed that an open loop setting method of setting treatment parameters according to mechanical skin classification by tactile feedback considerably improves results and eliminated pain.

Figure 7:
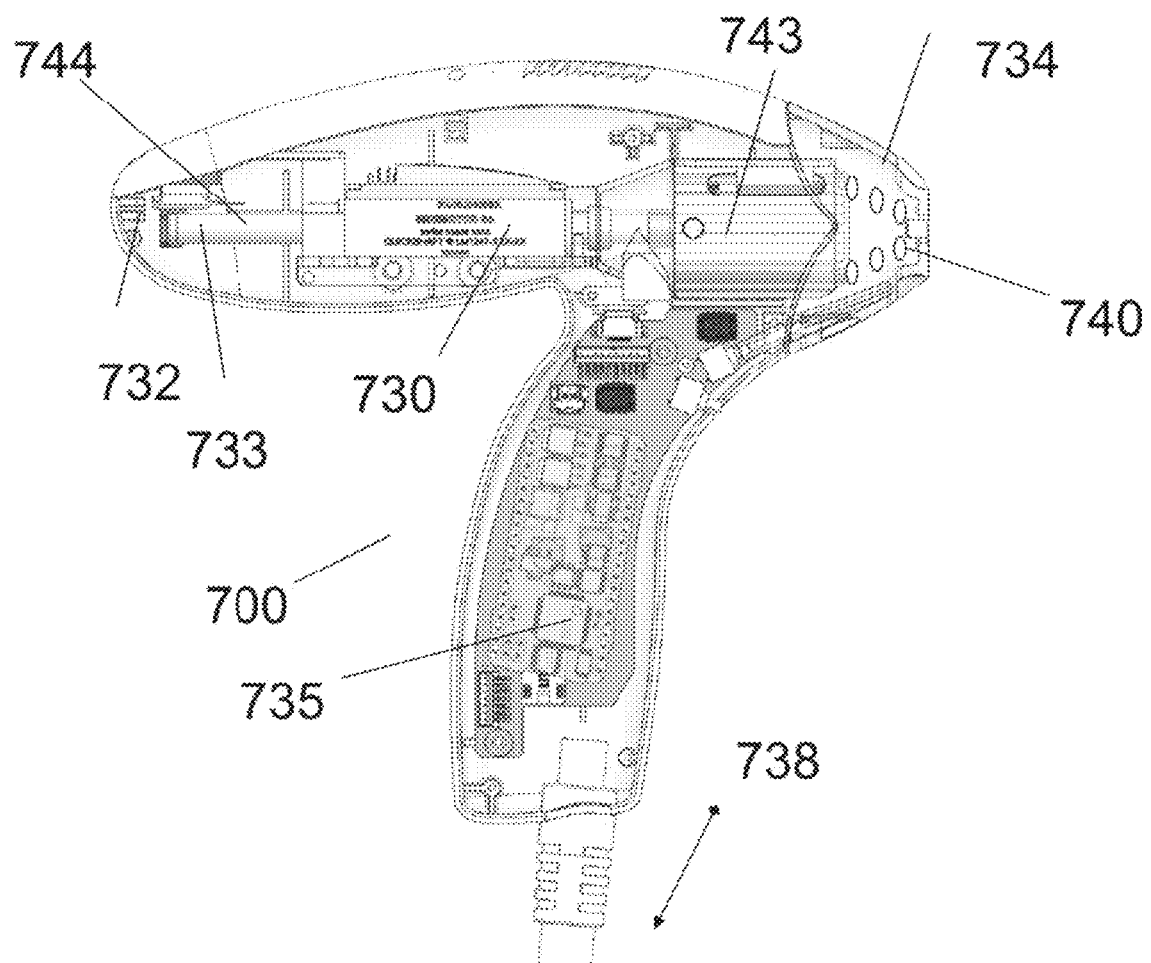
FIG. 7 is a simplified line drawing illustration of an example embodiment of a tissue treatment hand-piece according to an example embodiment of the invention.

Reference is now made to FIG. 7, which is a simplified line drawing illustration of an example embodiment of a tissue treatment hand-piece 700 according to an example embodiment of the invention.

FIG. 7 depicts the treatment hand-piece 700, designed to vaporize craters in tissue using a linear motor 730, such as produced by Faulhaber Minimotor SA, Switzerland. The linear motor 730 is located in the treatment hand-piece 700, which also includes a position encoder 732. The position encoder 732 optionally provides information enabling a calculation of a position of a rod 733, which is driven by the linear motor 730, relative to a reference plane. Extending the rod 733 pushes a heater and treatment pins (not shown in FIG. 7) toward skin and back from the skin. A distal cover 734 is optionally placed on skin. The distal cover 734 may optionally be transparent, optionally providing a good view of a treatment site, and may optionally incorporate holes in order to enable suction of air from a treatment site into the hand-piece 700. The position encoder 732 optionally provides a position accuracy on the order of 1 micron, and may be a magnetic array type encoder (such as a magnetic type encoder produced by Texas Instruments, USA), or an optical encoder or a Hall effect detector.

In some embodiments the linear motor 730 is optionally operated at a constant voltage and the force applied by the linear motor 730 on the tip array is optionally controlled by a controller 735 by modulating width of pulses applied to the linear motor 730 (Pulse Width Modulation=PWM). A velocity of the rod 733, which is equal to the tip velocity, is optionally monitored by monitoring a time derivative of the rod 733 position. Following advance toward tissue and upon contact with treated tissue, the velocity of the rod 733 may be reduced, optionally in cases where it is know that skin mechanical compliance is low. As described above, skin mechanical compliance depends on tip array protrusion and/or distance of bone under the skin, among other considerations. Once velocity reduction, caused by the array of tip pressing against skin, is detected, the controller 735 optionally modifies the width of pulses applied to the linear motor 730, optionally so that original velocity is restored.

In some embodiments, the protrusion of the tip array may also be modified according to the skin mechanical compliance. Modifying the position is possible since the position of the rod 733 is known, optionally even with 1 micron accuracy. As a result, a closed loop method enables a vaporization of craters with high depth accuracy on the order of a few microns regardless of tissue type, by measuring protrusion.

In some embodiments an automatic control of side effects such as pain due to mechanical impact and/or injury is potentially obtained based on controlling depth. Since it is believed that there is a relation between mechanical skin compliance and clinical side effects, controlling depth instead of trying to achieve a desired depth using open loop control may potentially reduce pain.

Closed Loop Control

Figure 8A:
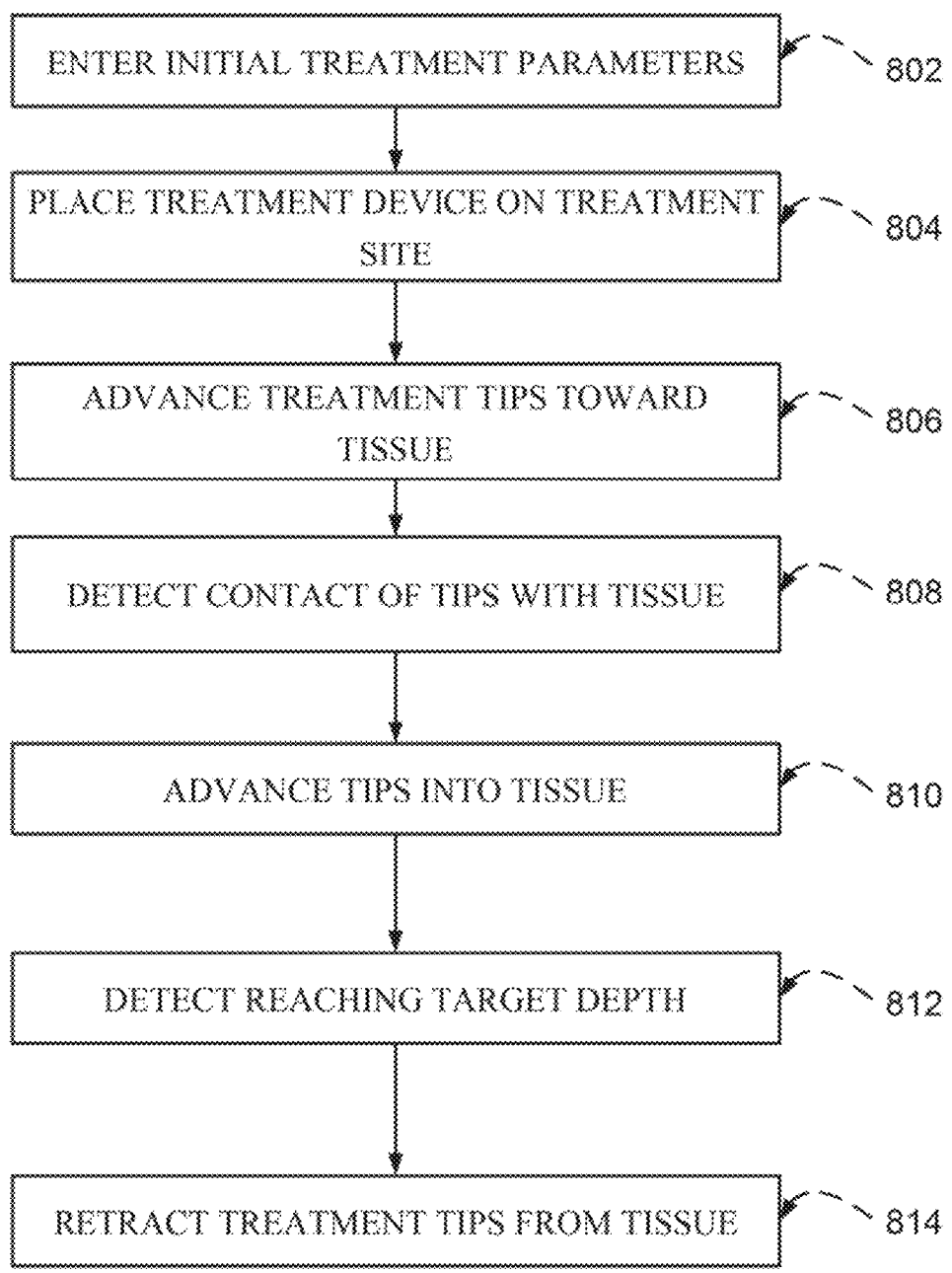
FIG. 8A is a simplified flow chart illustration of a method of producing craters in tissue according to an example embodiment of the invention.

Reference is now made to FIG. 8A, which is a simplified flow chart illustration of a method of producing craters in tissue according to an example embodiment of the invention.

The example method of FIG. 8A includes:

Optionally entering one or more initial treatment parameters (802) such as, by way of a non-limiting example, type of tip array, area of tip array, duration for tips to press against tissue, depth to which tips should press into tissue, protrusion of tips from end plate, and so on, as input into a treatment device.

Optionally placing the treatment device on a treatment site (804). Optionally, the placing includes placing an end plate of the treatment device directly against skin.

Advancing treatment tip(s) or array of tips toward tissue (806).

Detecting contact of tips with tissue (808). It is noted that skin may bulge through an opening in the end plate, or that skin may not lie flat against the end plate, so that contacts of the tips with tissue does not necessarily happen immediately when the tips protrude from the end plate.

Advancing tips into tissue (810). In some embodiments the distance advanced into tissue is measured by an encoder measuring a distance advanced following detection of contact with tissue. In some embodiment, a motor driving the tip advancement optionally acts to maintain a constant advancement speed, optionally using a closed-loop method of control over the speed. In some embodiments the motor driving the tip advancement optionally acts to maintain a constant force against the tissue. In some embodiments, the motor driving the tip advancement optionally acts to maintain a force no greater than a specific threshold force against the tissue.

Detecting reaching a target depth into the tissue (812).

Retracting the treatment tip(s) from the tissue (814).

In some embodiments the treatment tip is optionally left at the target depth into the tissue for a specific period of time (not shown in FIG. 8A).

In some embodiments, the tissue or skin may be a thin layer over bone, in which case producing a crater in the skin to a target depth has a potential to cause pain.

In some embodiments, the above-described method is used to advance tips into tissue. When the tips advance into the tissue, the tissue impedance is measured, and provided as data upon a control and/or input display of the treatment device. The measured tissue impedance device may then optionally be fed, manually or automatically, into the treatment device.

In some embodiment a new treatment may be carried out at the same treatment site or at a nearby treatment site, using the measured tissue impedance.

In some embodiments the measured tissue impedance is optionally used as feedback to determine treatment parameters during a single treatment.

Figure 8B:
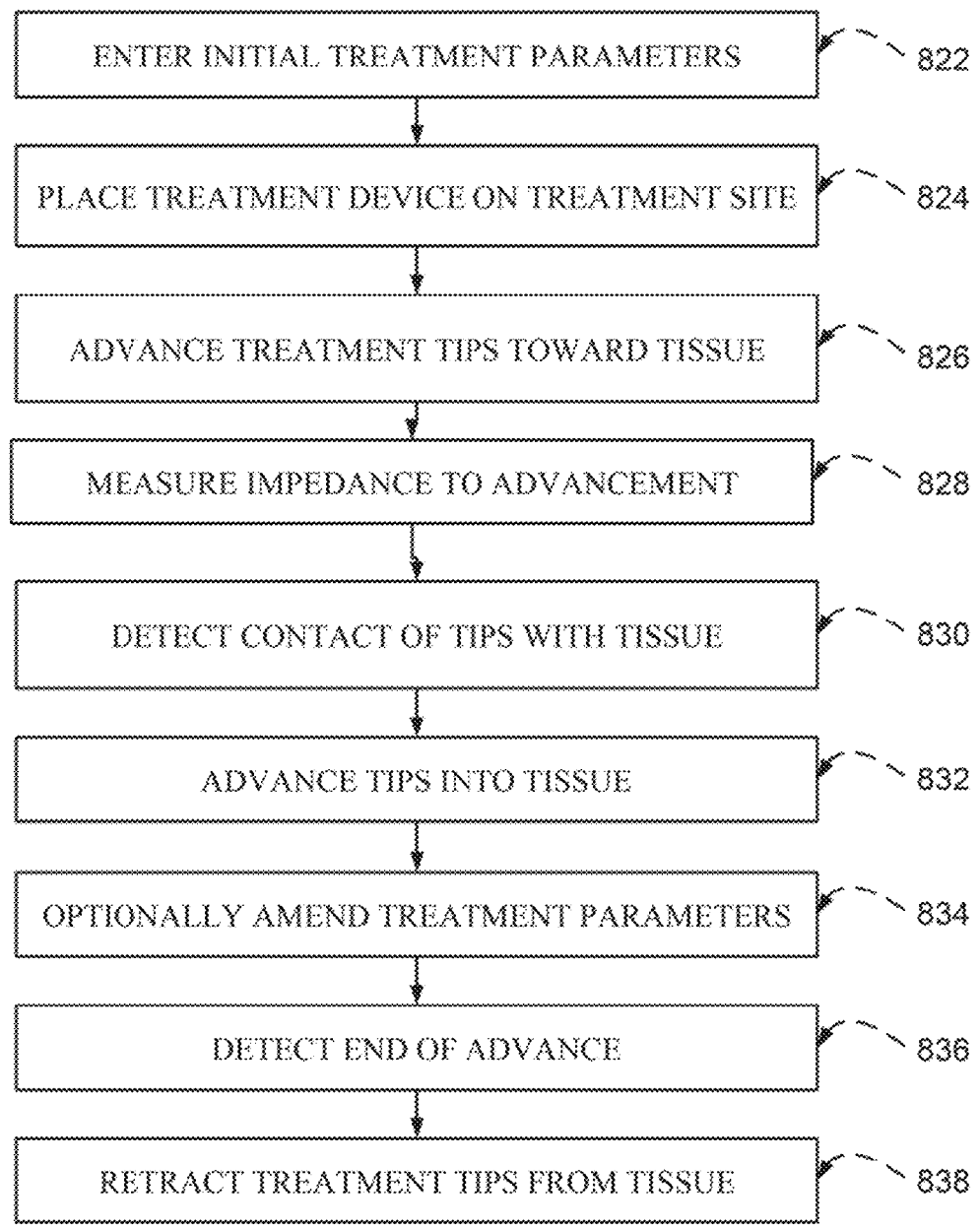
FIG. 8B is a simplified flow chart illustration of a method of producing craters in tissue according to another example embodiment of the invention.

Reference is now made to FIG. 8B, which is a simplified flow chart illustration of a method of producing craters in tissue according to another example embodiment of the invention.

The example method of FIG. 8B includes:

Optionally entering one or more initial treatment parameters (822) such as, by way of a non-limiting example, type of tip array, area of tip array, duration for tips to press against tissue, depth to which tips should press into tissue, protrusion of tips from end plate, and so on, as input into a treatment device.

Optionally placing the treatment device on a treatment site (824). Optionally, the placing includes placing an end plate of the treatment device directly against skin.

Advancing treatment tip(s) or array of tips toward tissue (826).

Measuring impedance to the advancing of the tips (828).

Detecting contact of tips with tissue (830). It is noted that skin may bulge through an opening in the end plate, or that skin may not lie flat against the end plate, so that contacts of the tips with tissue does not necessarily happen immediately when the tips protrude from the end plate.

Advancing tips into tissue (832).

Optionally amending treatment parameters (834) based on the measured impedance.

Detecting end of advancement into tissue (836).

Retracting the treatment tip(s) from the tissue (838).

In some embodiments the measuring impedance to the advancing of the tips (828) is performed continually, both while the tips are not yet touching the tissue, and when the tips are moving into the tissue.

In some embodiments the amending treatment parameters (834) is optionally based on the measured impedance, and may optionally include several options:
- as long as the impedance does not exceed a threshold impedance force the advancement is continued up to a predetermined depth into the tissue.
- if the impedance exceeds a threshold impedance force, such as might happen in thin skin over bone, the advancement is stopped, so as to potentially prevent a sensation of pain by the patient, which may be associated with a force exceeding the threshold force.
- if the impedance exceeds a threshold impedance force, such as might happen in thin skin over bone, the treatment parameters are optionally changed, such as, for example, the depth of advancement into tissue is optionally changed to a smaller depth. In some embodiments, the treatment device optionally includes a conversion table which is used to convert an initial crater depth to a modified crater depth based, at least in part, on the measured impedance. In some embodiments, the treatment device optionally includes a calculation unit which uses Equation 3 above, or a similar equation, to recalculate crater depth so as not to exceed a threshold force.

In some embodiments of the invention, closed loop control of vaporizing depth and selection of tip protrusion relative to the distal gage 734 of FIG. 7 is optionally performed by controlling a single treatment pulse (pulse width modulation) on a selected area.

In some embodiments the method of FIG. 8B is used to measure mechanical compliance or resistance of the skin in a treatment site. This is optionally done by treating a small, for example 1 cm$^2$, area with a single advancement pulse of the treatment tips, and selecting a very shallow crater depth target. This pulse negligibly affects tissue. Once shallow target depth has been attained, skin compliance is measured by slowing the tip and measuring the current reduction necessary to reduce the speed as compared to a speed reduction for movement of the tips in air. Based on the measured skin compliance, automatic parameter correction is optionally performed. In some embodiments, there is no further need to continue activation of closed loop control. A corrected parameter may be for example a protrusion distance, which may be reduced if skin compliance is too low (a sign of skin being close to a bone). Another parameter which is optionally changed is skin contact duration, which may be reduced if compliance is low.

In some embodiments, closed loop monitoring of parameters according to skin mechanical compliance may lead to control of selection of size of tips array, optionally in accordance with Equation 3.

In some embodiments, the tip array is optionally located approximately 1 cm from tissue while in idle condition prior to triggering a treatment pulse. The offset distance from the skin is intended in order to potentially lower infrared radiation emitted from the high temperature array of tips (~400 deg C.) which may generate discomfort to a patient.

In some embodiments, the hand-piece 700 body of FIG. 7 is optionally chilled by air flow, which optionally flows in a direction away from the patient. Airflow is optionally controlled by a fan 737 (FIG. 7) and/or by an air pump 738 (not in FIG. 7) which may be located at an end of a hose. Holes 740 in the distal gage 734 optionally enable the air flow. An optional temperature sensor (not shown) optionally controls air flow and keeps the hand-piece 700 temperature at a reasonable level such as 35 deg C. The chilling flowing air optionally flows over an outside of a heat radiator 743, the radiator 743 surrounds a heater (not shown in FIG. 7), and conveys heat generated in the hand-piece 700 by the tip array heater and by an array of tips (not shown in FIG. 7) by radiation and/or conduction.

In some embodiments, electrical wires (not shown) connected to the heater and optionally moving with the heater are rigid. Flexible extension wires are optionally connected to the rigid wires and to the electrical supply of the heater.

In some embodiments, a safety spring 744 is located on the rod 733 and attached to the hand-piece 700, and optionally applies a restoring force F to the advancing tips when advancing toward tissue. The role of the spring 744 is to ensure lack of contact between the hot tip array and the skin in case of a failure of the electrical or control system. Upon any failure, electrical supply is optionally shut down and the spring 744 automatically retracts the high temperature array of tips away from tissue. In some embodiments the restoring force of the spring 744 is larger than required to lift a weight of the advancing parts in order to overcome even gravitation.

In some embodiments of the invention there is a warning element which indicates a type of skin which is highly compliant, or highly resistant such may occur over bones. The warning element may be, by way of some non-limiting examples, alight or an acoustic signal.

Closed Loop Depth Control in Compliant Skin

As explained above, in some cases of treatment skin may bulge into a treatment hand-piece. This is particularly true when skin is highly compliant, for example on cheeks. In such cases it is sometimes desirable to vaporize a crater to a controlled pre-specified depth and immediately retract the vaporizing tip array, avoiding additional forward movement intended to compress the skin.

In some embodiments, a closed loop control available while driving the motor 520 of FIG. 5A or the linear motor 730 of FIG. 7 enables achievement of the above objective. The rod 733 is initially advanced by the motor while the array of vaporizing tips is moving in air. This requires a force F which may vary over time, and may be optionally programmed into a controller.

Upon reaching contact with skin, mechanical resistance (or impedance) felt by the motor increases. The mechanical impedance produced by pushing against skin acts to reduce the velocity of the rod 733. Since the position encoder 732 is constantly measuring a position of the tips array, and monitoring velocity, the position encoder 732 detects the velocity slowdown. The controller 35 is optionally programmed such that upon detection of a velocity slowdown a command is provided to the motor to reverse motion direction.

Figure 16:
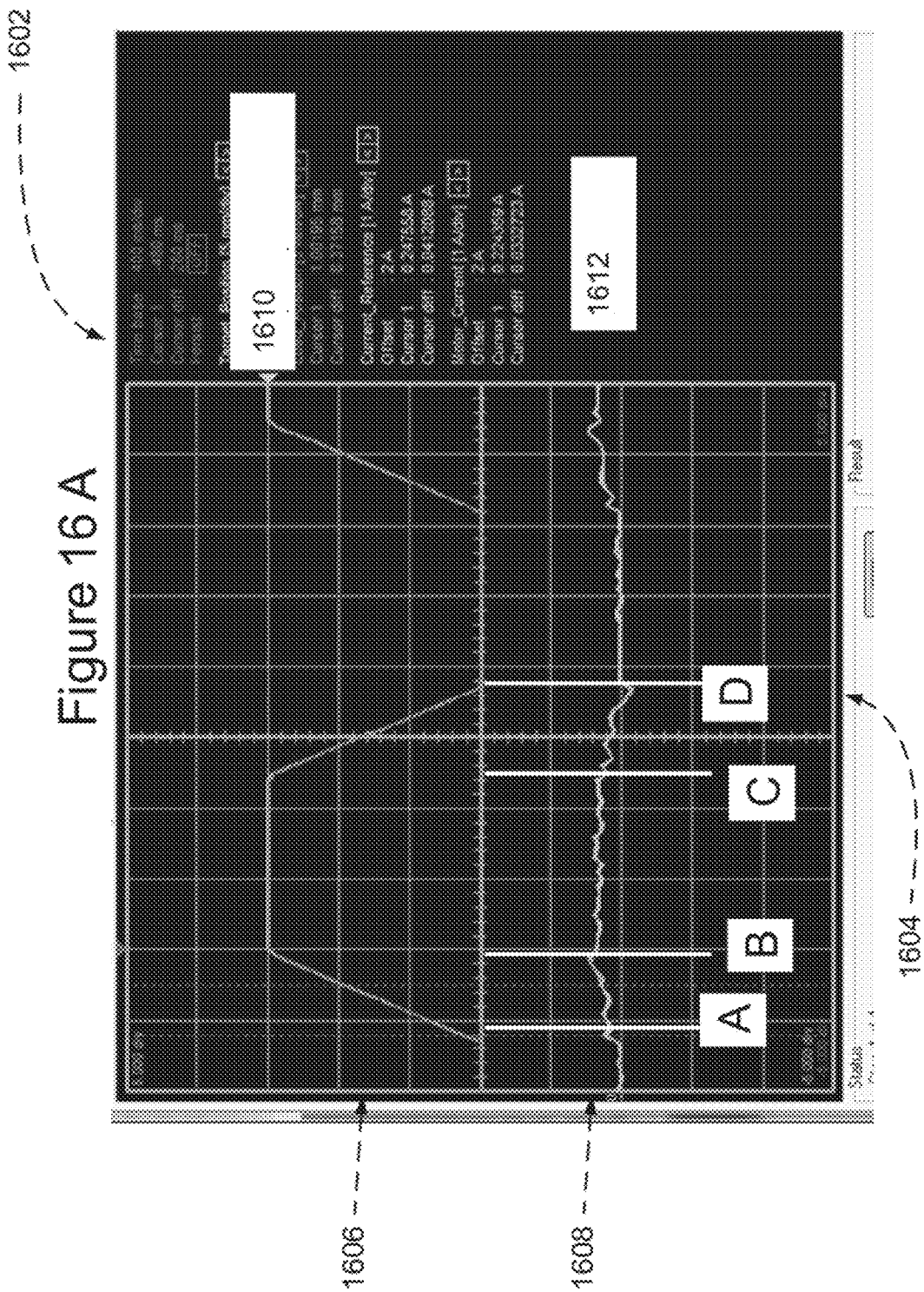
FIG. 16A is an oscilloscope trace of a position of an array of tips and of a driving current of a linear motor driving the array of tips in air according to an example embodiment of the invention.
FIG. 16B is an oscilloscope trace of a position of an array of tips and of a driving current of a linear motor driving the array of tips including a period of time touching impeding skin according to an example embodiment of the invention.

Reference is now made to FIG. 16A, which is an oscilloscope trace 1602 of a position of an array of tips and of a driving current of a linear motor driving the array of tips in air according to an example embodiment of the invention.

Figure 16B:
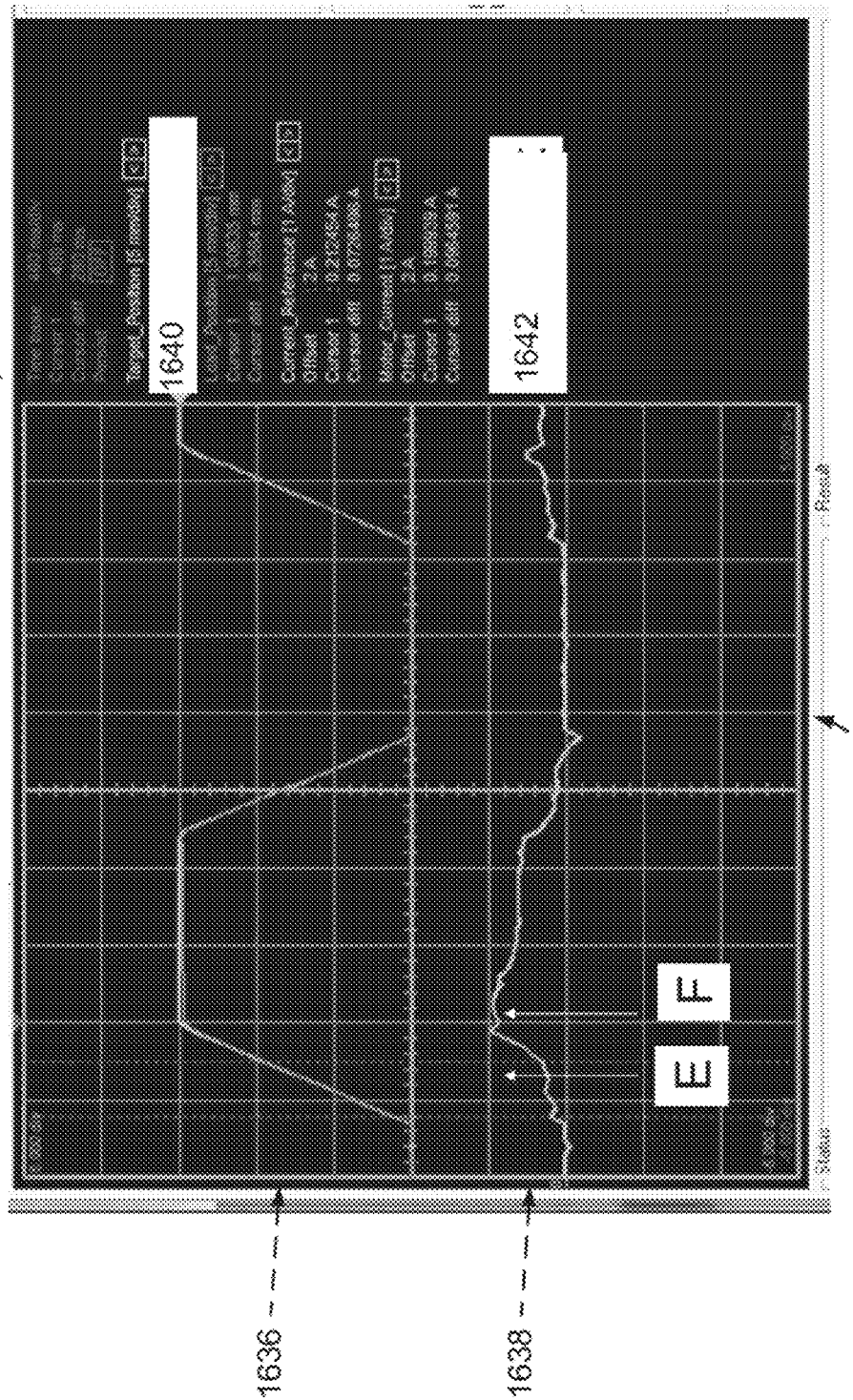

Reference is additionally made to FIG. 16B, which is an oscilloscope trace 1632 of a position of an array of tips and of a driving current of a linear motor driving the array of tips including a period of time touching impeding skin according to an example embodiment of the invention.

FIGS. 16A and 16B have X-axes 1604 1634 of time, 400 milliseconds per division and Y-axes of tip position 1606 1636, 5 mm per division, and driving current 1608 1638, 1 A per division, of a linear motor controlled using a closed loop control method of Pulse width Modulation (PWM).

FIG. 16A depicts an upper trace 1610 showing tip position as a function of time, with the tips moving in air. Section AB of the upper trace 1610 corresponds to the tips advancing, section BC of the upper trace 1610 corresponds to the tip at maximal advance, and section CD of the upper trace 1610 corresponds to a retraction phase of the tips.

FIG. 16A depicts a lower trace 1612 showing a driving current used to advance the tips. The driving current depicted by the lower trace 1612 appears substantially constant, barring noise artifacts. The driving current depicted by the lower trace 1612 corresponds to mechanical impedance to the tip movement by tissue—no skin contact.

FIG. 16B depicts an upper trace 1640 showing tip position as a function of time, with the tips moving into contact with tissue, in the example of FIG. 16B the tissue is the skin of a finger placed in the path of the tips. Section EF of the upper trace 1640 corresponds to the tips advancing into the tissue, and section GH corresponds to tip retraction.

FIG. 16B depicts a lower trace 1642 showing a driving current used to advance the tips. The driving current depicted by the lower trace 1642 appears shows a current increase in the section EF. The advancing tip came into contact with the skin at point E and gradually pushed the skin while compressing it. In the example embodiment depicted by FIG. 16B the tip speed is controlled to be constant, as mat be seen by the constant slope of the upper trace 1640 over the section EF. The driving current is proportional to the driving force, which is proportional to a resisting force in order to maintain the speed, and the resisting force is believed to be proportional to depth. The driving force and current reach a maximum at point F, which corresponds to the deepest depression. FIG. 16B shows a capability of detecting contact with skin as well as optionally determining a depth of depression based on force feedback which in some embodiments relates to the driving current.

The Array of Tips

Reference is now made to FIG. 9A which is a simplified line drawing illustration of an array of vaporizing tips according to an example embodiment of the invention.

Reference is also made to FIGS. 9B and 9C which are images of the example embodiment of FIG. 9A.

FIGS. 9A-9C depict an array of treatment tips which is coated or plated with a biocompatible material which is biocompatible when operating at high temperatures.

FIG. 9A depicts an array of vaporizing tips 902. The array of vaporizing tips 902 includes metallic pyramidal tips which may be produced by mechanical machining and/or by sintering. In some embodiments each pyramid base width is approximately half its height. A typical width may be 1250 micron while its height may be 2500 micron.

In some embodiments the pyramids are optionally truncated at their tips 904.

In some embodiments the pyramids are optionally rounded at their tips 904. In some embodiments the tips remain relatively sharp: in some embodiments the distal width of the pyramid tips is smaller than 150 microns. In some embodiments the tips of the pyramids have a distal radius smaller than 75 micron. It is noted that small tips distal width enable a vaporization of craters in the skin with minimal thermal damage between craters and less thermal damage than typically achieved with $CO_2$ lasers, resulting in improved treatment results relative to lasers.

FIG. 9A depicts an example embodiment array of vaporizing tips 902 which have a core 906 and are plated or coated with a biocompatible metallic envelope 908. The core 906 may be made from, by way of some non-limiting examples, copper and/or stainless steel and/or titanium and/or tungsten. The coating or plating may be made from, by way of some non-limiting example, gold and/or titanium. In some embodiments the tips are anodized.

In some embodiments, an adhesion between a biocompatible external surface, or envelope 908, and the core 906 may be achieved, by way of some non-limiting example, by silver brazing and/or by electroplating. By way of a non-limiting example, a layer of silver brazing 909 is depicted on the left side of FIG. 9A. The right side of FIG. 9A is depicted without the layer of silver brazing 909, not necessarily as an embodiment including both brazed and non-brazed areas, but as a way to show two possible methods of fastening the envelope 908 to the metallic core 906 in the one FIG. 9A In some examples the envelope 908, such as a titanium envelope, is optionally produced by sintering or by embossing or by coining.

Electroplating of Metallic Tips

In the case of copper tips, biocompatible gold plating is formed over a layer of nickel which is coated over the copper. Copper is a soft metal which becomes less stable at temperatures above 300 degrees C. At such temperatures, the tip array is sometimes crushed or distorted upon touching hard materials, potentially even upon pressing against non compliant tissue such as thin tissue over a bone. At higher temperatures, such as above 400 degrees C. and above 500 degrees C., which are used in some embodiments to clean the tips, coating a thin layer of gold (5-10 micron) on a nickel layer which is coated on top of sharp pyramidal tips of copper may be problematic—copper and nickel may diffuse into the gold layer and the gold coating with other metallic impurities becomes unsuitable as a biocompatible coating. This is particularly true when an array of pyramidal tips is produced by sintering. Sintering typically causes copper density reduction and produces micropores which limit dimensional accuracy of features below 100 microns, or 150 microns, or even 250 microns in size.

A common solution for the problem of potential deterioration of a gold coating of a sintered object is to use hard gold—gold with ~1% impurity of cobalt. However, cobalt is not a biocompatible material and also oxidizes at high temperatures, which may cause cobalt to be incompatible with clinical use. As a result, in some embodiments, hard gold may not suit to serve as a plating material for high temperature tips for treating tissue.

Other production methods for an array of tips, such as machining or electro-abrasion may be expensive in mass production due to the softness of copper, and are typically considered more stable against potential deterioration. The inventors have found that machined copper tips, as well tip arrays produced by electro-erosion are sometimes not tough enough for regular gold plating when intended to reaching high temperatures such as ~400-520 degrees C. The inventors electroplated the tips with a nickel sub-layer and with a relatively thick 10 microns pure gold layer. The gold layer was found to be not biocompatible after less than half an hour of utilization at 400 degrees C.

In some embodiments, an array of tips with metallic pyramidal or conical tips which are biocompatible and can withstand prolonged heating over 400-500 degrees C. is produced as follows:

In some embodiments sharp sintered copper tips with a distal width of 50-150 microns and a slope of 45-60 deg are used. For some embodiments a specific sintering mold has been developed with 9×9 pyramidal with sharp craters having a 100 micron distal diameter. The distance between crater centers is 1.25 mm and the depth is 2.5 mm.

Once produced, the tip array unit, including tip bottom supports, are plated with a layer of 1-5 microns of gold, optionally on top of a nickel sub-layer. Such a gold layer would typically oxidize upon attaining a temperature of 400 degrees C., and would not be biocompatible. However this gold layer will not come in contact with tissue.

In some embodiments, following a first gold layer deposited as described above, the distal tip sections which will come in contact with the tissue is them further electroplated. The further electroplating includes placing a mask over the tip array, preventing gold electroplating of the tip bases, and exposing the tip distal ends. A synergistic benefit of the mask is saving gold, since the surface is large and gold is expensive. The pyramidal tips are exposed to the plating solution. Plating voltage is applied through the mask to the metallic tip. The mask is optionally painted with an insulating paint which shapes the electrical field, producing a thickness gradient between the sharp distal end, which receives a thicker coating, and the base of the tips, which receives a thinner coating. The difference in coating thickness is due to a combination of the non conductive mask and to a stronger electric field close to the sharp tip end.

In some embodiments parameters of the electroplating process such as duration, dissolved metal solution concentration, voltage and so on, are not as would be typically used for plating a specific thickness over an entire surface of the array of tips, but according to the plating thickness of the sharp end of the tips, which is the part planned to contact tissue. For example, a gold plating thickness of ~80-140 microns on the sharp distal end of the tip is used, a thickness gradient is produced along the surface of the tips, and the bottom of the tips is plated with only a 5 micron gold layer. It may be too expensive to plate an entire surface of a tip array with an 80 micron pure gold layer, requiring tens of hours of electroplating and costing orders of magnitude more than coating just the ends of the tips.

Properties of the gold coating on a distal end of a tip after heating the tip to 520 degrees C. for a duration of 50 minutes and also an equivalent of 2,000 treatment pulses at 400 degrees Celsius were measured. The measurements were done with an electron surface scanning microscope and with EDM (Electric Dipole Moment) spectroscopy. The results showed very high stability of the coating. The results show that an 83 micron gold layer was intact after the above-described heating, and copper as well as nickel have diffused only a distance of up to 10-15 microns. A pure gold layer of over 60 microns is present, rendering the tip biocompatible and even reusable. Tips can potentially be cleaned and sterilized for at least 10 cycles at a temperature of 500 degrees C. A similar test was performed with a sintered array of gold plated stainless tips with similar good results.

It is noted that the same electroplating process without the mask produced a gold layer only 10 microns thick on the sharp distal end and a negligible gradient between the distal end of the tip and the rest of the tip array surface. The gold layer became not biocompatible after heating the tip to 400-520 degrees C. for the above-mentioned duration.

Figure 19A:
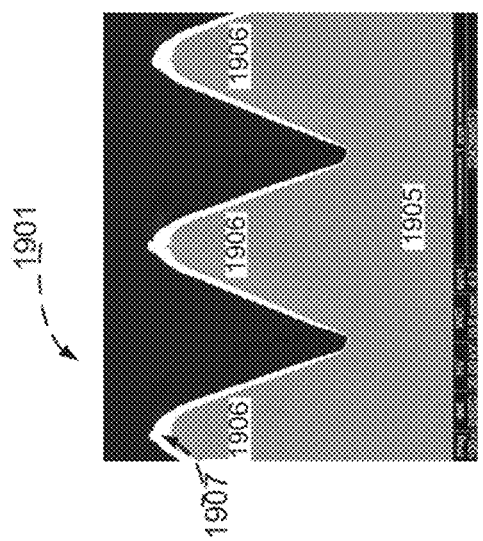
FIGS. 19A-19C are cross section images depicting stainless steel tips coated with a gold coating according to an example embodiment of the invention.
Figure 19B:
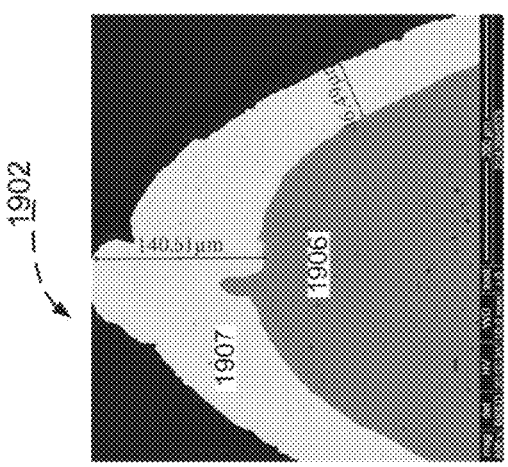
Figure 19C:
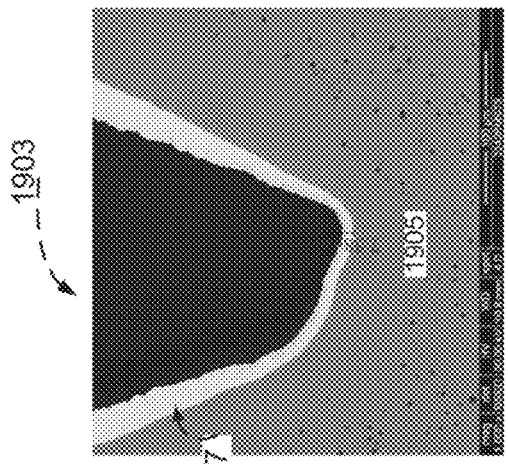

Reference is now made to FIGS. 19A-19C, which are cross section images 1901 1902 1903 depicting stainless steel tips 1906 coated with a gold coating 1907 according to an example embodiment of the invention.

FIG. 19A depicts a stainless steel base 1905 and stainless steel tips 1906 coated with gold coating 1907.

FIG. 19B depicts an enlarged section of FIG. 19A, showing one tip 1906, and gold coating on the tip 1906. FIG. 19B shows approximately 140 micron thick gold coating at the tip and approximately 45 micron thick gold coating on the sides of the tip.

FIG. 19C depicts an enlarged section of FIG. 19A, showing a bottom section of the stainless steel base 1905, and gold coating on the base 1905. FIG. 19C shows approximately 7-8 micron thick gold coating at the least thick section of the base 1905.

The thickness gradient of the gold coating is evident ~140 microns on the distal tip which is expected to contact the skin, and only 7 microns on the bottom. Most of the coated area has shallow coating, and the tips have much thicker coating.

Figure 19D:
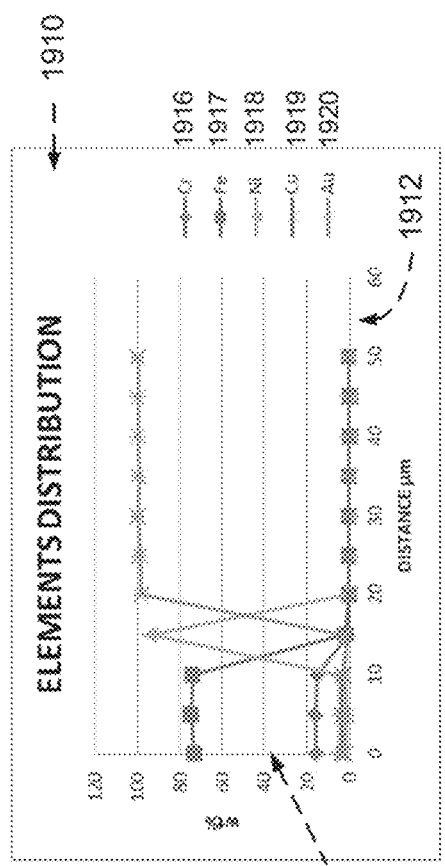
FIG. 19D is a graph depicting concentration of elements as a function of distance along the stainless steel tips and the gold coating of the example embodiment of FIGS. 19A-19C.

Reference is now made to FIG. 19D, which is a graph 1910 depicting concentration of elements as a function of distance along the stainless steel tips and the gold coating of the example embodiment of FIGS. 19A-19C.

The graph 1910 has an X-axis 1912 of distance in microns, and a Y-axis 1914 showing percentage of the elements in the material at the distance measured.

A first line 1916 in the graph 1910 shows concentration of Chrome (Cr).

A second line 1917 in the graph 1910 shows concentration of Iron (Fe).

A third line 1918 in the graph 1910 shows concentration of Nickel (Ni).

A fourth line 1919 in the graph 1910 shows concentration of Copper (Cu).

A fifth line 1920 in the graph 1910 shows concentration of Gold (Au).

The stainless steel tips and the gold coating of the example embodiment of FIGS. 19A-19C were heated at 500 degrees C. for a duration of 50 minutes.

FIG. 19D depicts a distribution of elements up to a depth of approximately 35 microns from a surface of the coating. A layer of close to 100 microns of pure gold is present. Iron and Nickel have not diffused beyond approximately 20 microns.

Figure 19E:
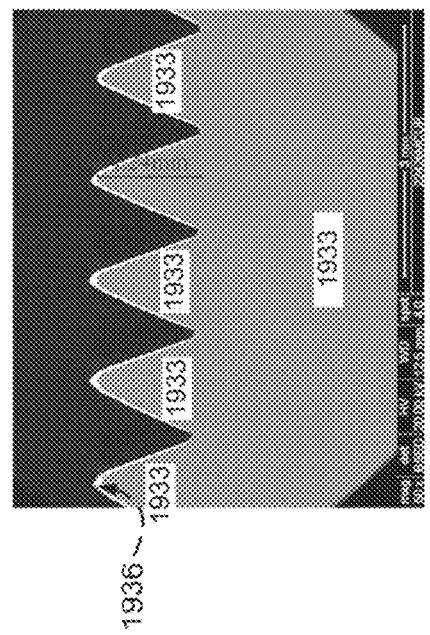
FIGS. 19E and 19F are cross section images depicting copper tips coated with a coating of nickel followed by gold according to another example embodiment of the invention.
Figure 19F:
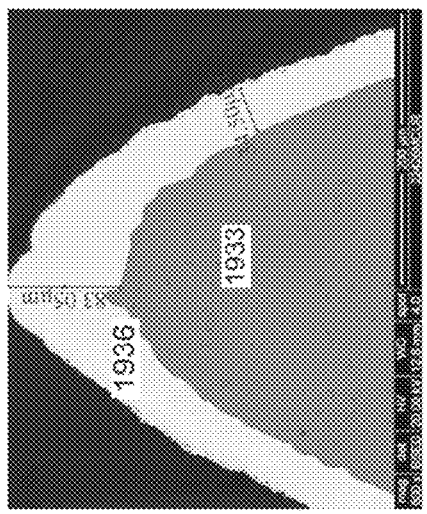

Reference is now made to FIGS. 19E and 19F, which are cross section images 1931 1932 depicting copper tips 1934 coated with a coating 1936 of nickel followed by gold according to another example embodiment of the invention.

FIG. 19E depicts a copper base 1933 and copper tips 1934 coated with the nickel followed by gold coating 1936.

FIG. 19F depicts an enlarged section of FIG. 19E, showing one tip 1933, and the nickel followed by gold coating on the tip 1936. FIG. 19F shows an approximately 83 micron thick coating at the tip and an approximately 34 micron thick coating on the sides of the tip.

Figure 19G:
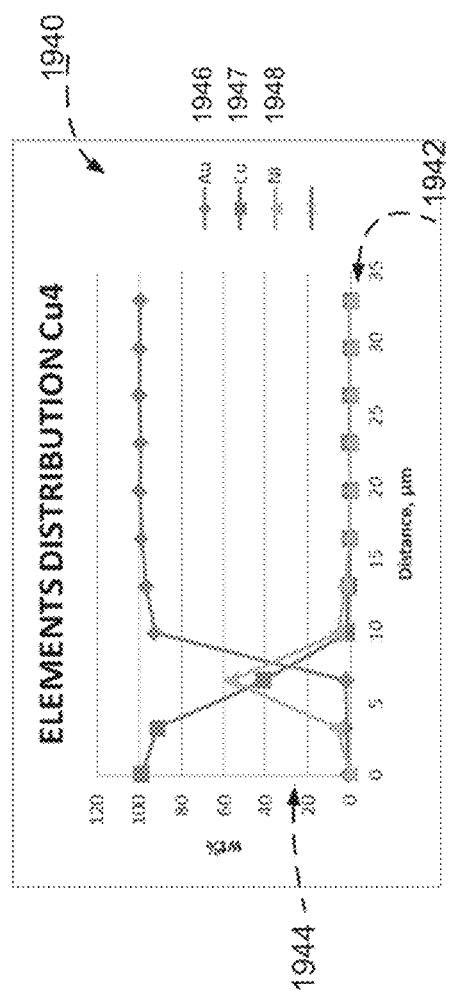
FIG. 19G is a graph depicting concentration of elements as a function of distance along the copper tips and the nickel followed by gold coating of the example embodiment of FIGS. 19E and 19F.

Reference is now made to FIG. 19G, which is a graph 1940 depicting concentration of elements as a function of distance along the copper tips and the nickel followed by gold coating of the example embodiment of FIGS. 19E and 19F.

The graph 1940 has an X-axis 1942 of distance in microns, and a Y-axis 1944 showing percentage of the elements in the material at the distance measured.

A first line 1946 in the graph 1940 shows concentration of Gold (Au).

A second line 1947 in the graph 1940 shows concentration of Copper (Cu).

A third line 1948 in the graph 1940 shows concentration of Nickel (Ni).

In the sample of the example embodiment of FIGS. 19E 19F and 19G the gold layer is 83 micron thick at the tip, and a layer of over 60 micron of pure gold is present although the tips were heated to a temperature of 520 degrees C. for 50 minutes. Since in some cases a duration of a skin rejuvenation treatment may last close to 20 minutes, the inventors heated the tips for a duration longer than 20 minutes.

In some embodiments, the array of tips is produced by using sintered copper tips which are electro-coated coated with a 6-20 micron nickel layer and further electro-coated by a 5-10 micron gold layer. It is noted that electroplating may produce a thicker coating at the tips, which are sharp and concentrate electric field. It is believed that electroplating the tips produces a synergy whereby the thicker plating is located where the array meets the tissue, and that the bio-compatible plating over a sintered array of tips is preferably formed by electroplating.

In order to test that the copper and nickel do not diffuse into the gold layer the array of tips was heated to a temperature of 520 degrees C. for a duration of 50 minutes and tested with an electron microscope for gold layer stability and with X-ray spectroscopy for Cu, Ni and Au concentrations as function of depth. The result showed high gold stability even at the sharp distal end of the tips as well as no diffusion of Cu or Ni to the surface.

A similar test was performed with a sintered array of stainless steel tips with good results.

The tests and results are described in more detail below with reference to FIGS. 19A-19G.

In some embodiments the tips may also be made from glass or ceramic.

FIG. 9B is an image of an array of tips made of stainless steel and coated with a 5 micron layer of gold. The coating layer of the distal tips is approximately 140 microns thick. The tip distal width is 200 microns.

FIG. 9C is an image of a single pyramid.

In some embodiments the shape of the array of tips may be square, such as 10×10 tips, for example on a 1 cm² area, or elongated such as a 3×10 tip rectangle, for example of 1 cm length and 5 mm width. An elongated array of tips may be useful while treating eyelids or upper lips, for example. The narrow elongated tip array near the eyes and lips or on the nose enables to avoid touching the eyes and/or the lips during treatment. The elongated array of tips may also be useful when treating very thin skin on bones as explained above, due to the dependency of Equation 3 on area D.

Figure 10:
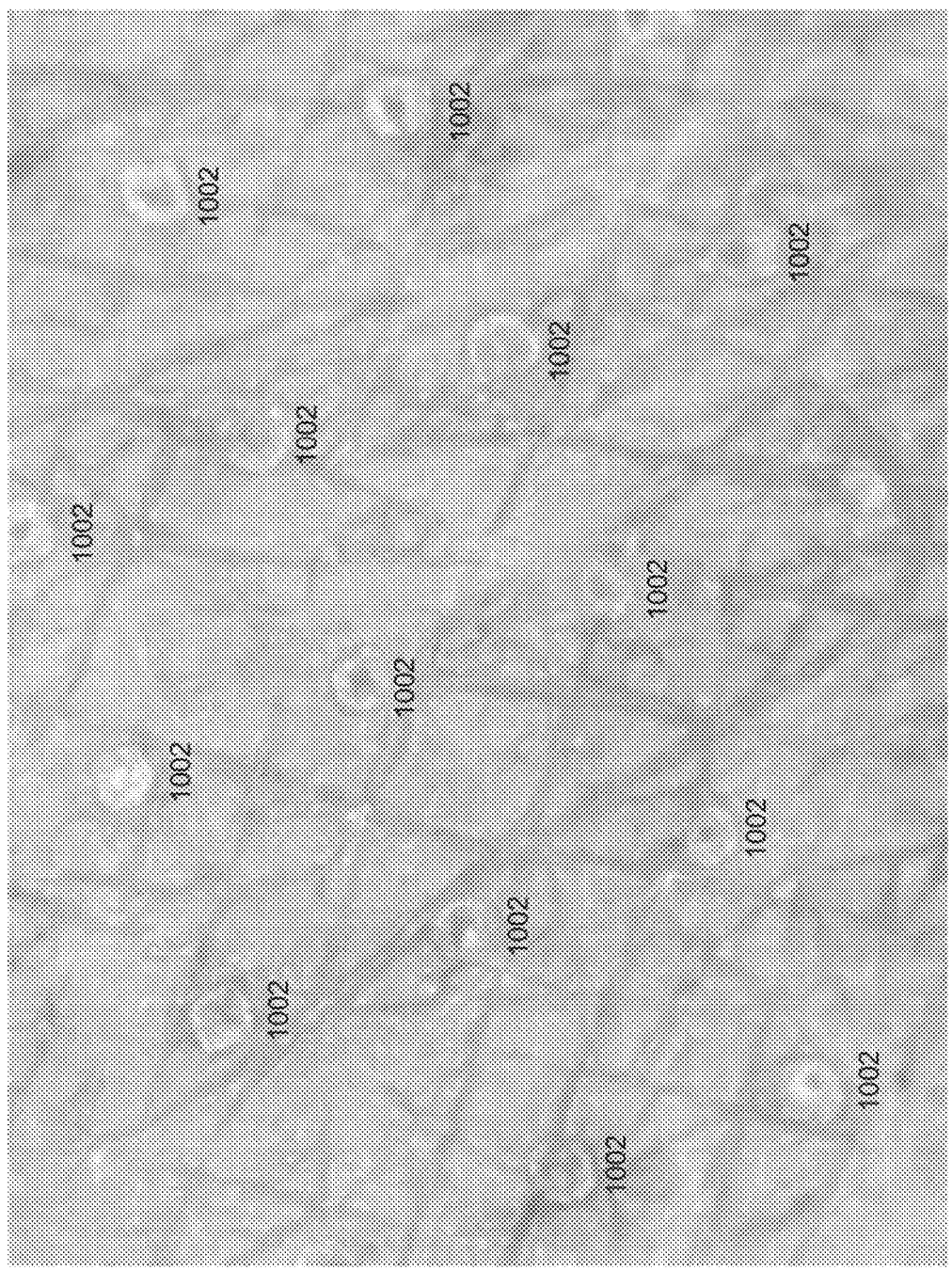
FIG. 10 is a microscope photograph of an array of pyramidal craters produced by an array of pyramidal tips according to an example embodiment of the invention.

Reference is now made to FIG. 10, which is a microscope photograph of an array of pyramidal craters 1002 produced by an array of pyramidal tips according to an example embodiment of the invention.

The pyramidal craters 1002 were produced by an array of gold coated stainless steel pyramidal tips having a distal width of 150 micron. The distance between crater centers is 1250 microns. The clean pyramidal shape of the crater is shown as well as thin collateral thermal damage having a width of only 50 microns.

In some embodiments the inventors have discovered, after a series of histologies as well as clinical tests, that the size of the distal end of the tips is preferably smaller than 150-200 microns.

Figure 20A:
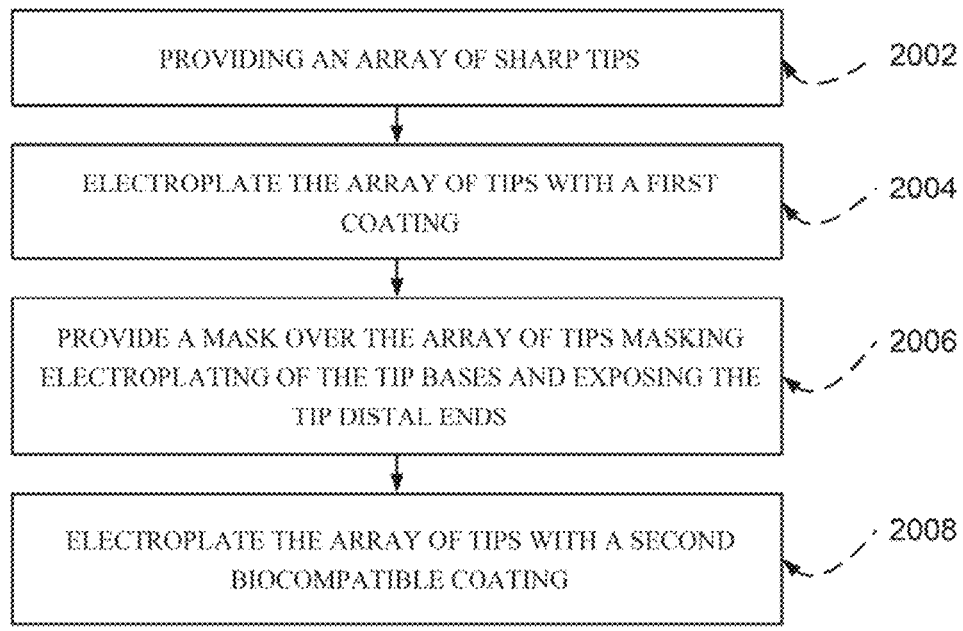
FIG. 20A is a simplified flow chart illustration of a method of producing an array of sharp metallic tips coated with a biocompatible coating according to an example embodiment of the invention.

Reference is now made to FIG. 20A, which is a simplified flow chart illustration of a method of producing an array of sharp metallic tips coated with a biocompatible coating according to an example embodiment of the invention.

The method of FIG. 20A includes:
providing an array of sharp tips (2002);
electroplating the array of tips with a first coating (2004);
providing a mask over the array of tips masking electroplating of the tip bases and exposing the tip distal ends (2006); and
electroplating the array of tips with a second biocompatible coating (2008).

In some embodiments, the mask is an insulating mask.

In some embodiments, the array of tips is produced by sintering a powder.

In some embodiments, the powder is a material such as, by way of some non-limiting examples, copper, stainless steel and titanium.

Figure 20B:
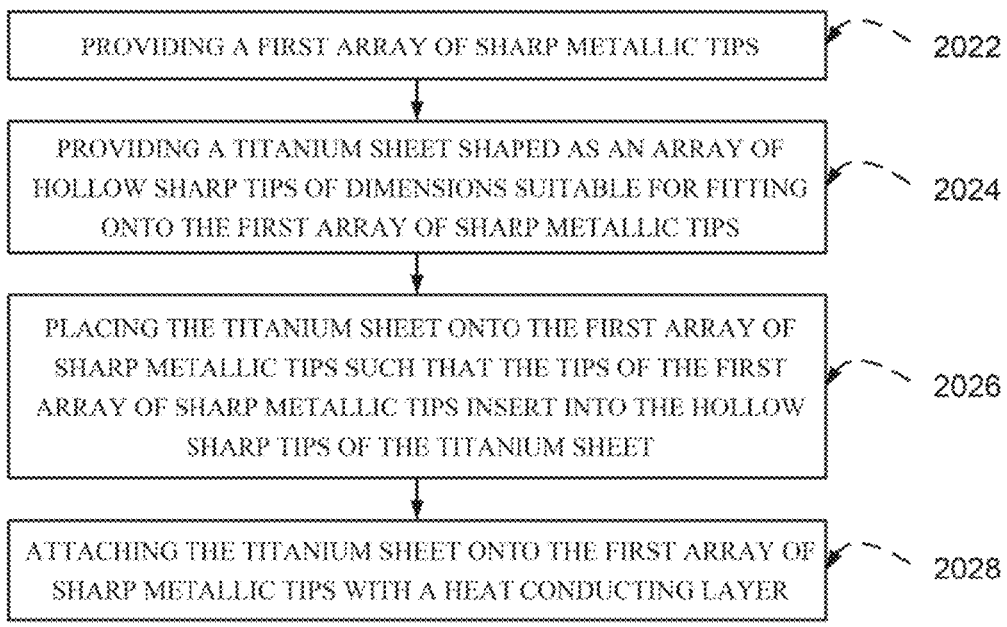
FIG. 20B is a simplified flow chart illustration of a method of producing an array of sharp metallic tips coated with a biocompatible coating according to another example embodiment of the invention.

Reference is now made to FIG. 20B, which is a simplified flow chart illustration of a method of producing an array of sharp metallic tips coated with a biocompatible coating according to another example embodiment of the invention.

The method of FIG. 20B includes:
providing a first array of sharp metallic tips (2022);
providing a titanium sheet shaped as an array of hollow sharp tips of dimensions suitable for fitting onto the first array of sharp metallic tips (2024);
placing the titanium sheet onto the first array of sharp metallic tips such that the tips of the first array of sharp metallic tips insert into the hollow sharp tips of the titanium sheet (2026; and
attaching the titanium sheet onto the first array of sharp metallic tips with a heat conducting layer (2028).

In some embodiments, the attaching is by silver brazing.

In some embodiments, the titanium sheet is produced by sintering. In some embodiments, the titanium sheet is produced by coining. In some embodiments, the titanium sheet is produced by embossment. In some embodiments, the titanium sheet is produced by machining.

Cleaning an Array of Tips

In some embodiments, array of tips are reusable and may be cleaned between treatments.

In some embodiments, tip cleaning is performed by heating the surface of the tips to a high temperature, high enough to oxidize organic material, so that carbon is oxidized into $CO_2$. Experiments performed by the inventors have shown that heating the tips above 450-500 deg C. eliminates any traces of carbon on the tip. The heating duration may be of only few minutes, for example approximately 5 minutes.

In some embodiment of the invention the heating is performed by increasing a current through a heater which heats the array of tips.

However, some heaters are not designed to withstand temperatures as high as 500 deg C.

Furthermore, when a gold coated copper tip is utilized, it may be preferable if only the gold surface is heated to a cleaning temperature, and the core material is less heated.

Reference is now made to FIG. 11, which is a simplified line drawing illustration of a heating lamp which heats a distal surface of an array of tips according to an example embodiment of the invention.

FIG. 11 depicts an array of tips 1102, optionally coated by a biocompatible coating 1104 such as gold. A lamp 1106 such as a halogen lamp produced by Herreaus, Germany, and a reflector 1108 are optionally positioned close to an array of tips which is to be cleaned and/or sterilized. In some embodiments two or more lamps are used in parallel.

Using, by way of a non-limiting example, a lamp of 300 watts over a duration of 5 minutes, the surface of the array of tips is heated to a temperature of 450-500 deg C., while not overheating the core material of the pyramids, for example not above 400 deg C.

In some embodiments the core material is kept from overheating by placing the tip array on a cooling, heat-conducting surface. In some embodiments the back side of the array of tips, which is optionally placed against a heater when in treatment mode, is placed against the cooling surface.

As a result of not overheating, thermal and mechanical properties of the pyramidal tips are preserved. The lamp cleaning assembly may be located in a console of a fractional skin resurfacing unit, or separately.

Distal End Plate—Distal Gage

Figure 12A:
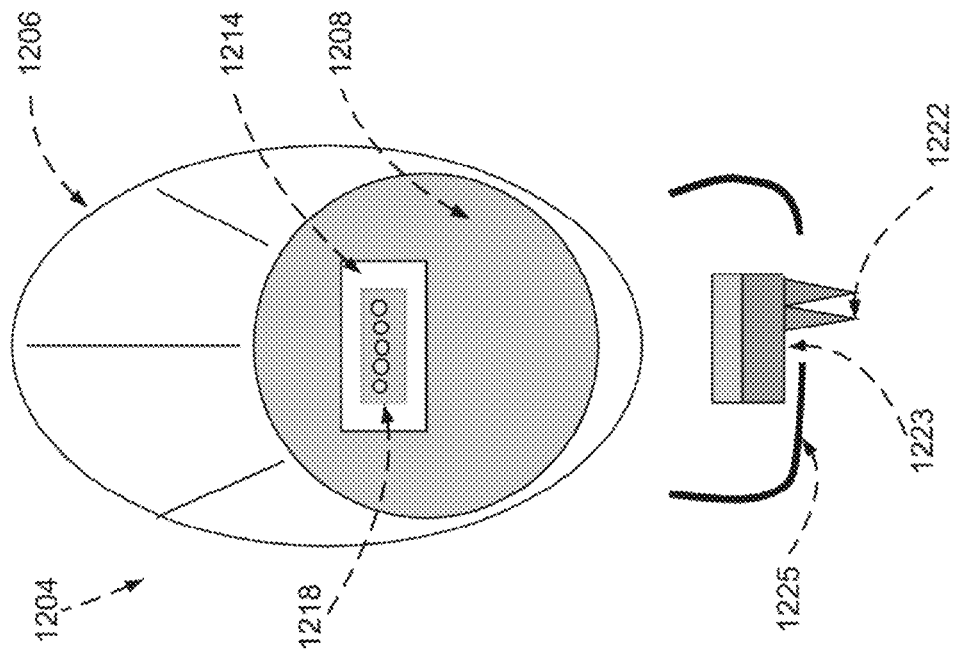
FIGS. 12A and 12B are simplified line drawing illustrations of end plates of a treatment device according to an example embodiment of the invention.
Figure 12B:
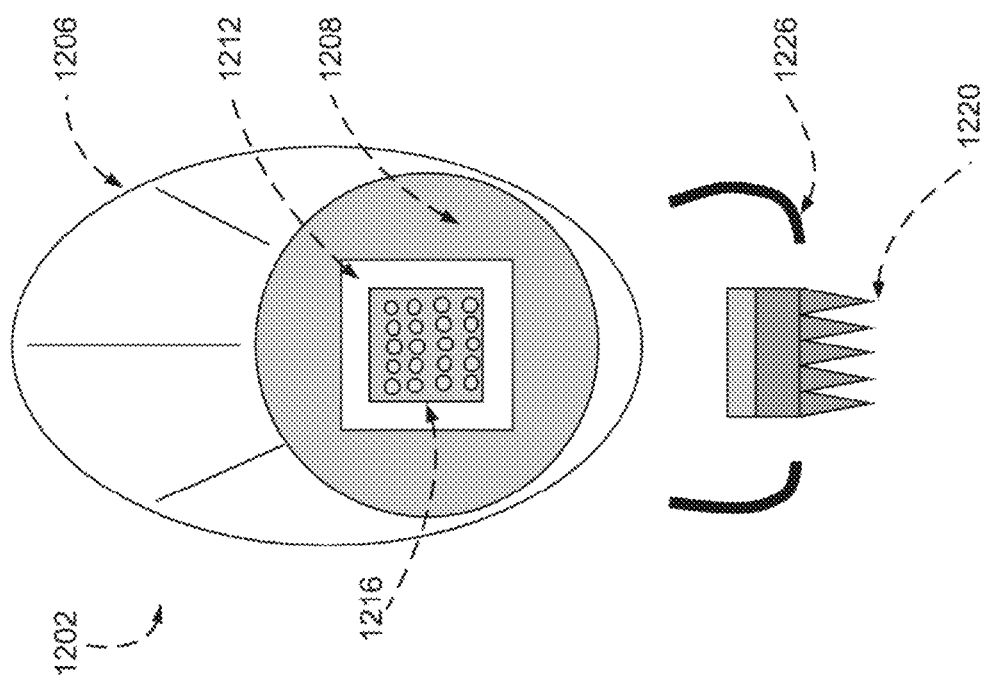

Reference is now made to FIGS. 12A and 12B, which are simplified line drawing illustrations of end plates of a treatment device according to an example embodiment of the invention.

FIGS. 12A and 12B provide a bottom view of a distal, toward-skin-side, end plates 1202 1204 or distal gages of a skin treatment device and/or hand-piece. The endplates 1202 1204 include optional transparent envelopes 1206 and/or a transparent distal surface 1208 which may be placed on the skin. Transparency is potentially beneficial for a better view of a treatment site, including enabling to locate treatments sites well aligned next to each other. Openings 1212 1214 enable arrays of tips 1216 1218 to treat tissue.

In some embodiments, the end plates 1202 1204 have different sizes of openings 1212 1214.

In some embodiments a size of an opening is not simply chosen to fit a largest array of tips 1216 1218, based on safety considerations. When an array of tips 1216 1218 contacts skin, thermal contact generates micro craters in the skin. In some cases the skin does not touch hot metal between the tips since the skin is not flexible enough.

In some embodiments, a tip array 1222 may be produced by removing some tips from an array of tips 1220 originally having more tips. In such cases skin may contact with hot metal in the region 1223 where tips have been removed. By protecting the array of tips 1216 1218 with distal plates 1225 1226 as in FIGS. 12A and 12B, such a condition may potentially be avoided.

In some embodiments a distal endplate includes two slits which enable changing a used array of tips with a new array of tips without removing the distal endplate, as described below with reference to FIGS. 13A-I.

Changing an Array of Tips

In some embodiments a treatment device for thermal tissue vaporization and compression is designed so there is no possibility to unintentionally touch a high temperature tip array, for example with a finger or hand. Openings in the distal gage mentioned above are small—smaller than the dimensions of the tip array unit which includes an array support, while still large enough to enable skin treatment to be performed (for example larger than 10 millimeters per side).

In some embodiments, it is desirable to discard a used tip array after a treatment session, so that a clean and/or disinfected tip may be used in the next treatment. Changing tips should preferably be rapid, for example taking no more than 1-2 minutes, and should be possible to perform at high temperature such as 400 degrees C., since the cooling off period for a tip array may be longer than the changing time.

In some embodiments, changing tips is optionally done by sliding the tip array unit sideways relative to the distal gage, through a slit and out of the treatment device, without overheating the distal gage and/or risking operator safety, even while at high temperature. The tip array which is hot is dropped into a box for safe keeping and cooling off. Charging a new tip into the treatment hand-piece is also preferably rapid, and optionally performed as part of a same tip array changing procedure. In some embodiments, it is advantageous to change the tip array using a small unit such as a console with a single motor. Furthermore, a hot (temperature above approximately 300 degrees C.) array of copper tips may be soft and distort if exchanged incorrectly or by using excessive force.

In some embodiments it is advantageous to change tips in a small closed console.

In some embodiments the tips are changes by pushing a sliding mechanism by hand and/or better by a motor.

Reference is now made to FIGS. 13A-I, which are simplified line drawing illustrations of a mechanism for quick change of an array of tips according to an example embodiment of the invention.

The example mechanism depicted in FIGS. 13A-I potentially enables exchanging a used array of tips with a new array of tips while the used array of tips is still hot.

In some embodiments of the invention an array of tips may be removed from a treatment hand-piece after one or more treatments, to be replaced by a new array of tips. Moreover, arrays of tips may be removed while still hot, for example even 500 deg C. In addition, the arrays of tips may be removed safely while still hot without endangering hands or fingers which are holding the hand-piece.

FIGS. 13A-I depict a compartment or console 1302 which includes an opening 1304 through which a treatment hand-piece 1306 or part of the treatment hand-piece 1306 may be introduced.

Figure 13A:
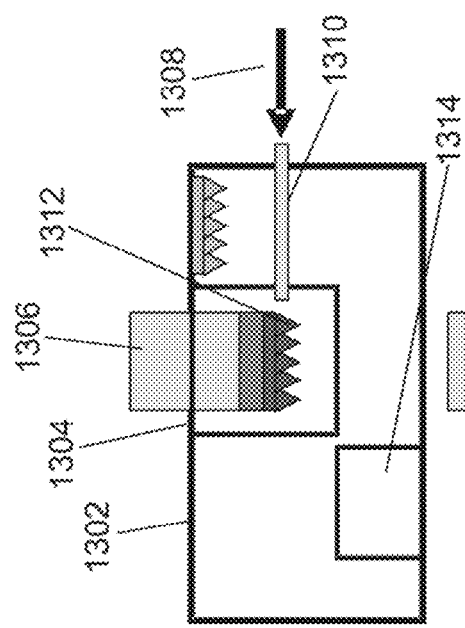
FIGS. 13A-I are simplified line drawing illustrations of a mechanism for quick change of an array of tips according to an example embodiment of the invention.

FIG. 13A depicts a mechanism 1308 which may be operated manually, or operated by a motor, whereby an extension rod 1310 or plate optionally pushes a first array of tips 1312 away from the hand-piece 1306. The first array of tips 1312 may be at any temperature. Once the first array of tips 1312 has been pushed away from the hand-piece (FIG. 13B), it is optionally allowed to fall into a compartment 1314, which optionally enables a disposal of used arrays of tips (FIG. 13C).

Figure 13B:
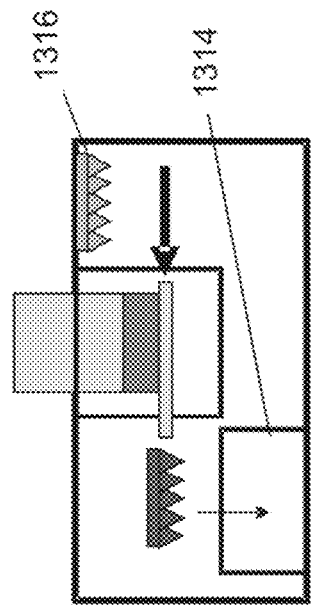
Figure 13C:
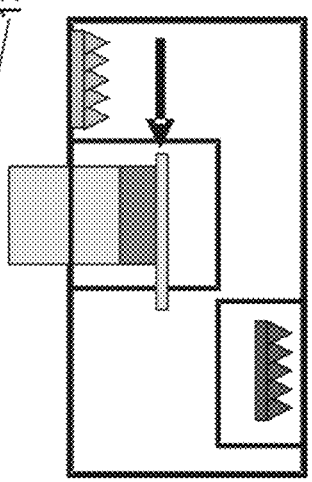
Figure 13D:
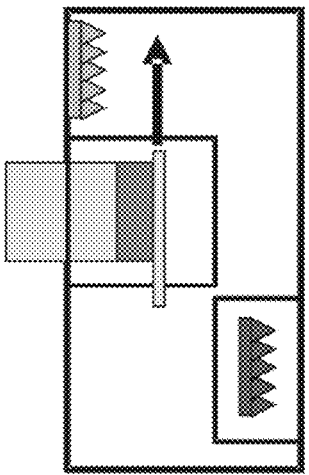

FIG. 13B also depicts a second array of tips 1316, such as for example a gold plated array of tips 1316, which is optionally held waiting to be used. Once the first array of tips 1312 have been dropped into the 1314, the extension rod 1310 is optionally pulled back by the mechanism 1308 in a reverse direction (FIG. 13D).

In some embodiments a mechanism for pulling may be a separate mechanism from the mechanism 1308 for pushing.

Figure 13E:
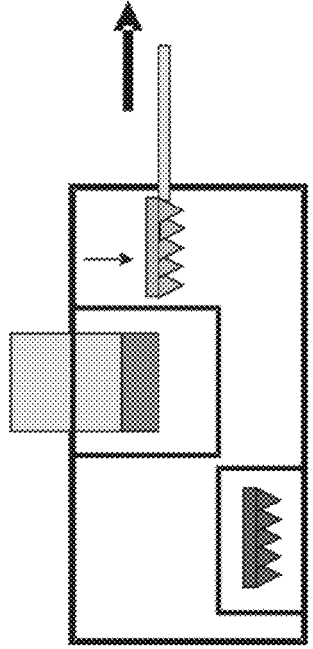
Figure 13F:
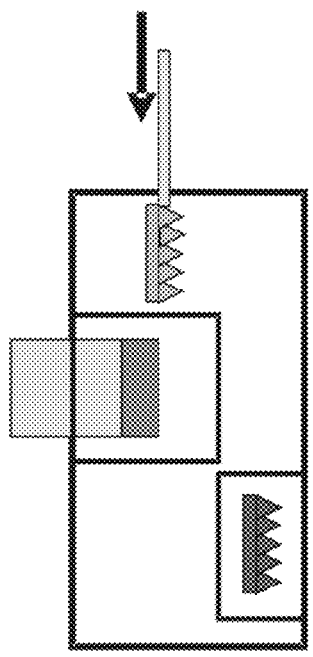

Once the extension rod 1310 is back in its original position, the second array of tips 1316 is optionally let fall (FIG. 13E). The mechanism 1308 optionally starts to work as a pushing mechanism, which pushes the second array of tips 1316 to its location in contact with in the hand-piece 1302 (FIG. 13F).

Figure 13H:
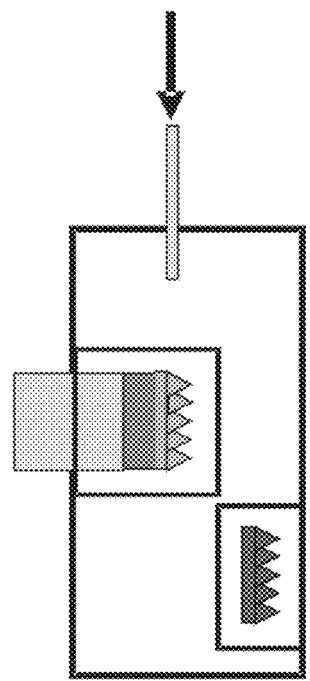
Figure 13G:
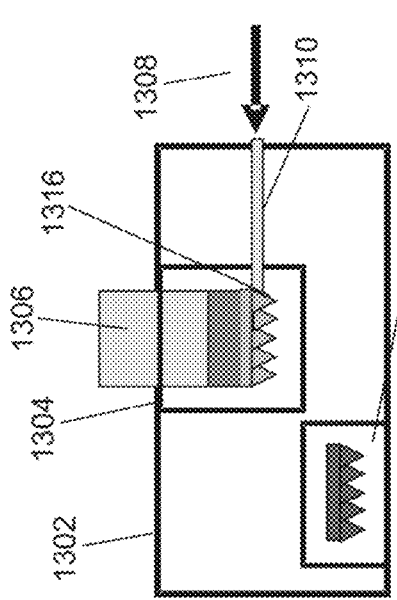
Figure 13I:
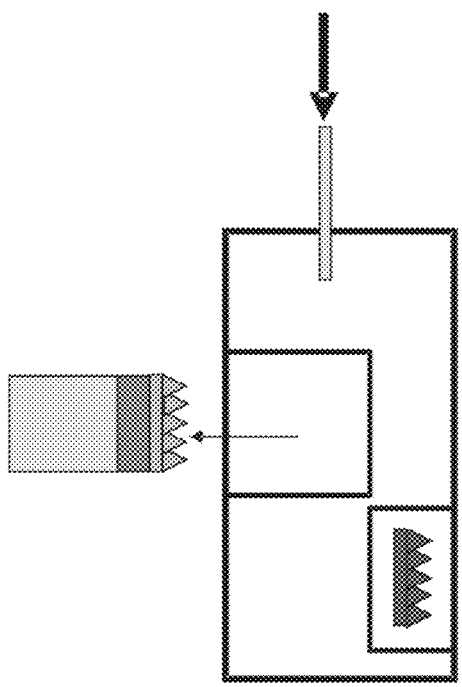

The hand-piece 1302, loaded with the second array of tips 1318, is ready to be removed from the console 1302 and potentially treat a new patient (FIGS. 13G, 13H, 13I).

Reference is now made to FIG. 14, which is a simplified line drawing illustration of a mechanism for changing an array of tips according to another example embodiment of the invention.

In some embodiments, operation of the mechanism for changing an array of tips is controlled in several ways, including by manual control, by motorized control which may be manually activated or activated by control from a control panel, and by a microprocessor.

FIG. 14 depicts a hand-piece 1400 with a transparent distal gauge 1402 placed on top of a changing mechanism 1404 for an array of tips. The array of tips is optionally held in place in the treatment hand-piece 1400 by a spring which pushes the array of tips against a surface. By pressing the spring, its pushing action is stopped and the array of tips may slide horizontally while being pushed linearly by a motor 1406.

The holder of the array of tips optionally includes a lever with a pin. A rotation of a rotary solenoid 1408 optionally rotates a sliding ring 1412 by a desired angle. The rotation of the sliding ring optionally activates a mechanism 1410, which optionally releases the array of tips from its place in the treatment hand-piece 1400. Once released, the array of tips is optionally attached to a sliding track and may be driven out of the hand-piece 1400 by the motor 1406. The sliding ring 1412 is optionally built as a cam which releases the array of tips as well as attaches the array of tips to the sliding track, optionally without additional control.

A holder 1414 for the array of tips optionally holds a new array of tips, which optionally replaces the used array of tips. The new array of tips is optionally placed on a sterile holder which potentially stays sterile since there is no human contact.

In some embodiments the motor 1406 is a linear motor.

In some embodiments the motor 1406 includes a linear encoder.

Figure 17:
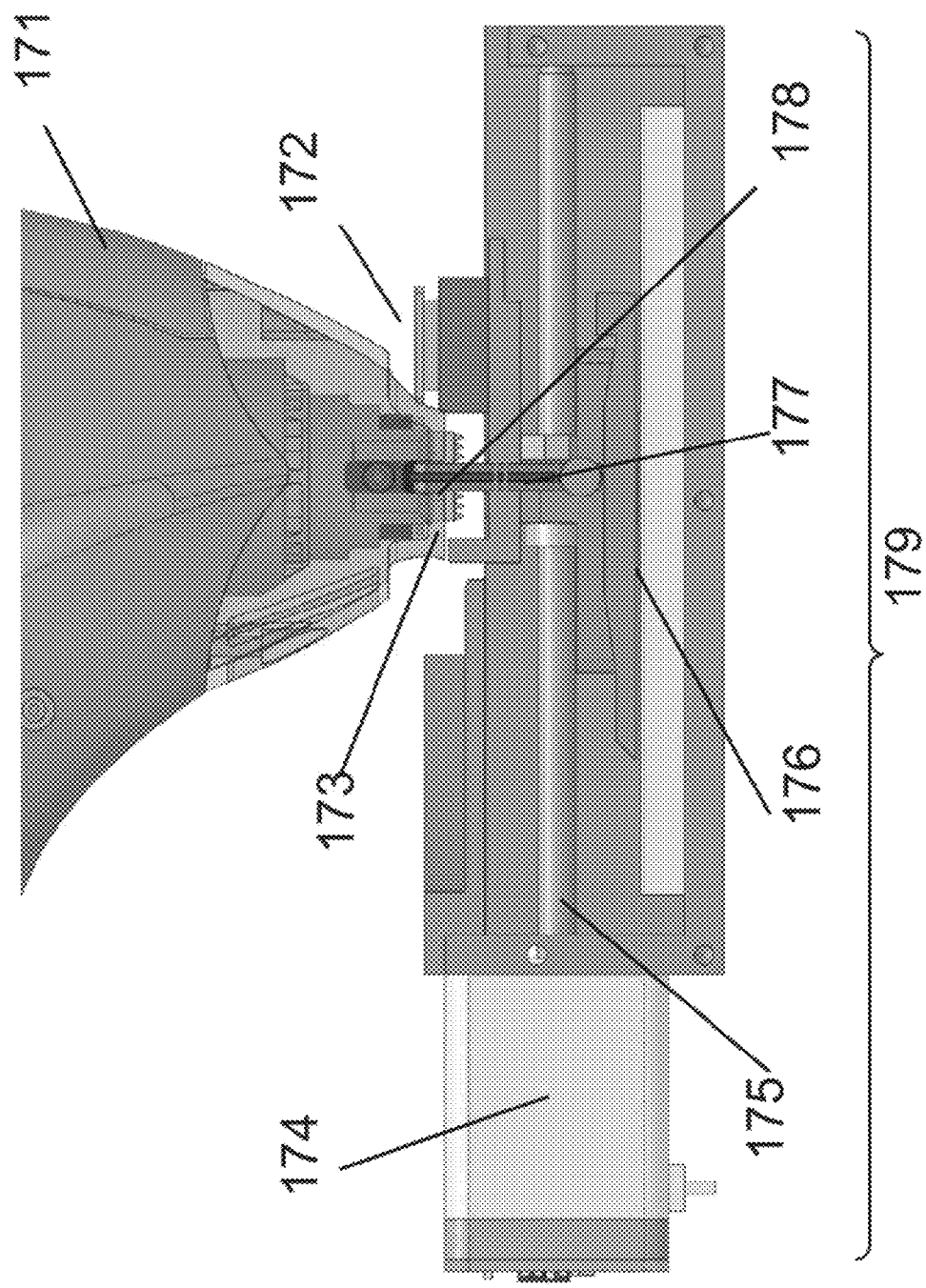
FIG. 17 is a simplified line drawing illustration of a mechanism for quick change of an array of tips according to another example embodiment of the invention.

Reference is now made to FIG. 17, which is a simplified line drawing illustration of a mechanism for quick change of an array of tips according to another example embodiment of the invention.

FIG. 17 depicts a hand-piece 171 placed in an opening of a tip array changing mechanism 179. A new tip array 172 will replace an old tip array 173. The old tip array may be hot, even up to a temperature of approximately 400 degrees C. A motor 174, which optionally includes a rotary encoder to determine position, moves a screw 175 which slides tip the old tip array 173 using a track 176. An optional cylindrical element 178 may optionally releases the old tip array 173 prior to the process of discarding the old tip array 173, and an element 177 may optionally fix the new tip array 172 following placement of the new tip array 172 in the hand-piece 171.

Tip Inspection

In some embodiments, a console unit optionally includes a tip inspection device. The tip inspection device optionally includes a light source, which optionally measures reflection from a surface of an array of tips, and/or an infrared radiometer which measures infrared emission from the surface of the array of tips.

In some embodiments, infrared emission from the surface should not be higher than a preselected value such as 20% emissivity.

In some embodiments the inspection mechanism includes a camera.

A Console Unit

Figure 15:
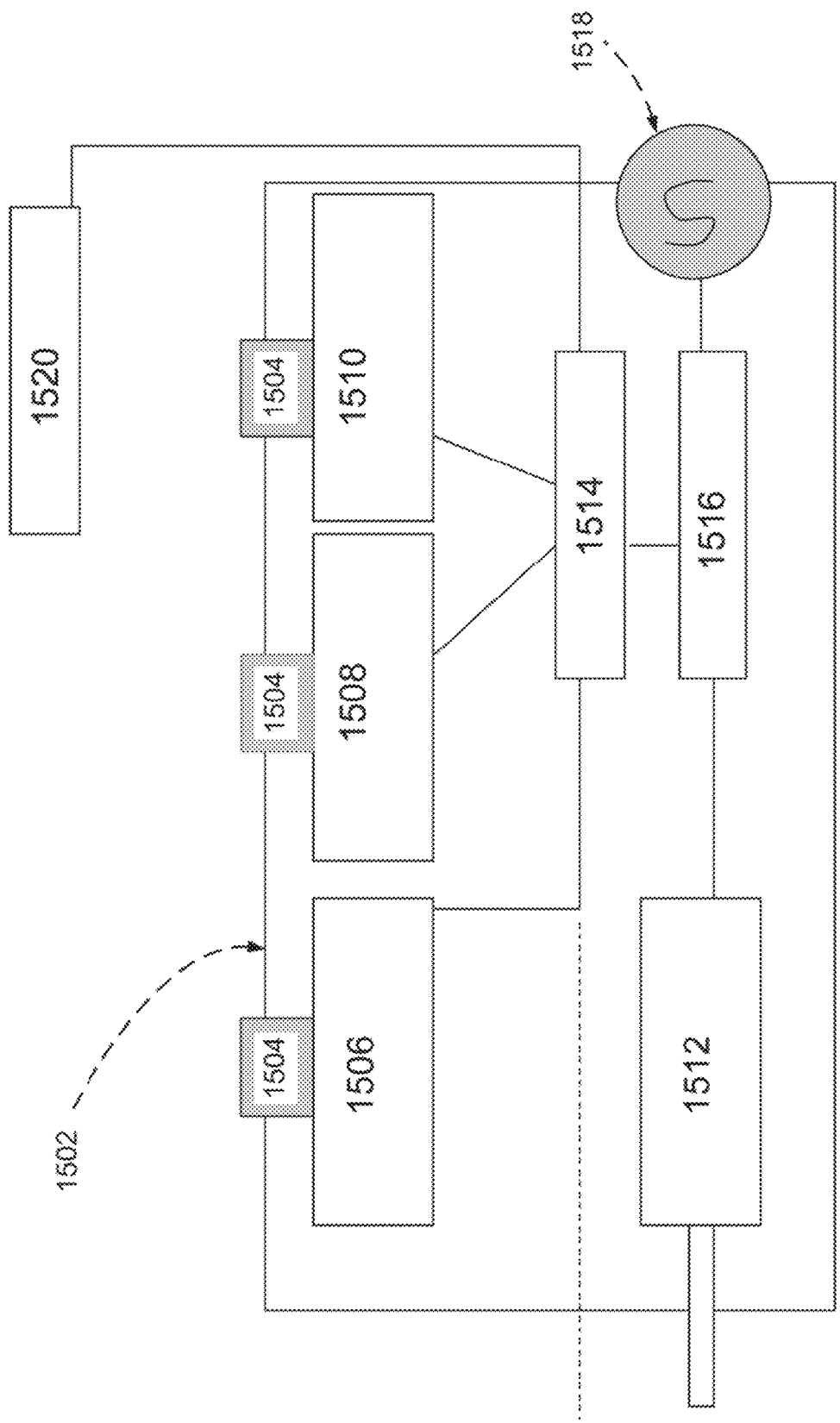
FIG. 15 is a simplified block diagram of a console unit according to an example embodiment of the invention.

Reference is now made to FIG. 15, which is a simplified block diagram of a console unit according to an example embodiment of the invention.

As explained above, patient treatments are typically performed at high temperatures, which may attain temperatures above 400 deg C. Under such circumstances, safety should optionally be considered and technically applied.

For example, when momentarily pausing a treatment, the hand-piece should optionally be placed in such a way that an operator is prevented from accidentally touching the high temperature array of tips.

For example, while changing tips from a used tip to a new tip, an action which in a preferable embodiment should be rapid, the tip change should be carried out while the tips are still hot, without waiting for a tip to cool.

For example, a used array of tips is preferably disposed of, since the used tips may not be clean, and the used tips may be made of copper which requires disposal.

FIG. 15 depicts a console 1502 which includes openings 1504 thorough which treatment hand-piece(s) or arrays of tips may optionally be introduced. The console 1502 optionally also includes one or more of: a control panel 1520; an array of tips changing unit 1506; an array of tips cleaner device 1508; a tip inspection unit 1510; a suction pump 1512 which may optionally be connected to a treatment hand-piece through a hose; a microprocessor 1514 which may optionally control one or more of the control panel 1520, array of tips changing unit 1506; the array of tips cleaner device 1508, and the tip inspection unit 1510.

In some embodiments the console 1502 also includes a power supply 1516 and/or a 110/220 V mains connection 1518.

Clinical Applications Using Example Embodiments

Example 1

In addition to skin treatments mentioned above, the heated gold-coated pyramidal tips can be advantageous in a broad range of surgical applications. The heated gold-coated pyramidal tips can replace $CO_2$ laser treatments in many cases.

A capability of precisely controlling vaporization depth in receding or flexible tissue enables substantial improvement of state of the art surgery of thin body walls.

Non-limiting examples of such thin and flexible tissues include: a tympanic membrane, which is approximately 250-1000 micron thick; walls of fallopian tubes; and vocal cords. These tissue walls, or membranes, are typically treated with focused pulsed $CO_2$ lasers, causing little peripheral thermal damage. In the above cases, in addition to using an expensive laser, (single mode, and very short pulse duration) there is also a need for a focusing beam manipulator, which is uncomfortable to a user and to a patient, and is time consuming (finding the focal position).

In some embodiments, a high temperature tip at 200-600 deg C. is used for vaporization of a crater in such walls or membranes, as described in above-mentioned published PCT publication WO2011/013118. Published PCT publication WO2011/013118 still requires a way to let the high temperature tip to reach the surface of the membrane and control depth of penetration with high accuracy, for instance using an optical focusing method.

Using an example embodiment, it is now easier to treat the membranes. During an advance of a high temperature tip toward the membrane, the linear motor which controls the tip advance senses the arrival of the tip at the membrane surface, since mechanical impedance becomes larger. Since the position of the tip is known with an accuracy of ~1-2 microns, the motor may receive instructions whereby it advances the tip to a preselected distance, such as 250 microns, and immediately reverse the tip advancement. As a result, high quality drilling or incisions are made possible without a need for depth measurement using focusing optics. The tip is optionally inserted in an endoscope, for example in a case such as treatment of a fallopian tube, or in an otoscope such as in the treatment of a tympanic membrane, or in a hand-piece such as in the treatment of vocal cords.

High Frequency Treatments

In some embodiment, the high temperature tips are optionally applied to tissue in pulses, optionally at a high frequency, such as from 1-200 Hz. While sensing mechanical compliance of tissue in receding tissue or in tissue covering a bone, it is possible to use a fast mechanical compliance sensing mode, such as every 10 milliseconds, or a slower mechanical compliance sensing mode such as every 100 milliseconds. In some embodiments sensing the mechanical compliance is performed practically continuously.

A high repetition mechanical compliance sensing mode may potentially be advantageous in several cases.

Example 2

An Incision of a Fallopian Tube

In some embodiments, by operating a tip at a frequency such as 50 Hz, that is advances and retractions of a tip or array of tips per second, and at the same time advancing with the tip/array, a row of craters may be produced.

In some embodiments, by advancing at a speed which enables some overlap of craters, an incision is optionally produced.

In some embodiments, by repeating a process of producing an incision, further depth of the incision is attained and incision of a full thickness tissue is optionally achieved. It is noted that in some embodiments, it is possible to provide a clean way to incise fallopian tubes without bleeding, or with much reduced bleeding, and with minimal or reduced peripheral damage.

Example 3

Generation of a High Density of Craters in the Stratum Cornea or Epidermis

In some embodiments a linear array of tips, such as 1 row of tips by 10 tips per row, which advances and retreats at a high frequency such as 50 Hz, is translated across skin during treatment. An example movement velocity may be 200 microns within 20 milliseconds, which translates to 1 cm/sec. An example distal width of the tips is 100 microns. As an example result, lines of 10 craters are sequentially produced at a distance of every 200 microns. If the handpiece is translated as described for 10 seconds, a large area of 10 craters by 500 craters at a high density is generated, with the craters separated by 100 microns in the direction of motion.

Example 4

Incising Adhesions

Incising adhesions is typically performed to solve a common surgical problem. The incising is presently commonly performed laparoscopically by electrosurgery. However electrosurgery poses some risks of burn. A potential risk is an accidental return of electric current to ground through a body organ, resulting in a burn. Incision of adhesions with a $CO_2$ laser is also often risky since a multiple section articulate arm which is part of the $CO_2$ laser device is often not well aligned. Long term angular beam alignment accuracy of 1 milliradian is generally considered technologically challenging, and misalignment is a reason of many service calls. With a 1 meter long articulate arm the potential misalignment can translate into a 1 mm invisible $CO_2$ laser beam position inaccuracy on a tissue target. In many laparoscopic incisions such accuracy is unacceptable. Furthermore, a 1 milliradian inaccuracy may cause an edge of the laser beam to be reflected from endoscope walls and to be focused on an unpredictable site. This may result in a requirement for mechanically very stable and expensive articulated arms. An endoscopic heated tip according to some embodiments of the invention, which vibrates and is translated along an adhesion, potentially makes an incision by acting as a safe knife. The position of the cutting tip on the tissue is directly observed, as opposed to the position of an invisible laser beam. The benefit of safety is provided also as a result of at least one of several features described above, such as using a value for skin compliance for open loop control, and/or using a measured depth into tissue based on measuring distance beyond a start of tissue impedance for closed loop control. An operator advances the tip toward contact with tissue, for example tissue such as the fallopian tube wall, optionally using laparoscope viewing optics, and controls incising optionally using as feedback measurement of mechanical compliance or resistance. The operator optionally places a heated tip at the right position, posing no surgical risk, including no burn risk.

It is expected that during the life of a patent maturing from this application many relevant tip and tip coating materials will be developed and the scope of the terms tip and tip coating are intended to include all such new technologies a priori.

As used herein the term "about" refers to ±20%.

The terms "comprising", "including", "having" and their conjugates mean "including but not limited to".

The term "consisting of" is intended to mean "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a unit" or "at least one unit" may include a plurality of units, including combinations thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A device for producing an array of micro-depressions in the stratum corneum of skin having a controlled depth of up to 150 microns, comprising:
   at least one thermally heated tip, for producing said array of micro-depressions;
   a motion controller; and
   a closed loop advancing and retracting mechanism, coupled with said at least one thermally heated tip and said motion controller, for advancing said at least one thermally heated tip towards skin and retracting said at least one thermally heated tip from skin;
   said closed loop advancing and retracting mechanism comprising a position encoder for providing feedback to said closed loop advancing and retracting mechanism,
   wherein said position encoder and said motion controller are for controlling a position of said at least one thermally heated tip within the stratum corneum of skin as a function of time;
   wherein said closed loop advancing and retracting mechanism detects contact of said at least one heated tip with skin; and
   wherein said closed loop advancing and retracting mechanism advances said at least one thermally heated tip in skin to said controlled depth according to said position encoder and said motion controller measures a position of said at least one thermally heated tip when said closed loop advancing and retracting mechanism detects contact of said at least one thermally heated tip with skin.

2. The device of claim 1 wherein said closed loop advancing and retracting mechanism is a motor.

3. The device of claim 2, wherein said motor is selected from the list consisting of:
   an electric motor;
   a linear motor; and
   a rotary motor.

4. The device according to claim 1, wherein said controlled depth is controlled by a current of said motion controller and determined as a percentage of remaining stratum corneum to an area of already vaporized stratum corneum which produced said micro-depression.

5. The device according to claim 4, wherein said percentage is selected from the list consisting of:
   at least 30%;
   at least 50%;
   at least 80%; and
   approximately 100%.

6. The device according to claim 1, wherein said at least one thermally heated tip is an array of thermally heated tips.

7. The device according to claim 1, wherein said closed loop advancing and retracting mechanism detects said contact of said at least one thermally heated tip with skin by detecting a pre-determined amount of mechanical resistance of skin to said advancing of said at least one thermally heated tip by a measured current of said motion controller.

8. The device according to claim 1, wherein said position encoder can also determine a velocity of an advancement of said at least one thermally heated tip.

9. The device according to claim 8, wherein said motion controller and said position encoder detect said contact of said at least one thermally heated tip with skin by detecting a pre-determined reduction in velocity of said advancing of said at least one thermally heated tip.

10. The device according to claim 1, wherein said position encoder is selected from the list consisting of:
   a linear encoder;
   a rotary encoder;
   a magnetic array type encoder;

an optical encoder; and
a Hall effect encoder.

11. The device according to claim 1, further comprising a processor, coupled with said closed loop advancing and retracting mechanism, for assessing mechanical compliance of skin when said closed loop advancing and retracting mechanism detects said contact of said at least one thermally heated tip with skin by a pre-determined change in at least one of a measured current and a measured voltage of said motion controller.

12. The device according to claim 11, wherein said assessing is according to a measured mechanical resistance of skin to said at least one thermally heated tip.

13. The device according to claim 11, wherein said processor determines a continued advancing of said at least one thermally heated tip according to said assessing.

14. The device according to claim 13, wherein said continued advancing is a pre-determined distance to advance said at least one thermally heated tip beyond said detected contact of said at least one thermally heated tip with skin.

15. The device according to claim 11, wherein said processor assesses mechanical compliance of skin while said closed loop advancing and retracting mechanism advances said at least one thermally heated tip into skin.

16. The device according to claim 15, wherein said closed loop advancing and retracting mechanism advances said at least one thermally heated tip into skin beyond said detected contact of said at least one thermally heated tip with skin as long as an assessment of said processor of said mechanical compliance of skin remains lower than a threshold value.

17. The device according to claim 16, wherein said assessment of said processor of mechanical compliance of skin while said closed loop advancing and retracting mechanism advances said at least one thermally heated tip into skin is according to the following equation:

$$F=k*Y*D^4*\mu/t*(Z^3),$$

wherein F is a driving force of said closed loop advancing and retracting mechanism advancing said at least one thermally heated tip;
k is a constant;
Y is a distance within skin following a contact of said at least one thermally heated tip with skin;
D is an area of a cross section of said at least one thermally heated tip;
μ is a viscosity of skin;
t is a time measured following said contact of said at least one thermally heated tip with skin; and
Z is a distance from skin to a hard surface beneath skin.

18. The system according to claim 1, wherein said motion controller advances said closed loop advancing and retracting mechanism using pulse width modulation (PWM).

19. The system according to claim 1, further comprising a distal cover, for distancing said at least one thermally heated tip from skin before said closed loop advancing and retracting mechanism advances said at least one thermally heated tip towards skin.

20. The system according to claim 19, wherein said closed loop advancing and retracting mechanism detects said contact of said at least one thermally heated tip with skin when said at least one thermally heated tip is advanced beyond said distal cover.

21. A system for producing at least one crater in the stratum corneum of tissue having a controlled depth of up to 150 microns, comprising:
at least one thermally heated tip, for producing said at least one crater; and
a closed loop advancing and retracting mechanism, coupled with said at least one thermally heated tip, for advancing said at least one thermally heated tip towards and into tissue and retracting said at least one thermally heated tip from tissue;
said closed loop advancing and retracting mechanism comprising a detection module, for detecting when said at least one thermally heated tip comes into contact with tissue according to a change in mechanical resistance of said advancing said at least one thermally heated tip,
wherein said detection module provides feedback to said closed loop advancing and retracting mechanism for controlling a position of said at least one thermally heated tip within the stratum corneum of tissue as a function of time; and
wherein said closed loop advancing and retracting mechanism advances said at least one thermally heated tip in tissue to said controlled depth from when said at least one thermally heated tip comes into contact with tissue according to said feedback from said detection module.

22. The system according to claim 21, wherein said controlled depth is controlled by a current of said motion controller and determined as a percentage of remaining stratum corneum to an area of already vaporized stratum corneum which produced said at least one crater.

23. The system according to claim 22, wherein said percentage is selected from the list consisting of:
at least 30%;
at least 50%;
at least 80%; and
approximately 100%.

24. The system according to claim 21, wherein said at least one thermally heated tip is an array of thermally heated tips.

25. The system according to claim 21, wherein said closed loop advancing and retracting mechanism is a motor.

26. The system according to claim 25, wherein said motor is selected from the list consisting of:
an electric motor;
a linear motor; and
a rotary motor.

27. The system according to claim 21, wherein said detection module comprises:
a position encoder; and
a motion controller.

28. The system according to claim 27, wherein said position encoder is selected from the list consisting of:
a linear encoder;
a rotary encoder;
a magnetic array type encoder;
an optical encoder; and
a Hall effect encoder.

29. The system according to claim 21, further comprising a processor, coupled with said closed loop advancing and retracting mechanism, for assessing mechanical compliance of tissue when said detection module detects contact of said at least one thermally heated tip with tissue by a pre-determined change in at least one of a measured current and a measured voltage of said detection module.

30. The system according to claim 29, wherein said assessing is according to a measured mechanical resistance of tissue to said at least one thermally heated tip.

31. The system according to claim 29, wherein said processor determines a continued advancing of said at least one thermally heated tip according to said assessing.

32. The system according to claim 31, wherein said continued advancing is a pre-determined distance to advance said at least one thermally heated tip beyond said detected contact of said at least one thermally heated tip with tissue.

33. The system according to claim 29, wherein said processor assesses mechanical compliance of tissue while said closed loop advancing and retracting mechanism advances said at least one thermally heated tip into tissue.

34. The system according to claim 33, wherein said closed loop advancing and retracting mechanism advances said at least one thermally heated tip into tissue beyond said detected contact of said at least one thermally heated tip with tissue as long as an assessment of said processor of said mechanical compliance of tissue remains lower than a threshold value.

35. The system according to claim 34, wherein said assessment of said processor of mechanical compliance of tissue while said closed loop advancing and retracting mechanism advances said at least one thermally heated tip into tissue is according to the following equation:

$$F = k*Y*D^4*\mu/t*(Z^3),$$

wherein F is a driving force of said closed loop advancing and retracting mechanism advancing said at least one thermally heated tip;

k is a constant;

Y is a distance within tissue following a contact of said at least one thermally heated tip with tissue;

D is an area of a cross section of said at least one thermally heated tip;

μ is a viscosity of tissue;

t is a time measured following said contact of said at least one thermally heated tip with tissue; and Z is a distance from tissue to a hard surface beneath tissue.

* * * * *